(12) United States Patent
Nasser et al.

(10) Patent No.: US 8,093,031 B2
(45) Date of Patent: Jan. 10, 2012

(54) HEPARANASES AND SPLICE VARIANTS THEREOF, POLYNUCLEOTIDES ENCODING THEM AND USES THEREOF

(75) Inventors: Nicola J. Nasser, Nazareth (IL); Aaron Avivi, D.N. Misgav (IL); Israel Vlodavsky, Mevasseret Zion (IL); Eviatar Nevo, Haifa (IL)

(73) Assignee: Carmel-Haifa University Economic Corp. Ltd., Mount Carmel (IL)

( * ) Notice: Subject to any disclaimer, the term of this patent is extended or adjusted under 35 U.S.C. 154(b) by 656 days.

(21) Appl. No.: 12/067,498

(22) PCT Filed: Sep. 20, 2006

(86) PCT No.: PCT/IL2006/001099
§ 371 (c)(1),
(2), (4) Date: Mar. 20, 2008

(87) PCT Pub. No.: WO2007/034480
PCT Pub. Date: Mar. 29, 2007

(65) Prior Publication Data
US 2008/0248020 A1 Oct. 9, 2008

Related U.S. Application Data

(60) Provisional application No. 60/718,354, filed on Sep. 20, 2005.

(51) Int. Cl.
*C12N 15/56* (2006.01)
*C12N 5/10* (2006.01)

(52) U.S. Cl. ............. 435/200; 435/254.2; 435/325; 435/183; 435/320.1; 424/94.6; 536/23.4

(58) Field of Classification Search ............... None
See application file for complete search history.

(56) References Cited

U.S. PATENT DOCUMENTS 5,968,822 A    10/1999  Pecker et al.
6,664,105 B1 * 12/2003  Pecker et al. .............. 435/320.1

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

* cited by examiner

*Primary Examiner* — Richard Hutson
(74) *Attorney, Agent, or Firm* — Browdy and Neimark, PLLC

(57) ABSTRACT

The invention relates to novel heparanases, heparanase splice variants, and to polynucleotides encoding them. Particularly, the invention relates to *Spalax* heparanases, and to *Spalax* and human heparanase splice variants. Heparanase splice variants can be used, for example, to modulate the activity of heparanase in diseases disorders or conditions caused by or associated with the enzymatic activity of heparanase. For instance, a splice variant capable of down regulating the activity of heparanase can be used to treat primary tumors and/or to prevent or treat metastasis.

6 Claims, 24 Drawing Sheets

```
AGATTTGGGCTGGCTCAAGTGACAAATAAGTGTTTTAAGGCAGATGGGGGTAGGGGGTAG        60
CCTAAAAGTTCAACCCAGGCTTTACTCCAGGGCCAGGAATCCGGTGCCTAGTGATGGGAC       120
CTAGAAGAGGGGCAGTGAGTGCAGGACATCAGGAAGCTAGGTCCCAGCCTCTGCGCAGTC       180
GGGGGCAGTCCCTCCCCAGGCCGCCCCGATCTTGGATCCCGGCCATCTCCGCACCCTTCA       240
GTTGGGTGTGGGTGATGACGTGACCGCCACCAAAGGGAAAGCTAACACGGAAATGGGAGA       300
GGGCGGGGAGGAGAGGCGCTGGGGGCAGGATGCAGGGGAGGAGTGGGAGGGATGGAGCGC       360
                                                  M  E  R            3
AGTGGGAGGTGCGGAGCCGGGAGGCGCTGGCTTGAGAGCCGGACTCGGAGCCCGGCGGGC       420
S  G  R  C  G  A  G  R  R  W  L  E  S  R  T  R  S  P  A  G          23
GGCAGCAGGGGCGCCAGCTCTCTGGGTCGCTGCCAGCCAGGTGAGCCCGAGATGCTGCGG       480
G  S  R  G  A  S  S  L  G  R  C  Q  P  G  E  P  E  M  L  R          43
CTGTCGCTGCTGCTGTGGCTCTGGGGGCCGCTCAGTCCCCTAGTCCAGTGCATCTTGGCC       540
L  S  L  L  L  W  L  W  G  P  L  S  P  L  V  Q  C  I  L  A          63
GCGCAGGCTGAAGATGTGGTAGAGCTGGAGTTCTCCACCCAGCGGCCGCTGCACCTGGTG       600
A  Q  A  E  D  V  V  E  L  E  F  S  T  Q  R  P  L  H  L  V          83
AGTCCCTCGTTCCTGTCCATCACCATCGACGCCAACCTGGCCACCGACCCGCGGTTCCTC       660
S  P  S  F  L  S  I  T  I  D  A  N  L  A  T  D  P  R  F  L         103
ACCTTCCTGGGTTCCCCAAAACTTCGGGCTTTGGCCAGAGGTTTGTCTCCTGCATACCTA       720
T  F  L  G  S  P  K  L  R  A  L  A  R  G  L  S  P  A  Y  L         123
AGATTTGGTGGCACCAAGACAGACTTCCTTATTTTTGACCCCAAGAAGGAACCAAGCCAT       780
R  F  G  G  T  K  T  D  F  L  I  F  D  P  K  K  E▲P  S  H          143
GAAGAAAGGAGTTACTGGAAATCTCAAGTGAACCATGATATTTGTAGATCTGGAGCCATC       840
E  E  R  S  Y  W  K  S  Q  V  N  H  D  I  C  R  S  G  A  I         163
CCTGCTGTTGTAGTGAGGAGACTACAGGTGGAATGGCCCTTCCAGGAGCAGTTGCTACTC       900
P  A  V  V  V  R  R  L  Q  V  E  W  P  F  Q  E  Q  L  L  L         183
AGAGAACAGTACCAAAAAGAGTTTAAAAACAGCACTTACTCACGAAGCTCAGTGGACATG       960
R  E  Q  Y  Q▲K  E  F  K  N̄  S  T  Y  S  R  S  S  V  D  M         203
CTGTACACGTTTGCTAGGTGCTCGGGATTGGACTTGATCTTTGGTCTAAATGCGTTACTA      1020
L  Y  T  F  A  R  C  S  G  L  D  L  I  F  G  L  N  A  L  L         223
AGAACTGCGGATTTTCGGTGGAACAGCTCCAATGCTCAGCTCCTGCTGAACTACTGCTCT      1080
R  T  A  D  F  R  W  N̄  S  S  N  A  Q  L  L  L  N  Y  C  S         243
TCCAAGAACTATGACATATCCTGGGAACTGGGCAATGAGCCTAATAGTTTTTGGAAGAAG      1140
S  K  N  Y  D  I  S  W  E  L  G  N  E* P  N  S  F  W  K  K         263
GCTCACATTTCCATCGATGGATTGCAGTTAGGAGAAGATTATATTGAGTTGCGTAAGCTT      1200
A  H  I  S  I  D  G  L  Q  L  G  E  D  Y  I  E  L  R  K  L         283
CTAAGAAAATCAACTCTCAAAAATGTGAAACTCTATGGTCCTGATGTTGGTCAACCTCGA      1260
L  R  K  S  T  L  K  N  V  K  L  Y  G  P  D  V  G  Q  P  R         303
GGAAAGACAGTTAAGTTGCTGAGAAGTTTCTTGAAGGCTGGCGGAGAAGTGATTGACTCA      1320
G  K  T  V  K  L  L  R  S  F  L  K  A  G  G  E  V  I  D  S         323
GTTACATGGCATCACTACTATTTGAATGGACGAATTGCTACCAAAGAAGATTTTTTAAGC      1380
V  T  W  H  H  Y  Y  L  N  G  R  I  A  T  K  E  D  F  L  S         343
CCTGATGTTCTGGACACTTTTATTTTATCTGTGCAAAAAATTCTACAGGTGGTTGAGGAG      1440
P  D  V  L  D  T  F  I  L  S  V  Q  K  I  L  Q  V  V  E  E         363
ACTAGACCTGGCAAGAAAGTCTGGCTGGAGAGACAAGCTCTGCATATGGCGGTGGAGCA       1500
T  R  P  G  K  K  V  W  L  G* T  S  S  A  Y  G  G  A              383
CCCTTGCTGTCCAACACCTTTGCAGCTGGCTTTATGTGGCTGGATAAAATTGGGCCTGTCA     1560
P  L  L  S  N  T  F  A  A  G  F  M  W  L  D  K  L  G  L  S         403
GCCCAAATGGGCATAGAAGTGGTGATGAGGCAAGTGTTCTTTGGAGCTGGAAACTACCAC      1620
A  Q  M  G  I  E  V  V  M  R  Q  V  F  F  G  A  G  N  Y  H         423
TTAGTGGATAAAAACTTCGAACCTTTACCTGATTATTGGCTGTCTCTTCTGTTCAAGAAA      1680
L  V  D  K  N  F  E  P  L  P  D  Y  W  L  S  L  L  F  K  K         443
CTGGTGGGTTCCAAGGTGTTAATGGCAAGAGTGAAAGGCCCAGACAGAAGCAAGCTTCGA     1740
L  V  G  S  K  V  L  M  A  R  V  K  G  P  D  R  S  K  L  R         463
GTGTACCTCCACTGCACAAACATCAATCACCCAAGGTATCAAGAAGGAGATTTAACTCTG      1800
V  Y  L  H  C  T  N  I  N  H  P  R  Y  Q  E  G  D  L  T  L         483
TACGCCTTAAACCTTTATAATGTCACCAAGCACTTGAAGTTACCTTATCAGTTATTTAAC     1860
Y  A  L  N  L  Y  N̄  V  T  K  H  L  K  L  P  Y  Q  L  F  N         503
AAACCAGTGGATAAGTACCTTGTAAAACCTTTGGGACCTGGTGGATTACTTTCCAAATCT     1920
K  P  V  D  K  Y  L  V  K  P  L  G  P  G  G  L  L  S  K  S         523
GTCCAACTCAATGGTCAAGCCTTGAAGATGGTGGATGATCAAACCCTGCCAGCTTTGACA     1980
V  Q  L  N  G  Q  A  L  K  M  V  D  D  Q  T  L  P  A  L  T         543
GAAAAGCCTCTCGGCCCAGGAAGTTCACTAGGCTTGCCTGCCTTTTCATATGGGTTTTTT     2040
E  K  P  L  G  P  G  S  S  L  G  L  P  A  F  S  Y  G  F  F         563
GTCATAAGAAATGCCAAAGTTGCTGCTTGTCTATGAAAATAAAAGGCAAGACAGTTGCCA     3000
V  I  R  N  A  K  V  A  A  C  L                                    574
TAAAAAAAAAAAAAACCTATAGTGAGTCGTATTAATTCTGTGCTCGC                    3045
```

Fig. 1

```
Spalax    .......MLRLSLLLWLWGPLSPLVQCIL..AAQAEDVVELEFSTQRPLH   81
                 |:| | ||| ||    |     |||:|||:|:| || |||
human     MLLRSKPALPPPLMLLLLGPLGPLSPGALPRPAQAQDVVDLDFFTQEPLH   50

Spalax    LVSPSFLSITIDANLATDPRFLTFLGSPKLRALARGLSPAYLRFGGTKTD   131
          ||||||||:||||||||||||||  |||||||  ||||||||||||||||
human     LVSPSFLSVTIDANLATDPRFLILLGSPKLRTLARGLSPAYLRFGGTKTD   100

Spalax    FLIFDPKKEPSHEERSYWKSQVNHDICRSGAIPAVVVRRLQVEWPFQEQL   181
          |||||||||  ||||||·||||||·||||  |:  |·||   :|··|||:||||
human     FLIFDPKKESTFEERSYWQSQVNQDICKYGSIPPDVEEKLRLEWPYQEQL   150

Spalax    LLREQYQKEFKNSTYSRSSVDMLYTFARCSGLDLIFGLNALLRTADFRWN   231
          ||||  |||·|||||||||||||·||||| |||||||||||||||||| ·||
human     LLREHYQKKFKNSTYSRSSVDVLYTFANCSGLDLIFGLNALLRTADLQWN   200
                                                         *
Spalax    SSNAQLLLNYCSSKNYDISWELGNEPNSFWKKAHISIDGLQLGEDYIELR   281
          ||||||||·|||||  |.|||||||||||||·||| | |·| ||||||:|:|
human     SSNAQLLLDYCSSKGYNISWELGNEPNSFLKKADIFINGSQLGEDFIQLH   250

Spalax    KLLRKSTLKNVKLYGPDVGQPRGKTVKLLRSFLKAGGEVIDSVTWHHYYL   331
          ||||||| || |||||||||||| ||  |:|:|||||||||||||||||||
human     KLLRKSTFKNAKLYGPDVGQPRRKTAKMLKSFLKAGGEVIDSVTWHHYYL   300
                                                *
Spalax    NGRIATKEDFLSPDVLDTFILSVQKILQVVEETRPGKKVWLGETSSAYGG   381
          ||| ||:||||·||||| ||||:  ||||·||||||||||||||||||||
human     NGRTATREDFLNPDVLDIFISSVQKVFQVVESTRPGKKVWLGETSSAYGG   350

Spalax    GAPLLSNTFAAGFMWLDKLGLSAQMGIEVVMRQVFFGAGNYHLVDKNFEP   431
          ||||||·|||||||||||||||·||||||||||||||||||||||·||:|
human     GAPLLSDTFAAGFMWLDKLGLSARMGIEVVMRQVFFGAGNYHLVDENFDP   400

Spalax    LPDYWLSLLFKKLVGSKVLMARVKGPDRSKLRVYLHCTNINHPRYQEGDL   481
          ||||||||||||||| ||||| ·|  || |||||||||||  |||·||||
human     LPDYWLSLLFKKLVGTKVLMASVQGSKRRKLRVYLHCTNTDNPRYKEGDL   450

Spalax    TLYALNLYNVTKHLKLPYQLFNKPVDKYLVKPLGPGGLLSKSVQLNGQAL   531
          ||||:||:|||:|:|||  || ||||·:||| ||||||||||||| |
human     TLYAINLHNVTKYLRLPYPFSNKQVDKYLLRPLGPHGLLSKSVQLNGLTL   500

Spalax    KMVDDQTLPALTEKPLGPGSSLGLPAFSYGFFVIRNAKVAACL          575
          |||||||| | |||| ||||||||||||| ||||||||||||:
human     KMVDDQTLPPLMEKPLRPGSSLGLPAFSYSFFVIRNAKVAACI          543
```

```
1    TCAGATTTGG GCTGGCTCAA GTGACAAATA AGTGTTTTAA GGCAGATGGG
          5'UTRf(m,h) 62c
51   GGTAGGGGGT AGCCTAAAAG TTCAACCCAG GCTTTACTCC AGGGCCAGGA

101  ATCCGGTGCC TAGTGATGGG ACCTAGAAGA GGGGCAGTGA GTGCAGGACA

151  TCAGGAAGCT AGGTCCCAGC CTCTGCGCAG TCGGGGCAG TCCCTCCCCA

201  GGCCGCCCCG ATCTTGGATC CCGGCCATCT CCGCACCCTT CAGTTGGGTG

251  TGGGTGATGA CGTGACCGCC ACCAAAGGGA AAGCTAACAC GGAAATGGGA

301  GAGGGCGGGG AGGAGAGGCG CTGGGGGCAG GATGCAGGGG AGGAGTGGGA

351  GGGATGGAGC GCAGTGGGAG GTGCGGAGCC GGGAGGCGCT GGCTTGAGAG
          sATG1f 62C
401  CCGGACTCGG AGCCCGGCGG GCGGCAGCAG GGGCGCCAGC TCTCTGGGTC

451  GCTGCCAGCC AGGTGAGCCC GAGATGCTGC GGCTGTCGCT GCTGCTGTGG
                              sATG2F 66c
501  CTCTGGGGGC CGCTCAGTCC CCTAGTCCAG TGCATCTTGG CCGCGCAGGC

551  TGAAGATGTG GTAGAGCTGG AGTTCTCCAC CCAGCGGCCG CTGCACCTGG

601  TGAGTCCCTC GTTCCTGTCC ATCACCATCG ACGCCAACCT GGCCACCGAC
             M4f 61c
651  CCGCGGTTCC TCACCTTCCT GGG↑TTCCCCA AAACTTCGGG CTTTGGCCAG
                  sM5b 60c
701  AGGTTTGTCT CCTGCATACC TAAGATTTGG TGGCACCAAG ACAGACTTCC

751  TTATTTTTGA CCCCAAGAAG GAACCAAGCC ATGAAGAAAG GAGTTACTGG
                                                146 bp(exon 3)
801  AAATCTCAAG TGAACCATG↑A TATTTGTAGA TCTGGAGCCA TCCTGCTGT 851  TGTAGTGAGG AGACTACAGG TGGAATGGCC CTTCCAGGAG CAGTTGCTAC
                                                126 bp (exon 4)
901  TCAGAGAACA GTACCAAAAA GAGTTTAAAA ACAGCACTTA CTCAC↑GAAGC
          sM8b 57c                              M1f 55c
951  TCAGTGGACA TGCTGTACAC GTTTGCTAGG TGCTCGGGAT TGGACTTGAT
          sM9b 59c
1001 CTTTGGTCTA AATGCGTTAC TAAGAACTGC GGATTTTCGG TGGAACAGCT
                                                174 bp (exon 5)
```

Fig. 6G

```
1051  CCAATGCTCA GCTCCTGCTG AACTACTGCT CTTCCAAGAA CTATGACATA
                                                  sM2F 59c
1101  TCCTGGGAAC TGGGCAATG↑A GCCTAATAGT TTTTGGAAGA AGGCTCACAT

1151  TTCCATCGAT GGATTGCAGT TAGGAGAAGA TTATATTGAG TTGCGTAAGC
                                                  169 bp (exon 6)
1201  TTCTAAGAAA ATCAACTCTC AAAAATGTGA AACTCTATGG TCCTGATGTT 1251  GGTCAACCTC GAGGAAAGAC AGTTAAGTTG CTGAGAAG↑TT TCTTGAAGGC
           Mf/b 64c(sMf/b 60c)       M7b 55.5c
Deletion(s60) 1301  TGGCGGAGAA GTGATTGACT CAGTTACATG GCATCA↑CTAC TATTTGAATG
                       sM3b/F 61c                            174 exon7
1351  GACGAATTGC TACCAAAGAA GATTTTTTAA GCCCTGATGT TCTGGACACT
                                                  94 bp exon 8
1401  TTTATTTTAT CTGTGCAAAA AATTCTACAG↑ GTGGTTGAGG AGACTAGACC 1451  TGGCAAGAAA GTCTGGCTGG GAGAGACAAG CTCTGCATAT GGCGGTGGAG
                                                  107 bp exon 9
1501  CACCCTTGCT GTCCAACACC TTTGCAGCTG GCTTTAT↑GTG GCTGGATAAA
                      M2b 58c        srmhHep1529f 55c
1551  TTGGGCCTGT CAGCCCAAAT GGGCATAGAA GTGGTGATGA GGCAAGTGTT 1601  CTTTGGAGCT GGAAACTACC ACTTAGTGGA TAAAAACTTC GAACCTTTAC
                                                  115 bp exon 10
1651  CT↑GATTATTG GCTGTCTCTT CTGTTCAAGA AACTGGTGGG TTCCAAGGTG
                                                  119 bp exon 11
1701  TTAATGGCAA GAGTGAAAGG CCCAGACAGA AGCAAGCTTC GAGTGTACCT
                                                  sHep1742f 57.8c
1751  CCACTGCACA AACATCAATC A↑CCCAAGGTA TCAAGAAGGA GATTTAACTC 1801  TGTACGCCTT AAACCTTTAT AATGTCACCA AGCACTTGAA GTTACCTTAT
                                                  147 bp exon 12
1851  CAGTTATTTA ACAAACCAGT GGATAAGTAC CTTGTAAAAC CTTTGGGACC

1901  TGGTGGATTA CTTTCCAA↑AT CTGTCCAACT CAATGGTCAA GCCTTGAAGA

1951  TGGTGGATGA TCAAACCCTG CCAGCTTTGA CAGAAAAGCC TCTCGGCCCA

2001  GGAAGTTCAC TAGGCTTGCC TGCCTTTTCA TATGGGTTTT TTGTCATAAG
```

Fig. 6G – cont. 1

```
2051    AAATGCCAAA GTCGCAGCTT GCATATGA
                    3'b 60C
GAAATGCCAAA GTTGCTGCTT GTCTATGA
           sHep3'b54c
GAAATGCCAAA GTTGCTGCTT GTCTATGA
            sHep 3'Lb 62c
             GAAATGCCAAA GTTGCTGCTT GCATCTGA
```

Fig. 6G – cont. 2

```
  1  aggagaaaag ggcgctgggg ctcggcggga ggaagtgcta gagctctcga 51  ctctccgctg cgcggcagct ggcgggggga gcagccaggt gagcccaaga 101  tgctgctgcg ctcgaagcct cgctgccgc cgccgctgat gctgctgctc 151  ctggggccgc tgggtcccct ctccctggc gcctgcccc gacctgcgca 201  agcacaggac gtcgtggacc tggacttctt cacccaggag ccgctgcacc 251  tggtgagccc ctcgttcctg tccgtcacca ttgacgccaa cctggccacg
                     hM4f
301  gacccgcggt tcctcatcct cctggg ttct ccaaagcttc gtaccttggc
                                 sM5b(3)
351  cagaggcttg tctcctgcgt acctgaggtt tggtggcacc aagacagact
          hM45f 61.5C         E S            146bp (exon3)
401  tcctaatttt cgatcccaag aaggaa tcaa cctttgaaga gagaagttac 451  tggcaatctc aagtcaacca gg atatttgc aaatatggat ccatccctcc
                                            126bp:3=42 (exon4)
501  tgatgtggag gagaagttac ggttggaatg ccctaccag gagcaattgc
                                                    Q K
551  tactccgaga acactaccag aaaaagttca gaacagcac ctactcaa ga
         sM8b(3)
601  agctctgtag atgtgctata cacttttgca aactgctcag gactggactt
                                           174bp:3=58 (exon5)
651  gatctttggc ctaaatgcgt tattaagaac agcagatttg cagtggaaca 701  gttctaatgc tcagttgctc ctggactact gctcttccaa ggggtataac
             hM9b 58.7c
751  atttcttggg aactaggcaa tg aacctaac agtttccttt a agaaggctga 801  tattttcatc aatgggtcgc agttaggaga agattttatt caattgcata
                                                   169bp (exon6)
851  aacttctaag aaagtccacc ttcaaaaatg caaaactcta tggtcctgat 901  gttggtcagc ctcgaagaaa gacggctaag atgctgaaga g cttcctgaa
         hMb/f                          48:3=16 (exon7)
951  ggctggtgga gaagtgattg attcagttac atggcatca c tactatttga
                                                   94bp (exon8)
1001 atggacggac tgctaccagg gaagattttc taaaccctga tgtattggac 1051 attttttattt catctgtgca aaaagtttc cag gtggttg agagcaccag
                                           107bp (exon 9)
1101 gcctggcaag aaggtctggt taggagaaac aagctctgca tatggaggcg 1151 gagcgccctt gctatccgac acctttgcag ctggctttat gtggctggat
                              hM2b                h1529f
1201 aaattgggcc tgtcagcccg aatgggaata gaagtggtga tgaggcaagt
                                                   115bp (exon 10)
1251 attctttgga gcaggaaact accatttagt ggatgaaaac ttcgatcctt 1301 tacct gatta ttggctatct cttctgttca agaaattggt gggcaccaag
                                                   119bp (exon11)
```

Fig. 6H

```
1351  gtgttaatgg caagcgtgca aggttcaaag agaaggaagc ttcgagtata 1401  ccttcattgc acaaacactg acaattccaag gtataaagaa ggagatttaa 1451  ctctgtatgc cataaacctc cataacgtca ccaagtactt gcggttaccc
                                               147bp:3=49 (exo12)
1501  tatccttttt ctaacaagca agtggataaa taccttctaa gacctttggg 1551  acctcatgga ttactttcca atatctgtcca actcaatggt ctaactctaa 1601  agatggtgga tgatcaaacc ttgccacctt taatggaaaa acctctccgg 1651  ccaggaagtt cactgggctt gccagctttc tcatatagtt ttttgtgat 1701  aagaaatgcc aaagttgctg cttgcatctg aaaataaaat atactagtcc
              rhHep3`b
1751  tgacactg
```

Fig. 6H – cont.

SEQUENCE LISTING

<160> NUMBER OF SEQ ID NOS: 72

<210> SEQ ID NO 1
<211> LENGTH: 574
<212> TYPE: PRT
<213> ORGANISM: mammalian

<400> SEQUENCE: 1

```
Met Glu Arg Ser Gly Arg Cys Gly Ala Gly Arg Arg Trp Leu Glu Ser
1               5                   10                  15
```

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
            35                  40                  45

Trp Leu Trp Gly Pro Leu Ser Pro Leu Val Gln Cys Ile Leu Ala Ala
 50                  55                  60

Gln Ala Glu Asp Val Val Glu Leu Glu Phe Ser Thr Gln Arg Pro Leu
 65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
            115                 120                 125

Lys Thr Asp Phe Leu Ile Phe Asp Pro Lys Lys Glu Pro Ser His Glu
            130                 135                 140

Glu Arg Ser Tyr Trp Lys Ser Gln Val Asn His Asp Ile Cys Arg Ser
145                 150                 155                 160

Gly Ala Ile Pro Ala Val Val Arg Leu Gln Val Glu Trp Pro
            165                 170                 175

Phe Gln Glu Gln Leu Leu Leu Arg Glu Gln Tyr Gln Lys Glu Phe Lys
            180                 185                 190

Asn Ser Thr Tyr Ser Arg Ser Ser Val Asp Met Leu Tyr Thr Phe Ala
            195                 200                 205

Arg Cys Ser Gly Leu Asp Leu Ile Phe Gly Leu Asn Ala Leu Leu Arg
            210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
            245                 250                 255

Pro Asn Ser Phe Trp Lys Lys Ala His Ile Ser Ile Asp Gly Leu Gln
            260                 265                 270

Leu Gly Glu Asp Tyr Ile Glu Leu Arg Lys Leu Leu Arg Lys Ser Thr
            275                 280                 285

Leu Lys Asn Val Lys Leu Tyr Gly Pro Asp Val Gly Gln Pro Arg Gly
            290                 295                 300

Lys Thr Val Lys Leu Leu Arg Ser Phe Leu Lys Ala Gly Gly Glu Val
305                 310                 315                 320

Ile Asp Ser Val Thr Trp His His Tyr Tyr Leu Asn Gly Arg Ile Ala
                325                 330                 335

Thr Lys Glu Asp Phe Leu Ser Pro Asp Val Leu Asp Thr Phe Ile Leu
            340                 345                 350

Ser Val Gln Lys Ile Leu Gln Val Val Glu Glu Thr Arg Pro Gly Lys
            355                 360                 365

Lys Val Trp Leu Gly Glu Thr Ser Ser Ala Tyr Gly Gly Gly Ala Pro
            370                 375                 380

Leu Leu Ser Asn Thr Phe Ala Ala Gly Phe Met Trp Leu Asp Lys Leu
385                 390                 395                 400

Gly Leu Ser Ala Gln Met Gly Ile Glu Val Val Met Arg Gln Val Phe
            405                 410                 415

Phe Gly Ala Gly Asn Tyr His Leu Val Asp Lys Asn Phe Glu Pro Leu
            420                 425                 430

Pro Asp Tyr Trp Leu Ser Leu Leu Phe Lys Lys Leu Val Gly Ser Lys

```
                435                 440                 445
Val Leu Met Ala Arg Val Lys Gly Pro Asp Arg Ser Lys Leu Arg Val
    450                 455                 460

Tyr Leu His Cys Thr Asn Ile Asn His Pro Arg Tyr Gln Glu Gly Asp
465                 470                 475                 480

Leu Thr Leu Tyr Ala Leu Asn Leu Tyr Asn Val Thr Lys His Leu Lys
                485                 490                 495

Leu Pro Tyr Gln Leu Phe Asn Lys Pro Val Asp Lys Tyr Leu Val Lys
                500                 505                 510

Pro Leu Gly Pro Gly Leu Leu Ser Lys Ser Val Gln Leu Asn Gly
            515                 520                 525

Gln Ala Leu Lys Met Val Asp Asp Gln Thr Leu Pro Ala Leu Thr Glu
        530                 535                 540

Lys Pro Leu Gly Pro Gly Ser Ser Leu Gly Leu Pro Ala Phe Ser Tyr
545                 550                 555                 560

Gly Phe Phe Val Ile Arg Asn Ala Lys Val Ala Ala Cys Leu
                565                 570

<210> SEQ ID NO 2
<211> LENGTH: 2078
<212> TYPE: DNA
<213> ORGANISM: mammalian

<400> SEQUENCE: 2
tcagatttgg gctggctcaa gtgacaaata agtgttttaa ggcagatggg ggtagggggt      60
agcctaaaag ttcaacccag gctttactcc agggccagga atccggtgcc tagtgatggg    120
acctagaaga ggggcagtga gtgcaggaca tcaggaagct aggtcccagc ctctgcgcag    180 tcggggcag tccctcccca ggccgccccg atcttggatc ccggccatct ccgcacccctt    240 cagttgggtg tgggtgatga cgtgaccgcc accaaaggga aagctaacac ggaaatggga    300
gagggcgggg aggagaggcg ctgggggcag gatgcagggg aggagtggga gggatggagc    360
gcagtgggag gtgcggagcc gggaggcgct ggcttgagag ccggactcgg agcccggcgg    420
gcggcagcag gggcgccagc tctctgggtc gctgccagcc aggtgagccc gagatgctgc    480
ggctgtcgct gctgctgtgg ctctgggggc cgctcagtcc cctagtccag tgcatcttgg    540
ccgcgcaggc tgaagatgtg gtagagctgg agttctccac ccagcggccg ctgcacctgg    600
tgagtccctc gttcctgtcc atcaccatcg acgccaacct ggccaccgac ccgcggttcc    660
tcaccttcct gggttcccca aaacttcggg ctttggccag aggtttgtct cctgcatacc    720
taagatttgg tggcaccaag acagacttcc ttatttttga ccccaagaag gaaccaagcc    780
atgaagaaag gagttactgg aaatctcaag tgaaccatga tatttgtaga tctggagcca    840
tccctgctgt tgtagtgagg agactacagg tggaatggcc cttccaggag cagttgctac    900
tcagagaaca gtaccaaaaa gagtttaaaa acagcactta ctcacgaagc tcagtggaca    960
tgctgtacac gtttgctagg tgctcgggat tggacttgat ctttggtcta aatgcgttac   1020
taagaactgc ggattttcgg tggaacagct ccaatgctca gctcctgctg aactactgct   1080
cttccaagaa ctatgacata tcctgggaac tgggcaatga gcctaatagt ttttggaaga   1140
aggctcacat ttccatcgat ggattgcagt taggagaaga ttatattgag ttgcgtaagc   1200
ttctaagaaa atcaactctc aaaaatgtga aactctatgg tcctgatgtt ggtcaacctc   1260
gaggaaagac agttaagttg ctgagaagtt tcttgaaggc tggcgagaa gtgattgact   1320 cagttacatg gcatcactac tatttgaatg gacgaattgc taccaaagaa gatttttaa    1380
```

```
gccctgatgt tctggacact tttattttat ctgtgcaaaa aattctacag gtggttgagg    1440
agactagacc tggcaagaaa gtctggctgg gagagacaag ctctgcatat ggcggtggag    1500 caccccttgct gtccaacacc tttgcagctg gctttatgtg gctggataaa ttgggcctgt   1560
cagcccaaat gggcatagaa gtggtgatga ggcaagtgtt ctttggagct ggaaactacc    1620
acttagtgga taaaaacttc gaacctttac ctgattattg gctgtctctt ctgttcaaga    1680
aactggtggg ttccaaggtg ttaatggcaa gagtgaaagg cccagacaga agcaagcttc    1740
gagtgtacct ccactgcaca aacatcaatc acccaaggta tcaagaagga gatttaactc    1800
tgtacgcctt aaacctttat aatgtcacca agcacttgaa gttacctat cagttattta     1860 acaaaccagt ggataagtac cttgtaaaac ctttgggacc tggtggatta cttcccaaat    1920
ctgtccaact caatggtcaa gccttgaaga tggtggatga tcaaaccctg ccagctttga    1980
cagaaaagcc tctcggccca ggaagttcac taggcttgcc tgccttttca tatgggtttt    2040
ttgtcataag aaatgccaaa gttgctgctt gtctatga                            2078
```

<210> SEQ ID NO 3
<211> LENGTH: 532
<212> TYPE: PRT
<213> ORGANISM: mammalian

<400> SEQUENCE: 3

```
Met Glu Arg Ser Gly Arg Cys Gly Ala Gly Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Lys Glu Pro Ser His Glu
    130                 135                 140

Glu Arg Ser Tyr Trp Lys Ser Gln Val Asn His Gly Ser Ser Val Asp
145                 150                 155                 160

Met Leu Tyr Thr Phe Ala Arg Cys Ser Gly Leu Asp Leu Ile Phe Gly
                165                 170                 175

Leu Asn Ala Leu Leu Arg Thr Ala Asp Phe Arg Trp Asn Ser Ser Asn
            180                 185                 190

Ala Gln Leu Leu Leu Asn Tyr Cys Ser Ser Lys Asn Tyr Asp Ile Ser
        195                 200                 205

Trp Glu Leu Gly Asn Glu Pro Asn Ser Phe Trp Lys Lys Ala His Ile
    210                 215                 220

Ser Ile Asp Gly Leu Gln Leu Gly Glu Asp Tyr Ile Glu Leu Arg Lys
225                 230                 235                 240

Leu Leu Arg Lys Ser Thr Leu Leu Asn Val Lys Leu Tyr Gly Pro Asp
                245                 250                 255
```

-continued

| | | | | | | | | | | | | |
|---|---|---|---|---|---|---|---|---|---|---|---|---|
|Val|Gly|Gln|Pro 260|Arg|Gly|Lys|Thr|Val 265|Lys|Leu|Leu|Arg|Ser|Phe 270|Leu|
|Lys|Ala|Gly|Gly 275|Glu|Val|Ile|Asp 280|Ser|Val|Thr|Trp 285|His|His|Tyr|Tyr|
|Leu|Asn|Gly 290|Arg|Ile|Ala|Thr|Lys 295|Glu|Asp|Phe|Leu 300|Ser|Pro|Asp|Val|
|Leu|Asp 305|Thr|Phe|Ile|Leu 310|Ser|Val|Gln|Lys 315|Ile|Leu|Gln|Val 320|Val|Glu|
|Glu|Thr|Arg|Pro|Gly 325|Lys|Lys|Val|Trp|Leu 330|Gly|Glu|Thr|Ser 335|Ser|Ala|
|Tyr|Gly|Gly|Gly 340|Ala|Pro|Leu|Leu|Ser 345|Asn|Thr|Phe|Ala 350|Ala|Gly|Phe|
|Met|Trp|Leu|Asp 355|Lys|Leu|Gly|Leu 360|Ser|Ala|Gln|Met 365|Gly|Ile|Glu|Val|
|Val|Met 370|Arg|Gln|Val|Phe 375|Phe|Gly|Ala|Gly|Asn 380|Tyr|His|Leu|Val|Asp|
|Lys|Asn 385|Phe|Glu|Pro|Leu 390|Pro|Asp|Tyr|Trp 395|Leu|Ser|Leu|Leu|Phe 400|Lys|
|Lys|Leu|Val|Gly|Ser 405|Lys|Val|Leu|Met|Ala 410|Arg|Val|Lys|Gly 415|Pro|Asp|
|Arg|Ser|Lys|Leu 420|Arg|Val|Tyr|Leu|His 425|Cys|Thr|Asn|Ile 430|Asn|His|Pro|
|Arg|Tyr|Gln 435|Glu|Gly|Asp|Leu|Thr 440|Leu|Tyr|Ala|Leu 445|Asn|Leu|Tyr|Asn|
|Val|Thr 450|Lys|His|Leu|Lys 455|Leu|Pro|Tyr|Gln|Leu 460|Phe|Asn|Lys|Pro|Val|
|Asp 465|Lys|Tyr|Leu|Val 470|Lys|Pro|Leu|Gly|Pro 475|Gly|Gly|Leu|Leu|Ser 480|Lys|
|Ser|Val|Gln|Leu 485|Asn|Gly|Gln|Ala|Leu 490|Lys|Met|Val|Asp|Asp 495|Gln|Thr|
|Leu|Pro|Ala|Leu 500|Thr|Glu|Lys|Pro 505|Leu|Gly|Pro|Gly|Ser 510|Ser|Leu|Gly|
|Leu|Pro|Ala 515|Phe|Ser|Tyr|Gly|Phe 520|Phe|Val|Ile|Arg 525|Asn|Ala|Lys|Val|
|Ala|Ala|Cys|Ile 530|

```
<210> SEQ ID NO 4
<211> LENGTH: 1952
<212> TYPE: DNA
<213> ORGANISM: mammalian

<400> SEQUENCE: 4
tcagatttgg gctggctcaa gtgacaaata agtgttttaa ggcagatggg ggtagggggt      60
agcctaaaag ttcaacccag gctttactcc agggccagga atccggtgcc tagtgatggg     120
acctagaaga ggggcagtga gtgcaggaca tcaggaagct aggtcccagc ctctgcgcag     180
tcgggggcag tccctcccca ggccgccccg atcttggatc ccggccatct ccgcacccctt    240 cagttgggtg tgggtgatga cgtgaccgcc accaaaggga aagctaacac ggaaatggga    300
gagggcgggg aggagaggcg ctgggggcag gatgcagggg aggagtggga gggatgggagc   360 gcagtgggag gtgcggagcc gggaggcgct ggcttgagag ccggactcgg agcccggcgg    420
gcggcagcag gggcgccagc tctctgggtc gctgccagcc aggtgagccc gagatgctgc    480
ggctgtcgct gctgctgtgg ctctgggggc cgctcagtcc cctagtccag tgcatcttgg    540
```

```
ccgcgcaggc tgaagatgtg gtagagctgg agttctccac ccagcggccg ctgcacctgg      600
tgagtccctc gttcctgtcc atcaccatcg acgccaacct ggccaccgac ccgcggttcc      660
tcaccttcct gggttcccca aaacttcggg ctttggccag aggtttgtct cctgcatacc      720
taagatttgg tggcaccaag acagacttcc ttattttga ccccaagaag gaaccaagcc      780
atgaagaaag gagttactgg aaatctcaag tgaaccatgg aagctcagtg acatgctgt       840 acacgtttgc taggtgctcg ggattggact tgatctttgg tctaaatgcg ttactaagaa      900
ctgcggattt tcggtggaac agctccaatg ctcagctcct gctgaactac tgctcttcca      960
agaactatga catatcctgg gaactgggca atgagcctaa tagttttgg aagaaggctc      1020 acatttccat cgatggattg cagttaggag aagattatat tgagttgcgt aagcttctaa      1080
gaaaatcaac tctcaaaaat gtgaaactct atggtcctga tgttggtcaa cctcgaggaa      1140
agacagttaa gttgctgaga gtttcttga aggctggcgg agaagtgatt gactcagtta       1200
catggcatca ctactatttg aatggacgaa ttgctaccaa agaagatttt ttaagccctg      1260
atgttctgga cactttttatt ttatctgtgc aaaaaattct acaggtggtt gaggagacta      1320
gacctggcaa gaaagtctgg ctgggagaga caagctctgc atatggcggt ggagcacct       1380 tgctgtccaa caccttcca gctggcttta tgtggctgga taaattgggc ctgtcagccc       1440
aaatgggcat agaagtggtg atgaggcaag tgttctttgg agctgaaaac taccacttag      1500
tggataaaaa cttcgaacct ttacctgatt attggctgtc tcttctgttc aagaaactgg      1560
tgggttccaa ggtgttaatg gcaagagtga aggcccaga cagaagcaag cttcgagtgt       1620
acctccactg cacaaacatc aatcacccaa ggtatcaaga aggagattta actctgtacg      1680 ccttaaaacct ttataatgtc accaagcact tgaagttacc ttatcagtta tttaacaaac      1740
cagtggataa gtaccttgta aaacctttgg gacctggtgg attactttcc aaatctgtcc      1800
aactcaatgg tcaagccttg aagatggtgg atgatcaaac cctgccagct ttgacagaaa      1860
agcctctcgg cccaggaagt tcactaggct tgcctgcctt tcatatggg ttttttgtca       1920 taagaaatgc caaagtcgca gcttgcatat ga                                    1952
```

<210> SEQ ID NO 5
<211> LENGTH: 516
<212> TYPE: PRT
<213> ORGANISM: mammalian

<400> SEQUENCE: 5

```
Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125
```

```
Lys Thr Asp Phe Leu Ile Phe Asp Pro Lys Lys Glu Pro Ser His Glu
130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
            165                 170                 175

Phe Gln Glu Gln Leu Leu Leu Arg Glu Gln Tyr Gln Lys Glu Phe Lys
                180                 185                 190

Asn Ser Thr Tyr Ser Gln Pro Asn Ser Phe Trp Lys Lys Ala His Ile
        195                 200                 205

Ser Ile Asp Gly Leu Gln Leu Gly Glu Asp Tyr Ile Glu Leu Arg Lys
210                 215                 220

Leu Leu Arg Lys Ser Thr Leu Lys Asn Val Lys Leu Tyr Gly Pro Asp
225                 230                 235                 240

Val Gly Gln Pro Arg Gly Lys Thr Val Lys Leu Leu Arg Ser Phe Leu
                245                 250                 255

Lys Ala Gly Gly Glu Val Ile Asp Ser Val Thr Trp His His Tyr Tyr
            260                 265                 270

Leu Asn Gly Arg Ile Ala Thr Lys Glu Asp Phe Leu Ser Pro Asp Val
        275                 280                 285

Leu Asp Thr Phe Ile Leu Ser Val Gln Lys Ile Leu Gln Val Val Glu
290                 295                 300

Glu Thr Arg Pro Gly Lys Lys Val Trp Leu Gly Glu Thr Ser Ser Ala
305                 310                 315                 320

Tyr Gly Gly Gly Ala Pro Leu Leu Ser Asn Thr Phe Ala Ala Gly Phe
                325                 330                 335

Met Trp Leu Asp Lys Leu Gly Leu Ser Ala Gln Met Gly Ile Glu Val
            340                 345                 350

Val Met Arg Gln Val Phe Phe Gly Ala Gly Asn Tyr His Leu Val Asp
        355                 360                 365

Lys Asn Phe Glu Pro Leu Pro Asp Tyr Trp Leu Ser Leu Leu Phe Lys
370                 375                 380

Lys Leu Val Gly Ser Lys Val Leu Met Ala Arg Val Lys Gly Pro Asp
385                 390                 395                 400

Arg Ser Lys Leu Arg Val Tyr Leu His Cys Thr Asn Ile Asn His Pro
                405                 410                 415

Arg Tyr Gln Glu Gly Asp Leu Thr Leu Tyr Ala Leu Asn Leu Tyr Asn
            420                 425                 430

Val Thr Lys His Leu Lys Leu Pro Tyr Gln Leu Phe Asn Lys Pro Val
        435                 440                 445

Asp Lys Tyr Leu Val Lys Pro Leu Gly Pro Gly Gly Leu Leu Ser Lys
450                 455                 460

Ser Val Gln Leu Asn Gly Gln Ala Leu Lys Met Val Asp Asp Gln Thr
465                 470                 475                 480

Leu Pro Ala Leu Thr Glu Lys Pro Leu Gly Pro Gly Ser Ser Leu Gly
                485                 490                 495

Leu Pro Ala Phe Ser Tyr Gly Phe Val Ile Arg Asn Ala Lys Val
            500                 505                 510

Ala Ala Cys Ile
        515

<210> SEQ ID NO 6
<211> LENGTH: 1904
<212> TYPE: DNA
<213> ORGANISM: mammalian
```

<400> SEQUENCE: 6

```
tcagatttgg gctggctcaa gtgacaaata agtgttttaa ggcagatggg ggtaggggt      60
agcctaaaag ttcaacccag gctttactcc agggccagga atccggtgcc tagtgatggg    120
acctagaaga ggggcagtga gtgcaggaca tcaggaagct aggtcccagc ctctgcgcag    180
tcggggcag tccctcccca ggccgccccg atcttggatc ccggccatct ccgcaccctt    240
cagttgggtg tgggtgatga cgtgaccgcc accaaaggga aagctaacac ggaaatggga    300
gagggcgggg aggagaggcg ctgggggcag gatgcagggg aggagtggga gggatggagc    360
gcagtgggag gtgcggagcc gggaggcgct ggcttgagag ccggactcgg agcccggcgg    420
gcggcagcag gggcgccagc tctctgggtc gctgccagcc aggtgagccc gagatgctgc    480
ggctgtcgct gctgctgtgg ctctgggggc cgctcagtcc cctagtccag tgcatcttgg    540
ccgcgcaggc tgaagatgtg gtagagctgg agttctccac ccagcggccg ctgcacctgg    600
tgagtccctc gttcctgtcc atcaccatcg acgccaacct ggccaccgac ccgcggttcc    660
tcaccttcct gggttcccca aaacttcggg ctttggccag aggtttgtct cctgcatacc    720
taagatttgg tggcaccaag acagacttcc ttattttga ccccaagaag gaaccaagcc    780
atgaagaaag gagttactgg aaatctcaag tgaaccatga tatttgtaga tctggagcca    840
tccctgctgt tgtagtgagg agactacagg tggaatggcc cttccaggag cagttgctac    900
tcagagaaca gtaccaaaaa gagtttaaaa acagcactta ctcacagcct aatagttttt    960
ggaagaaggc tcacatttcc atcgatggat tgcagttagg agaagattat attgagttgc   1020
gtaagcttct aagaaaatca actctcaaaa atgtgaaact ctatggtcct gatgttggtc   1080
aacctcgagg aaagacagtt aagttgctga agtttcttt gaaggctggc ggagaagtga   1140
ttgactcagt tacatggcat cactactatt tgaatggacg aattgctacc aagaagatt   1200
ttttaagccc tgatgttctg gacactttta ttttatctgt gcaaaaaatt ctacaggtgg   1260
ttgaggagac tagacctggc aagaaagtct ggctgggaga gacaagctct gcatatggcg   1320
gtggagcacc cttgctgtcc aacacctttg cagctggctt tatgtggctg ataaattgg   1380
gcctgtcagc ccaaatgggc atagaagtgg tgatgaggca agtgttcttt ggagctggaa   1440
actaccactt agtggataaa aacttcgaac ctttacctga ttattggctg tctcttctgt   1500
tcaagaaact ggtgggttcc aaggtgttaa tggcaagagt gaaaggccca gacagaagca   1560
agcttcgagt gtacctccac tgcacaaaca tcaatcaccc aaggtatcaa gaaggagatt   1620
taactctgta cgccttaaac ctttataatg tcaccaagca cttgaagtta ccttatcagt   1680
tatttaacaa accagtggat aagtaccttg taaaacctttt gggacctggt ggattactttt   1740
ccaaatctgt ccaactcaat ggtcaagcct tgaagatggg ggatgatcaa accctgccag   1800
ctttgacaga aaagcctctc ggcccaggaa gttcactagg cttgcctgcc ttttcatatg   1860
ggtttttttgt cataagaaat gccaaagtcg cagcttgcat atga                  1904
```

<210> SEQ ID NO 7
<211> LENGTH: 558
<212> TYPE: PRT
<213> ORGANISM: mammalian

<400> SEQUENCE: 7

```
Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30
```

-continued

```
Arg Cys Gln Pro Gly Glu Pro Glu Met Leu Arg Leu Ser Leu Leu Leu
            35                  40                  45

Trp Leu Trp Gly Pro Leu Ser Pro Leu Val Gln Cys Ile Leu Ala Ala
 50                  55                  60

Gln Ala Glu Asp Val Val Glu Leu Glu Phe Ser Thr Gln Arg Pro Leu
 65                  70                  75                  80

His Leu Val Ser Pro Ser Phe Leu Ser Ile Thr Ile Asp Ala Asn Leu
                     85                  90                  95

Ala Thr Asp Pro Arg Phe Leu Thr Phe Leu Gly Ser Pro Lys Leu Arg
                100                 105                 110

Ala Leu Ala Arg Gly Leu Ser Pro Ala Tyr Leu Arg Phe Gly Gly Thr
            115                 120                 125

Lys Thr Asp Phe Leu Ile Phe Asp Pro Lys Lys Glu Pro Ser His Glu
130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Glu Phe Lys
                180                 185                 190

Asn Ser Thr Tyr Ser Arg Ser Ser Val Asp Met Leu Tyr Thr Phe Ala
                195                 200                 205

Arg Cys Ser Gly Leu Asp Leu Ile Phe Gly Leu Asn Ala Leu Leu Arg
            210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
                245                 250                 255

Pro Asn Ser Phe Trp Lys Lys Ala His Ile Ser Ile Asp Gly Leu Gln
                260                 265                 270

Leu Gly Glu Asp Tyr Ile Glu Leu Arg Lys Leu Leu Arg Lys Ser Thr
            275                 280                 285

Leu Lys Asn Val Lys Leu Tyr Gly Pro Asp Val Gly Gln Pro Arg Gly
            290                 295                 300

Lys Thr Val Lys Leu Leu Arg Ser Tyr Tyr Leu Asn Gly Arg Ile Ala
305                 310                 315                 320

Thr Lys Glu Asp Phe Leu Ser Pro Asp Val Leu Asp Thr Phe Ile Leu
                325                 330                 335

Ser Val Gln Lys Ile Leu Gln Val Val Glu Glu Thr Arg Pro Gly Lys
            340                 345                 350

Lys Val Trp Leu Gly Glu Thr Ser Ser Ala Tyr Gly Gly Gly Ala Pro
            355                 360                 365

Leu Leu Ser Asn Thr Phe Ala Ala Gly Phe Met Trp Leu Asp Lys Leu
            370                 375                 380

Gly Leu Ser Ala Gln Met Gly Ile Glu Val Val Met Arg Gln Val Phe
385                 390                 395                 400

Phe Gly Ala Gly Asn Tyr His Leu Val Asp Lys Asn Phe Glu Pro Leu
                405                 410                 415

Pro Asp Tyr Trp Leu Ser Leu Leu Phe Lys Lys Leu Val Gly Ser Lys
            420                 425                 430

Val Leu Met Ala Arg Val Lys Gly Pro Asp Arg Ser Lys Leu Arg Val
            435                 440                 445

Tyr Leu His Cys Thr Asn Ile Asn His Pro Arg Tyr Gln Glu Gly Asp
```

```
                450             455             460
Leu Thr Leu Tyr Ala Leu Asn Leu Tyr Asn Val Thr Lys His Leu Lys
465                 470                 475                 480

Leu Pro Tyr Gln Leu Phe Asn Lys Pro Val Asp Lys Tyr Leu Val Lys
                485                 490                 495

Pro Leu Gly Pro Gly Leu Leu Ser Lys Ser Val Gln Leu Asn Gly
            500                 505                 510

Gln Ala Leu Lys Met Val Asp Asp Gln Thr Leu Pro Ala Leu Thr Glu
        515                 520                 525

Lys Pro Leu Gly Pro Gly Ser Ser Leu Gly Leu Pro Ala Phe Ser Tyr
    530                 535                 540

Gly Phe Phe Val Ile Arg Asn Ala Lys Val Ala Ala Cys Ile
545                 550                 555

<210> SEQ ID NO 8
<211> LENGTH: 2030
<212> TYPE: DNA
<213> ORGANISM: mammalian

<400> SEQUENCE: 8
```

| | | | | | |
|---|---|---|---|---|---|
| tcagatttgg | gctggctcaa | gtgacaaata | agtgttttaa | ggcagatggg | ggtaggggt | 60 |
| agcctaaaag | ttcaacccag | gctttactcc | agggccagga | atccggtgcc | tagtgatggg | 120 |
| acctagaaga | ggggcagtga | gtgcaggaca | tcaggaagct | aggtcccagc | ctctgcgcag | 180 |
| tcggggcag | tccctcccca | ggccgccccg | atcttggatc | ccggccatct | ccgcaccctt | 240 |
| cagttgggtg | tgggtgatga | cgtgaccgcc | accaaaggga | aagctaacac | ggaaatggga | 300 |
| gagggcgggg | aggagaggcg | ctgggggcag | gatgcagggg | aggagtggga | gggatggagc | 360 |
| gcagtgggag | gtgcggagcc | gggaggcgct | ggcttgagag | ccggactcgg | agcccggcgg | 420 |
| gcggcagcag | gggcgccagc | tctctgggtc | gctgccagcc | aggtgagccc | gagatgctgc | 480 |
| ggctgtcgct | gctgctgtgg | ctctgggggc | cgctcagtcc | cctagtccag | tgcatcttgg | 540 |
| ccgcgcaggc | tgaagatgtg | gtagagctgg | agttctccac | ccagcggccg | ctgcacctgg | 600 |
| tgagtccctc | gttcctgtcc | atcaccatcg | acgccaacct | ggccaccgac | ccgcggttcc | 660 |
| tcaccttcct | gggttcccca | aaacttcggg | ctttggccag | aggtttgtct | cctgcatacc | 720 |
| taagatttgg | tggcaccaag | acagacttcc | ttattttga | ccccaagaag | gaaccaagcc | 780 |
| atgaagaaag | gagttactgg | aaatctcaag | tgaaccatga | tatttgtaga | tctggagcca | 840 |
| tccctgctgt | tgtagtgagg | agactacagg | tggaatggcc | cttccaggag | cagttgctac | 900 |
| tcagagaaca | gtaccaaaaa | gagtttaaaa | acagcactta | ctcacgaagc | tcagtggaca | 960 |
| tgctgtacac | gtttgctagg | tgctcgggat | tggacttgat | ctttggtcta | aatgcgttac | 1020 |
| taagaactgc | ggattttcgg | tggaacagct | ccaatgctca | gctcctgctg | aactactgct | 1080 |
| cttccaagaa | ctatgacata | tcctgggaac | tgggcaatga | gcctaatagt | ttttggaaga | 1140 |
| aggctcacat | ttccatcgat | ggattgcagt | taggagaaga | ttatattgag | ttgcgtaagc | 1200 |
| ttctaagaaa | atcaactctc | aaaaatgtga | aactctatgg | tcctgatgtt | ggtcaacctc | 1260 |
| gaggaaagac | agttaagttg | ctgagaagct | actatttgaa | tggacgaatt | gctaccaaag | 1320 |
| aagattttt | aagcccctgat | gttctggaca | ctttttatttt | atctgtgcaa | aaaattctac | 1380 |
| aggtggttga | ggagactaga | cctggcaaga | aagtctggct | gggagagaca | agctctgcat | 1440 |
| atggcggtgg | agcacccttg | ctgtccaaca | cctttgcagc | tggctttatg | tggctggata | 1500 |
| aattgggcct | gtcagcccaa | atgggcatag | aagtggtgat | gaggcaagtg | ttctttggag | 1560 |

-continued

```
ctggaaacta ccacttagtg gataaaaact tcgaacctttt acctgattat tggctgtctc      1620
ttctgttcaa gaaactggtg ggttccaagg tgttaatggc aagagtgaaa ggcccagaca      1680
gaagcaagct tcgagtgtac ctccactgca caaacatcaa tcacccaagg tatcaagaag      1740
gagatttaac tctgtacgcc ttaaaccttt ataatgtcac caagcacttg aagttacctt      1800
atcagttatt taacaaacca gtggataagt accttgtaaa acctttggga cctggtggat      1860
tactttccaa atctgtccaa ctcaatggtc aagccttgaa gatggtggat gatcaaaccc      1920
tgccagcttt gacagaaaag cctctcggcc caggaagttc actaggcttg cctgcctttt      1980
catatgggtt ttttgtcata agaaatgcca aagtcgcagc ttgcatatga                2030
```

<210> SEQ ID NO 9
<211> LENGTH: 525
<212> TYPE: PRT
<213> ORGANISM: mammalian

<400> SEQUENCE: 9

```
Met Glu Arg Ser Gly Arg Cys Gly Ala Gly Arg Trp Leu Glu Ser
 1               5                  10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Lys Glu Pro Ser His Glu
    130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Glu Phe Lys
            180                 185                 190

Asn Ser Thr Tyr Ser Arg Ser Ser Val Asp Met Leu Tyr Thr Phe Ala
        195                 200                 205

Arg Cys Ser Gly Leu Asp Leu Ile Phe Gly Leu Asn Ala Leu Leu Arg
    210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
                245                 250                 255

Pro Asn Ser Phe Trp Lys Lys Ala His Ile Ser Ile Asp Gly Leu Gln
            260                 265                 270

Leu Gly Glu Asp Tyr Ile Glu Leu Arg Lys Leu Leu Arg Lys Ser Thr
        275                 280                 285

Leu Lys Asn Val Lys Leu Tyr Gly Pro Asp Val Gly Gln Pro Arg Gly
    290                 295                 300
```

Lys Thr Val Lys Leu Leu Arg Ser Phe Leu Lys Ala Gly Gly Glu Val
305                 310                 315                 320

Ile Asp Ser Val Thr Trp His His Tyr Tyr Leu Asn Gly Arg Ile Ala
            325                 330                 335

Thr Lys Glu Asp Phe Leu Ser Pro Asp Val Leu Asp Thr Phe Ile Leu
        340                 345                 350

Ser Val Gln Lys Ile Leu Gln Val Val Glu Glu Thr Arg Pro Gly Lys
    355                 360                 365

Lys Val Trp Leu Gly Glu Thr Ser Ser Ala Tyr Gly Gly Ala Pro
370                 375                 380

Leu Leu Ser Asn Thr Phe Ala Ala Gly Phe Met Trp Leu Asp Lys Leu
385                 390                 395                 400

Gly Leu Ser Ala Gln Met Gly Ile Glu Val Val Met Arg Gln Val Phe
            405                 410                 415

Phe Gly Ala Gly Asn Tyr His Leu Val Asp Lys Asn Phe Glu Pro Leu
        420                 425                 430

Pro Asp Tyr Trp Leu Ser Leu Leu Phe Lys Lys Leu Val Gly Ser Lys
    435                 440                 445

Val Leu Met Ala Arg Val Lys Gly Pro Asp Arg Ser Lys Leu Arg Val
450                 455                 460

Tyr Leu His Cys Thr Asn Ile Asn Gln Ser Val Gln Leu Asn Gly Gln
465                 470                 475                 480

Ala Leu Lys Met Val Asp Asp Gln Thr Leu Pro Ala Leu Thr Glu Lys
            485                 490                 495

Pro Leu Gly Pro Gly Ser Ser Leu Gly Leu Pro Ala Phe Ser Tyr Gly
        500                 505                 510

Phe Phe Val Ile Arg Asn Ala Lys Val Ala Ala Cys Ile
    515                 520                 525

<210> SEQ ID NO 10
<211> LENGTH: 1931
<212> TYPE: DNA
<213> ORGANISM: mammalian

<400> SEQUENCE: 10
tcagatttgg gctggctcaa gtgacaaata agtgttttaa ggcagatggg ggtagggggt    60
agcctaaaag ttcaacccag gctttactcc agggccagga atccggtgcc tagtgatggg   120
acctagaaga ggggcagtga gtgcaggaca tcaggaagct aggtcccagc ctctgcgcag   180 tcggggcag tccctcccca ggccgccccg atcttggatc ccggccatct ccgcacccett   240 cagttgggtg tgggtgatga cgtgaccgcc accaaaggga aagctaacac ggaaatggga   300
gagggcgggg aggagaggcg ctgggggcag gatgcagggg aggagtggga gggatggagc   360
gcagtgggag gtgcggagcc gggaggcgct ggcttgagag ccggactcgg agcccggcgg   420
gcggcagcag gggcgccagc tctctgggtc gctgccagcc aggtgagccc gagatgctgc   480
ggctgtcgct gctgctgtgg ctctgggggc cgctcagtcc cctagtccag tgcatcttgg   540
ccgcgcaggc tgaagatgtg gtagagctgg agttctccac ccagcggccg ctgcacctgg   600
tgagtccctc gttcctgtcc atcaccatcg acgccaacct ggccaccgac ccgcggttcc   660
tcaccttcct gggttcccca aaacttcggg ctttggccag aggtttgtct cctgcatacc   720
taagatttgg tggcaccaag acagacttcc ttatttttga ccccaagaag gaaccaagcc   780
atgaagaaag gagttactgg aaatctcaag tgaaccatga tatttgtaga tctggagcca   840
tccctgctgt tgtagtgagg agactacagg tggaatggcc cttccaggag cagttgctac   900

-continued

```
tcagagaaca gtaccaaaaa gagtttaaaa acagcactta ctcacgaagc tcagtggaca   960
tgctgtacac gtttgctagg tgctcgggat tggacttgat ctttggtcta aatgcgttac  1020
taagaactgc ggattttcgg tggaacagct ccaatgctca gctcctgctg aactactgct  1080
cttccaagaa ctatgacata tcctgggaac tgggcaatga gcctaatagt ttttggaaga  1140
aggctcacat ttccatcgat ggattgcagt taggagaaga ttatattgag ttgcgtaagc  1200
ttctaagaaa atcaactctc aaaaatgtga aactctatgg tcctgatgtt ggtcaacctc  1260
gaggaaagac agttaagttg ctgagaagtt tcttgaaggc tggcggagaa gtgattgact  1320
cagttacatg gcatcactac tatttgaatg acgaattgc taccaaagaa gatttttaa   1380 gccctgatgt tctggacact tttatttat ctgtgcaaaa aattctacag gtggttgagg   1440
agactagacc tggcaagaaa gtctggctgg gagagacaag ctctgcatat ggcggtggag   1500 caccccttgct gtccaacacc tttgcagctg gctttatgtg gctggataaa ttgggcctgt   1560
cagcccaaat gggcatagaa gtggtgatga ggcaagtgtt ctttggagct ggaaactacc   1620
acttagtgga taaaaacttc gaacctttac ctgattattg gctgtctctt ctgttcaaga   1680
aactggtggg ttccaaggtg ttaatggcaa gagtgaaagg cccagacaga agcaagcttc   1740
gagtgtacct ccactgcaca aacatcaatc aatctgtcca actcaatggt caagccttga   1800
agatggtgga tgatcaaacc ctgccagctt tgacagaaaa gcctctcggc ccaggaagtt   1860
cactaggctt gcctgccttt tcatatgggt ttttgtcat aagaaatgcc aaagtcgcag   1920
cttgcatatg a                                                        1931
```

<210> SEQ ID NO 11
<211> LENGTH: 450
<212> TYPE: PRT
<213> ORGANISM: mammalian

<400> SEQUENCE: 11

```
Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Ala His Ile Ser Ile
    130                 135                 140

Asp Gly Leu Gln Leu Gly Glu Asp Tyr Ile Glu Leu Arg Lys Leu Leu
145                 150                 155                 160

Arg Lys Ser Thr Leu Lys Asn Val Lys Leu Tyr Gly Pro Asp Val Gly
                165                 170                 175

Gln Pro Arg Gly Lys Thr Val Lys Leu Leu Arg Ser Phe Leu Lys Ala
            180                 185                 190
```

```
Gly Gly Glu Val Ile Asp Ser Val Thr Trp His His Tyr Tyr Leu Asn
            195                 200                 205

Gly Arg Ile Ala Thr Lys Glu Asp Phe Leu Ser Pro Asp Val Leu Asp
        210                 215                 220

Thr Phe Ile Leu Ser Val Gln Lys Ile Leu Gln Val Val Glu Glu Thr
225                 230                 235                 240

Arg Pro Gly Lys Lys Val Trp Leu Gly Glu Thr Ser Ser Ala Tyr Gly
                245                 250                 255

Gly Gly Ala Pro Leu Leu Ser Asn Thr Phe Ala Ala Gly Phe Met Trp
            260                 265                 270

Leu Asp Lys Leu Gly Leu Ser Ala Gln Met Gly Ile Glu Val Val Met
        275                 280                 285

Arg Gln Val Phe Phe Gly Ala Gly Asn Tyr His Leu Val Asp Lys Asn
    290                 295                 300

Phe Glu Pro Leu Pro Asp Tyr Trp Leu Ser Leu Leu Phe Lys Lys Leu
305                 310                 315                 320

Val Gly Ser Lys Val Leu Met Ala Arg Val Lys Gly Pro Asp Arg Ser
                325                 330                 335

Lys Leu Arg Val Tyr Leu His Cys Thr Asn Ile Asn His Pro Arg Tyr
            340                 345                 350

Gln Glu Gly Asp Leu Thr Leu Tyr Ala Leu Asn Leu Tyr Asn Val Thr
        355                 360                 365

Lys His Leu Lys Leu Pro Tyr Gln Leu Phe Asn Lys Pro Val Asp Lys
370                 375                 380

Tyr Leu Val Lys Pro Leu Gly Pro Gly Gly Leu Leu Ser Lys Ser Val
385                 390                 395                 400

Gln Leu Asn Gly Gln Ala Leu Lys Met Val Asp Asp Gln Thr Leu Pro
                405                 410                 415

Ala Leu Thr Glu Lys Pro Leu Gly Pro Gly Ser Ser Leu Gly Leu Pro
            420                 425                 430

Ala Phe Ser Tyr Gly Phe Phe Val Ile Arg Asn Ala Lys Val Ala Ala
        435                 440                 445

Cys Ile
    450

<210> SEQ ID NO 12
<211> LENGTH: 1706
<212> TYPE: DNA
<213> ORGANISM: mammalian

<400> SEQUENCE: 12
tcagatttgg gctggctcaa gtgacaaata agtgttttaa ggcagatggg ggtagggggt      60
agcctaaaag ttcaacccag gctttactcc agggccagga atccggtgcc tagtgatggg     120
acctagaaga ggggcagtga gtgcaggaca tcaggaagct aggtcccagc ctctgcgcag     180 tcggggcag tccctcccca ggccgccccg atcttggatc ccggccatct ccgcaccctt      240
cagttgggtg tgggtgatga cgtgaccgcc accaaaggga aagctaacac ggaaatggga     300
gagggcgggg aggagaggcg ctgggggcag gatgcagggg aggagtggga gggatggagc     360
gcagtgggag gtgcggagcc gggaggcgct ggcttgagag ccggactcgg agccggcgg      420 gcggcagcag gggcgccagc tctctgggtc gctgccagcc aggtgagccc gagatgctgc     480
ggctgtcgct gctgctgtgg ctctgggggc cgctcagtcc cctagtccag tgcatcttgg     540
ccgcgcaggc tgaagatgtg gtagagctgg agttctccac ccagcggccg ctgcacctgg     600
```

```
tgagtccctc gttcctgtcc atcaccatcg acgccaacct ggccaccgac ccgcggttcc    660
tcaccttcct gggttcccca aaacttcggg ctttggccag aggtttgtct cctgcatacc    720
taagatttgg tggcaccaag acagacttcc ttattttga ccccaagaag gctcacattt    780
ccatcgatgg attgcagtta ggagaagatt atattgagtt gcgtaagctt ctaagaaaat    840
caactctcaa aaatgtgaaa ctctatggtc ctgatgttgg tcaacctcga ggaaagacag    900
ttaagttgct gagaagtttc ttgaaggctg gcggagaagt gattgactca gttacatggc    960
atcactacta tttgaatgga cgaattgcta ccaagaaga tttttttaagc cctgatgttc   1020
tggacacttt tattttatct gtgcaaaaaa ttctacaggt ggttgaggag actagacctg   1080
gcaagaaagt ctggctggga gagacaagct ctgcatatgg cggtggagca cccttgctgt   1140
ccaacaccct tgcagctggc tttatgtggc tggataaatt gggcctgtca gcccaaatgg   1200
gcatagaagt ggtgatgagg caagtgttct ttggagctgg aaactaccac ttagtggata   1260
aaaacttcga acctttacct gattattggc tgtctcttct gttcaagaaa ctggtgggtt   1320
ccaaggtgtt aatggcaaga gtgaaaggcc cagacagaag caagcttcga gtgtacctcc   1380
actgcacaaa catcaatcac ccaaggtatc aagaaggaga tttaactctg tacgccttaa   1440
acctttataa tgtcaccaag cacttgaagt taccttatca gttatttaac aaaccagtgg   1500
ataagtacct tgtaaaaacct ttgggacctg gtggattact ttccaaatct gtccaactca   1560
atggtcaagc cttgaagatg gtggatgatc aaaccctgcc agctttgaca gaaaagcctc   1620
tcggcccagg aagttcacta ggcttgcctg ccttttcata tgggtttttt gtcataagaa   1680
atgccaaagt cgcagcttgc atatga                                         1706

<210> SEQ ID NO 13
<211> LENGTH: 474
<212> TYPE: PRT
<213> ORGANISM: mammalian

<400> SEQUENCE: 13

Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Lys Glu Pro Ser His Glu
    130                 135                 140

Glu Arg Ser Tyr Trp Lys Ser Gln Val Asn His Glu Pro Asn Ser Phe
145                 150                 155                 160

Trp Lys Lys Ala His Ile Ser Ile Asp Gly Leu Gln Leu Gly Glu Asp
                165                 170                 175

Tyr Ile Glu Leu Arg Lys Leu Leu Arg Lys Ser Thr Leu Lys Asn Val
```

```
                     180                 185                 190
Lys Leu Tyr Gly Pro Asp Val Gly Gln Pro Arg Gly Lys Thr Val Lys
            195                 200                 205

Leu Leu Arg Ser Phe Leu Lys Ala Gly Gly Glu Val Ile Asp Ser Val
            210                 215                 220

Thr Trp His His Tyr Tyr Leu Asn Gly Arg Ile Ala Thr Lys Glu Asp
225                 230                 235                 240

Phe Leu Ser Pro Asp Val Leu Asp Thr Phe Ile Leu Ser Val Gln Lys
                245                 250                 255

Ile Leu Gln Val Val Glu Glu Thr Arg Pro Gly Lys Lys Val Trp Leu
            260                 265                 270

Gly Glu Thr Ser Ser Ala Tyr Gly Gly Gly Ala Pro Leu Leu Ser Asn
            275                 280                 285

Thr Phe Ala Ala Gly Phe Met Trp Leu Asp Lys Leu Gly Leu Ser Ala
            290                 295                 300

Gln Met Gly Ile Glu Val Val Met Arg Gln Val Phe Phe Gly Ala Gly
305                 310                 315                 320

Asn Tyr His Leu Val Asp Lys Asn Phe Glu Pro Leu Pro Asp Tyr Trp
                325                 330                 335

Leu Ser Leu Leu Phe Lys Lys Leu Val Gly Ser Lys Val Leu Met Ala
                340                 345                 350

Arg Val Lys Gly Pro Asp Arg Ser Lys Leu Arg Val Tyr Leu His Cys
            355                 360                 365

Thr Asn Ile Asn His Pro Arg Tyr Gln Glu Gly Asp Leu Thr Leu Tyr
370                 375                 380

Ala Leu Asn Leu Tyr Asn Val Thr Lys His Leu Lys Leu Pro Tyr Gln
385                 390                 395                 400

Leu Phe Asn Lys Pro Val Asp Lys Tyr Leu Val Lys Pro Leu Gly Pro
                405                 410                 415

Gly Gly Leu Leu Ser Lys Ser Val Gln Leu Asn Gly Gln Ala Leu Lys
            420                 425                 430

Met Val Asp Asp Gln Thr Leu Pro Ala Leu Thr Glu Lys Pro Leu Gly
            435                 440                 445

Pro Gly Ser Ser Leu Gly Leu Pro Ala Phe Ser Tyr Gly Phe Phe Val
            450                 455                 460

Ile Arg Asn Ala Lys Val Ala Ala Cys Ile
465                 470

<210> SEQ ID NO 14
<211> LENGTH: 1778
<212> TYPE: DNA
<213> ORGANISM: mammalian

<400> SEQUENCE: 14
tcagatttgg gctggctcaa gtgacaaata agtgttttaa ggcagatggg ggtagggggt      60
agcctaaaag ttcaacccag gctttactcc agggccagga atccggtgcc tagtgatggg     120
acctagaaga gggcagtgaa gtgcaggaca tcaggaagct aggtcccagc ctctgcgcag     180 tcggggcag tccctcccca ggccgccccg atcttggatc ccggccatct ccgcacccctt     240 cagttgggtg tgggtgatga cgtgaccgcc accaaaggga aagctaacac ggaaatggga     300
gagggcgggg aggagaggcg ctgggggcag gatgcagggg aggagtggga gggatggagc     360
gcagtgggag gtgcggagcc gggaggcgct ggcttgagag ccggactcgg agccggcgg     420 gcggcagcag gggcgccagc tctctgggtc gctgccagcc aggtgagccc gagatgctgc     480
```

-continued

```
ggctgtcgct gctgctgtgg ctctgggggc cgctcagtcc cctagtccag tgcatcttgg    540
ccgcgcaggc tgaagatgtg gtagagctgg agttctccac ccagcggccg ctgcacctgg    600
tgagtccctc gttcctgtcc atcaccatcg acgccaacct ggccaccgac ccgcggttcc    660
tcaccttcct gggttcccca aaacttcggg ctttggccag aggtttgtct cctgcatacc    720
taagatttgg tggcaccaag acagacttcc ttattttga ccccaagaag gaaccaagcc     780
atgaagaaag gagttactgg aaatctcaag tgaaccatga cctaatagt ttttggaaga     840 aggctcacat ttccatcgat ggattgcagt taggagaaga ttatattgag ttgcgtaagc    900
ttctaagaaa atcaactctc aaaaatgtga aactctatgg tcctgatgtt ggtcaacctc    960
gaggaaagac agttaagttg ctgagaagtt tcttgaaggc tggcggagaa gtgattgact   1020
cagttacatg gcatcactac tatttgaatg gacgaattgc taccaaagaa gattttttaa   1080
gccctgatgt tctggacact tttattttat ctgtgcaaaa aattctacag gtggttgagg   1140
agactagacc tggcaagaaa gtctggctgg gagagacaag ctctgcatat ggcggtggag   1200 caccccttgct gtccaacacc tttgcagctg gctttatgtg gctggataaa ttgggcctgt   1260
cagcccaaat gggcatagaa gtggtgatga ggcaagtgtt ctttggagct ggaaactacc   1320
acttagtgga taaaaacttc gaacctttac ctgattattg gctgtctctt ctgttcaaga   1380
aactggtggg ttccaaggtg ttaatggcaa gagtgaaagg cccagacaga agcaagcttc   1440
gagtgtacct ccactgcaca aacatcaatc acccaaggta tcaagaagga gatttaactc   1500
tgtacgcctt aaacctttat aatgtcacca agcacttgaa gttacctat cagttattta    1560 acaaaccagt ggataagtac cttgtaaaac ctttgggacc tggtggatta ctttccaaat   1620
ctgtccaact caatggtcaa gccttgaaga tggtggatga tcaaaccctg ccagctttga   1680
cagaaaagcc tctcggccca ggaagttcac taggcttgcc tgccttttca tatgggtttt   1740
ttgtcataag aaatgccaaa gtcgcagctt gcatatga                           1778
```

<210> SEQ ID NO 15
<211> LENGTH: 258
<212> TYPE: PRT
<213> ORGANISM: mammalian

<400> SEQUENCE: 15

```
Met Glu Arg Ser Gly Arg Cys Gly Ala Gly Arg Trp Leu Glu Ser
  1               5                  10                  15

Arg Thr Arg Ser Pro Ala Gly Gly Ser Arg Gly Ala Ser Ser Leu Gly
                 20                  25                  30

Arg Cys Gln Pro Gly Glu Pro Glu Met Leu Arg Leu Ser Leu Leu Leu
             35                  40                  45

Trp Leu Trp Gly Pro Leu Ser Pro Leu Val Gln Cys Ile Leu Ala Ala
         50                  55                  60

Gln Ala Glu Asp Val Val Glu Leu Glu Phe Ser Thr Gln Arg Pro Leu
 65                  70                  75                  80

His Leu Val Ser Pro Ser Phe Leu Ser Ile Thr Ile Asp Ala Asn Leu
                     85                  90                  95

Ala Thr Asp Pro Arg Phe Leu Thr Phe Leu Gly Ser Pro Lys Leu Arg
                100                 105                 110

Ala Leu Ala Gly Gly Leu Ser Pro Ala Tyr Leu Arg Phe Gly Gly Thr
            115                 120                 125

Lys Thr Asp Phe Leu Ile Phe Asp Pro Lys Lys Glu Pro Ser His Glu
        130                 135                 140

Glu Arg Ser Tyr Trp Lys Ser Gln Val Asn His Asp Ile Cys Arg Ser
```

```
                145                 150                 155                 160
Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Glu Phe Lys
                180                 185                 190

Asn Ser Thr Tyr Ser Arg Ser Ser Val Asp Met Leu Tyr Thr Phe Ala
                195                 200                 205

Arg Cys Ser Gly Leu Asp Leu Ile Phe Gly Leu Asn Ala Leu Leu Arg
                210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Ala
                245                 250                 255

Thr Ile

<210> SEQ ID NO 16
<211> LENGTH: 1508
<212> TYPE: DNA
<213> ORGANISM: mammalian

<400> SEQUENCE: 16
atggagcgca gtgggaggtg cggagccggg aggcgctggc ttgagagccg gactcggagc      60
ccggcgggcg gcagcagggg cgccagctct ctgggtcgct gccagccagg tgagcccgag     120
atgctgcggc tgtcgctgct gctgtggctc tgggggccgc tcagtcccct agtccagtgc     180
atcttggccg cgcaggctga agatgtggta gagctggagt tctccaccca gcggccgctg     240
cacctggtga gtccctcgtt cctgtccatc accatcgacg ccaacctggc caccgacccg     300
cggttcctca ccttcctggg ttccccaaaa cttcgggctt tggccggagg tttgtctcct     360
gcatacctaa gatttggtgg caccaagaca gacttcctta tttttgaccc caagaaggaa     420
ccaagccatg aagaaggag ctactggaaa tctcaagtga accatgatat tgtagatct      480
ggagccatcc ctgctgttgt agtgaggaga ctacaggtgg aatgcccctt ccaggagcag     540
ttgctactca gagaacagta ccaaaaagag tttaaaaaca gcacttactc acgaagctca     600
gtggacatgc tgtacacgtt tgctaggtgc tcgggattgg acttgatctt tggtctaaat     660
gcgttactaa gaactgcgga ttttcggtgg aacagctcca atgctcagct cctgctgaac     720
tactgctctt ccaagaacta tgacatatcc tgggaactgg gcaatgctac tatttgaatg     780
gacgaattgc taccaaagaa gatttttaa gccctgatgt tctggacact tttattttat     840
ctgtgcaaaa aattctacag gtggttgagg agactagacc tggcaagaaa gtctggctgg     900
gagagacaag ctctgcatat ggcggtggag cgcccttgct gtccaacacc tttgcagctg     960
gctttatgtg gctggataaa ttgggcctgt cagcccaaat gggcatagaa gtggtgatga    1020
ggcaagtgtt ctttggagct ggaaactacc acttagtgga taaaaacttc gaacctttac    1080
ctgattattg gctgtctctt ctgttcaaga aactggtggg ttccaaggtg ttaatggcaa    1140
gagtgaaagg cccagacaga agcaagcttc gagtgtacct ccactgcaca acatcaatc    1200
acccaaggta tcaagaagga gatttaactc tgtacgcctt aaacctttat aatgtcacca    1260
agcacttgaa gttaccttat cagttattta acaaaccagt ggataagtac cttgtaaaac    1320
ctttgggacc tggtggatta cttttccaaat ctgtccaact caatggtcaa gccttgaaga    1380
tggtggatga tcaaaccctg ccagctttga cagaaaagcc tctcggccca ggaagttcac    1440
taggcttgcc tgccttttca tatgggtttt ttgtcataag aaatgccaaa gtcgcagctt    1500
```

```
                                                gcatatga                                              1508
```

<210> SEQ ID NO 17
<211> LENGTH: 264
<212> TYPE: PRT
<213> ORGANISM: mammalian

<400> SEQUENCE: 17

```
Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Lys Glu Pro Ser His Glu
    130                 135                 140

Glu Arg Ser Tyr Trp Lys Ser Gln Val Asn His Asp Ile Cys Arg Ser
145                 150                 155                 160

Gly Ala Ile Pro Ala Val Val Arg Leu Gln Val Glu Trp Pro
                165                 170                 175                 Pro

Phe Gln Glu Gln Leu Leu Leu Arg Glu Gln Tyr Gln Lys Glu Phe Lys
            180                 185                 190

Asn Ser Thr Tyr Ser Arg Ser Ser Val Asp Met Leu Tyr Thr Phe Ala
        195                 200                 205

Arg Cys Ser Gly Leu Asp Leu Ile Phe Gly Leu Asn Ala Leu Leu Arg
    210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Asp
                245                 250                 255

Leu Ser Asn Ser Met Val Lys Ala
            260
```

<210> SEQ ID NO 18
<211> LENGTH: 926
<212> TYPE: DNA
<213> ORGANISM: mammalian

<400> SEQUENCE: 18

```
atggagcgca gtgggaggtg cggagccggg aggcgctggc ttgagagccg gactcggagc      60
ccggcgggcg gcagcagggg cgccagctct ctgggtcgct gccagccagg tgagcccgag     120
atgctgcggc tgtcgctgct gctgtggctc tggggccgc tcagtcccct agtccagtgc      180
atcttggccg cgcaggctga agatgtggta gagctggagt ctccacccca gcggccgctg    240
cacctggtga gtccctcgtt cctgtccatc accatcgacg ccaacctggc caccgacccg     300
cggttcctca ccttcctggg ttccccaaaa cttcgggctt tggccagggg tttgtctcct     360
```

```
gcatacctaa gatttggtgg caccaagaca gacttcctta tttttgaccc caagaaggaa      420
ccaagtcatg aagaaggag ttactggaaa tctcaagtga accatgatat ttgtagatct       480
ggagccatcc ctgctgttgt agtgaggaga ctacaggtgg aatggcccctt ccaggagcag     540 ttgctactca gagaacagta ccaaaaagag tttaaaaaca gcacttactc acgaagctca      600
gtggacatgc tgtacacgtt tgctaggtgc tcgggattgg acttgatctt tggtctaaat      660
gcgttactaa gaactgcgga ttttcggtgg aacagctcca atgctcagct cctgctgaac      720
tactgctctt ccaagaacta tgacatatcc tgggaactgg gcaatgatct gtccaactca      780
atggtcaagg cttgaagatg gtggatgatc aaaccctgcc agctttgaca gaaaagcctc      840
tccgcccagg aagttcacta ggcttgcctg ccttttcata tgggttttt gtcataagaa       900 atgccaaagt tgctgcttgt ctatga                                           926

<210> SEQ ID NO 19
<211> LENGTH: 488
<212> TYPE: PRT
<213> ORGANISM: Homo sapiens

<400> SEQUENCE: 19

Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Gly
            100                 105                 110

Ser Ser Val Asp Val Leu Tyr Thr Phe Ala Asn Cys Ser Gly Leu Asp
        115                 120                 125

Leu Ile Phe Gly Leu Asn Ala Leu Leu Arg Thr Ala Asp Leu Gln Trp
    130                 135                 140

Asn Ser Ser Asn Ala Gln Leu Leu Leu Asp Tyr Cys Ser Ser Lys Gly
145                 150                 155                 160

Tyr Asn Ile Ser Trp Glu Leu Gly Asn Glu Pro Asn Ser Phe Leu Lys
                165                 170                 175

Lys Ala Asp Ile Phe Ile Asn Gly Ser Gln Leu Gly Glu Asp Phe Ile
            180                 185                 190

Gln Leu His Lys Leu Leu Arg Lys Ser Thr Phe Lys Asn Ala Lys Leu
        195                 200                 205

Tyr Gly Pro Asp Val Gly Gln Pro Arg Arg Lys Thr Ala Lys Met Leu
    210                 215                 220

Lys Ser Phe Leu Lys Ala Gly Gly Glu Val Ile Asp Ser Val Thr Trp
225                 230                 235                 240

His His Tyr Tyr Leu Asn Gly Arg Thr Ala Thr Arg Glu Asp Phe Leu
                245                 250                 255

Asn Pro Asp Val Leu Asp Ile Phe Ile Ser Ser Val Gln Lys Val Phe
            260                 265                 270
```

```
Gln Val Val Glu Ser Thr Arg Pro Gly Lys Lys Val Trp Leu Gly Glu
    275                 280                 285

Thr Ser Ser Ala Tyr Gly Gly Ala Pro Leu Leu Ser Asp Thr Phe
290                 295                 300

Ala Ala Gly Phe Met Trp Leu Asp Lys Leu Gly Leu Ser Ala Arg Met
305                 310                 315                 320

Gly Ile Glu Val Met Arg Gln Val Phe Gly Ala Gly Asn Tyr
                325                 330                 335

His Leu Val Asp Glu Asn Phe Asp Pro Leu Pro Asp Tyr Trp Leu Ser
                340                 345                 350

Leu Leu Phe Lys Lys Leu Val Gly Thr Lys Val Leu Met Ala Ser Val
                355                 360                 365

Gln Gly Ser Lys Arg Arg Lys Leu Arg Val Tyr Leu His Cys Thr Asn
            370                 375                 380

Thr Asp Asn Pro Arg Tyr Lys Glu Gly Asp Leu Thr Leu Tyr Ala Ile
385                 390                 395                 400

Asn Leu His Asn Val Thr Lys Tyr Leu Arg Leu Pro Tyr Pro Phe Ser
                405                 410                 415

Asn Lys Gln Val Asp Lys Tyr Leu Leu Arg Pro Leu Gly Pro His Gly
            420                 425                 430

Leu Leu Ser Lys Ser Val Gln Leu Asn Gly Leu Thr Leu Lys Met Val
            435                 440                 445

Asp Asp Gln Thr Leu Pro Pro Leu Met Glu Lys Pro Leu Arg Pro Gly
        450                 455                 460

Ser Ser Leu Gly Leu Pro Ala Phe Ser Tyr Ser Phe Phe Val Ile Arg
465                 470                 475                 480

Asn Ala Lys Val Ala Ala Cys Ile
                485

<210> SEQ ID NO 20
<211> LENGTH: 1632
<212> TYPE: DNA
<213> ORGANISM: Homo sapiens

<400> SEQUENCE: 20
aggagaaaag ggcgctgggg ctcggcggga ggaagtgcta gagctctcga ctctccgctg      60
cgcggcagct ggcgggggga gcagccaggt gagcccaaga tgctgctgcg ctcgaagcct     120
gcgctgccgc cgccgctgat gctgctgctc ctggggccgc tgggtcccct ctcccctggc     180
gccctgcccc gacctgcgca agcacaggac gtcgtggacc tggacttctt cacccaggag     240
ccgctgcacc tggtgagccc ctcgttcctg tccgtcacca ttgacgccaa cctggccacg     300
gacccgcggt tcctcatcct cctgggttct ccaaagcttc gtaccttggc cagaggcttg     360
tctcctgcgt acctgaggtt tggtggcacc aagacagact tcctaatttt cgatcccaag     420
aaggaatcaa cctttgaaga gagaagttac tggcaatctc aagtcaacca gggaagctct     480
gtagatgtgc tatacacttt tgcaaactgc tcaggactgg acttgatctt tggcctaaat     540
gcgttattaa gaacagcaga tttgcagtgg aacagttcta atgctcagtt gctcctggac     600
tactgctctt ccaaggggta taacatttct tgggaactag gcaatgaacc taacagtttc     660
cttaagaagg ctgatatttt catcaatggg tcgcagttag agaagatttt attcaattg      720 cataaacttc taagaaagtc caccttcaaa aatgcaaaac tctatggtcc tgatgttggt     780
cagcctcgaa gaaagacggc taagatgctg aagagcttcc tgaaggctgg tgagaagtg      840 attgattcag ttacatggca tcactactat ttgaatggac ggactgctac cagggaagat     900
```

-continued

```
tttctaaacc ctgatgtatt ggacattttt atttcatctg tgcaaaaagt tttccaggtg      960
gttgagagca ccaggcctgg caagaaggtc tggttaggag aaacaagctc tgcatatgga     1020
ggcggagcgc ccttgctatc cgacaccttt gcagctggct ttatgtggct ggataaattg     1080
ggcctgtcag cccgaatggg aatagaagtg gtgatgaggc aagtattctt ggagcagga     1140
aactaccatt tagtggatga aaacttcgat cctttacctg attattggct atctcttctg     1200
ttcaagaaat tggtgggcac caaggtgtta atggcaagcg tgcaaggttc aaagagaagg     1260
aagcttcgag tataccttca ttgcacaaac actgacaatc caaggtataa agaaggagat     1320
ttaactctgt atgccataaa cctccataac gtcaccaagt acttgcggtt accctatcct     1380
ttttctaaca agcaagtgga taaataccct ctaagacctt gggacctca tggattactt     1440
tccaaatctg tccaactcaa tggtctaact ctaaagatgg tggatgatca aaccttgcca     1500
cctttaatgg aaaaacctct ccggccagga agttcactgg gcttgccagc tttctcatat     1560
agttttttg tgataagaaa tgccaaagtt gctgcttgca tctgaaaata aaatatacta     1620
gtcctgacac tg                                                        1632

<210> SEQ ID NO 21
<211> LENGTH: 472
<212> TYPE: PRT
<213> ORGANISM: Homo sapiens

<400> SEQUENCE: 21

Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Lys Pro Asn Ser Phe Leu Lys
145                 150                 155                 160

Lys Ala Asp Ile Phe Ile Asn Gly Ser Gln Leu Gly Glu Asp Phe Ile
                165                 170                 175

Gln Leu His Lys Leu Leu Arg Lys Ser Thr Phe Lys Asn Ala Lys Leu
            180                 185                 190

Tyr Gly Pro Asp Val Gly Gln Pro Arg Arg Lys Thr Ala Lys Met Leu
        195                 200                 205

Lys Ser Phe Leu Lys Ala Gly Gly Glu Val Ile Asp Ser Val Thr Trp
    210                 215                 220

His His Tyr Tyr Leu Asn Gly Arg Thr Ala Thr Arg Glu Asp Phe Leu
225                 230                 235                 240

Asn Pro Asp Val Leu Asp Ile Phe Ile Ser Ser Val Gln Lys Val Phe
```

```
                       245                 250                 255
Gln Val Val Glu Ser Thr Arg Pro Gly Lys Lys Val Trp Leu Gly Glu
                260                 265                 270
Thr Ser Ser Ala Tyr Gly Gly Ala Pro Leu Leu Ser Asp Thr Phe
            275                 280                 285
Ala Ala Gly Phe Met Trp Leu Asp Lys Leu Gly Leu Ser Ala Arg Met
        290                 295                 300
Gly Ile Glu Val Val Met Arg Gln Val Phe Phe Gly Ala Gly Asn Tyr
305                 310                 315                 320
His Leu Val Asp Glu Asn Phe Asp Pro Leu Pro Asp Tyr Trp Leu Ser
                325                 330                 335
Leu Leu Phe Lys Lys Leu Val Gly Thr Lys Val Leu Met Ala Ser Val
                340                 345                 350
Gln Gly Ser Lys Arg Arg Lys Leu Arg Val Tyr Leu His Cys Thr Asn
            355                 360                 365
Thr Asp Asn Pro Arg Tyr Lys Glu Gly Asp Leu Thr Leu Tyr Ala Ile
        370                 375                 380
Asn Leu His Asn Val Thr Lys Tyr Leu Arg Leu Pro Tyr Pro Phe Ser
385                 390                 395                 400
Asn Lys Gln Val Asp Lys Tyr Leu Leu Arg Pro Leu Gly Pro His Gly
                405                 410                 415
Leu Leu Ser Lys Ser Val Gln Leu Asn Gly Leu Thr Leu Lys Met Val
                420                 425                 430
Asp Asp Gln Thr Leu Pro Pro Leu Met Glu Lys Pro Leu Arg Pro Gly
            435                 440                 445
Ser Ser Leu Gly Leu Pro Ala Phe Ser Tyr Ser Phe Phe Val Ile Arg
        450                 455                 460
Asn Ala Lys Val Ala Ala Cys Ile
465                 470

<210> SEQ ID NO 22
<211> LENGTH: 1584
<212> TYPE: DNA
<213> ORGANISM: Homo sapiens

<400> SEQUENCE: 22
aggagaaaag ggcgctgggg ctcggcggga ggaagtgcta gagctctcga ctctccgctg     60
cgcggcagct ggcgggggga gcagccaggt gagcccaaga tgctgctgcg ctcgaagcct    120
gcgctgccgc cgccgctgat gctgctgctc ctggggccgc tggtcccct ctccctggc     180 gccctgcccc gacctgcgca agcacaggac gtcgtggacc tggacttctt cacccaggag    240
ccgctgcacc tggtgagccc ctcgttcctg tccgtcacca ttgacgccaa cctggccacg    300
gacccgcggt tcctcatcct cctgggttct ccaaagcttc gtaccttggc cagaggcttg    360
tctcctgcgt acctgaggtt tggtggcacc aagacagact tcctaatttt cgatcccaag    420
aaggaatcaa cctttgaaga gagaagttac tggcaatctc aagtcaacca ggatatttgc    480
aaatatggat ccatccctcc tgatgtggag gagaagttac ggttggaatg ccctaccag    540 gagcaattgc tactccgaga cactaccag aaaaagttca gaacagcac ctactcaaaa     600 cctaacagtt tccttaagaa ggctgatatt ttcatcaatg ggtcgcagtt aggagaagat    660
tttattcaat tgcataaact tctaagaaag tccaccttca aaaatgcaaa actctatggt    720
cctgatgttg gtcagcctcg aagaaagacg gctaagatgc tgaagagctt cctgaaggct    780
ggtggagaag tgattgattc agttacatgg catcactact atttgaatgg acggactgct    840
```

-continued

```
accagggaag attttctaaa ccctgatgta ttggacattt ttatttcatc tgtgcaaaaa    900
gttttccagg tggttgagag caccaggcct ggcaagaagg tctggttagg agaaacaagc    960
tctgcatatg gaggcggagc gcccttgcta tccgacacct ttgcagctgg ctttatgtgg   1020
ctggataaat tgggcctgtc agcccgaatg gaatagaag tggtgatgag caagtattc    1080
tttggagcag gaaactacca tttagtggat gaaaacttcg atcctttacc tgattattgg   1140
ctatctcttc tgttcaagaa attggtgggc accaaggtgt aatggcaag cgtgcaaggt    1200
tcaaagagaa ggaagcttcg agtataccct cattgcacaa acactgacaa tccaaggtat   1260
aaagaaggag atttaactct gtatgccata aacctccata acgtcaccaa gtacttgcgg   1320
ttaccctatc cttttctaa caagcaagtg gataaatacc ttctaagacc tttgggacct    1380
catggattac tttccaaatc tgtccaactc aatggtctaa ctctaaagat ggtggatgat   1440
caaaccttgc cacctttaat ggaaaaacct ctccggccag gaagttcact gggcttgcca   1500
gctttctcat atagttttt tgtgataaga aatgccaaag ttgctgcttg catctgaaaa   1560
taaaatatac tagtcctgac actg                                          1584
```

<210> SEQ ID NO 23
<211> LENGTH: 514
<212> TYPE: PRT
<213> ORGANISM: Homo sapiens

<400> SEQUENCE: 23

```
Met Leu Leu Leu Leu Gly Pro Leu Gly Pro Leu Ser Pro Gly Ala Leu
 1               5                  10                  15

Pro Arg Pro Ala Gln Ala Gln Asp Val Val Asp Leu Asp Phe Phe Thr
                20                  25                  30

Gln Glu Pro Leu His Leu Val Ser Pro Ser Phe Leu Ser Val Thr Ile
            35                  40                  45

Asp Ala Asn Leu Ala Thr Asp Pro Arg Phe Leu Ile Leu Leu Gly Ser
        50                  55                  60

Pro Lys Leu Arg Thr Leu Ala Arg Gly Leu Ser Pro Ala Tyr Leu Arg
    65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Arg Ser Ser Val Asp Val Leu
145                 150                 155                 160

Tyr Thr Phe Ala Asn Cys Ser Gly Leu Asp Leu Ile Phe Gly Leu Asn
                165                 170                 175

Ala Leu Leu Arg Thr Ala Asp Leu Gln Trp Asn Ser Ser Asn Ala Gln
            180                 185                 190

Leu Leu Leu Asp Tyr Cys Ser Ser Lys Gly Tyr Asn Ile Ser Trp Glu
        195                 200                 205

Leu Gly Asn Glu Pro Asn Ser Phe Leu Lys Lys Ala Asp Ile Phe Ile
    210                 215                 220

Asn Gly Ser Gln Leu Gly Glu Asp Phe Ile Gln Leu His Lys Leu Leu
225                 230                 235                 240

Arg Lys Ser Thr Phe Lys Asn Ala Lys Leu Tyr Gly Pro Asp Val Gly
```

|  |  |  |  | 245 |  |  |  | 250 |  |  |  | 255 |  |
Gln Pro Arg Arg Lys Thr Ala Lys Met Leu Lys Ser Tyr Tyr Leu Asn
                    260                 265                 270
Gly Arg Thr Ala Thr Arg Glu Asp Phe Leu Asn Pro Asp Val Leu Asp
                275                 280                 285
Ile Phe Ile Ser Ser Val Gln Lys Val Phe Gln Val Val Glu Ser Thr
            290                 295                 300
Arg Pro Gly Lys Lys Val Trp Leu Gly Glu Thr Ser Ala Tyr Gly Gly
305                 310                 315                 320
Gly Gly Ala Pro Leu Leu Ser Asp Thr Phe Ala Ala Gly Phe Met Trp
                325                 330                 335
Leu Asp Lys Leu Gly Leu Ser Ala Arg Met Gly Ile Glu Val Val Met
                340                 345                 350
Arg Gln Val Phe Phe Gly Ala Gly Asn Tyr His Leu Val Asp Glu Asn
                355                 360                 365
Phe Asp Pro Leu Pro Asp Tyr Trp Leu Ser Leu Phe Lys Lys Leu
            370                 375                 380
Val Gly Thr Lys Val Leu Met Ala Ser Val Gln Gly Ser Lys Arg Arg
385                 390                 395                 400
Lys Leu Arg Val Tyr Leu His Cys Thr Asn Thr Asp Asn Pro Arg Tyr
                405                 410                 415
Lys Glu Gly Asp Leu Thr Leu Tyr Ala Ile Asn Leu His Asn Val Thr
            420                 425                 430
Lys Tyr Leu Arg Leu Pro Tyr Pro Phe Ser Asn Lys Gln Val Asp Lys
                435                 440                 445
Tyr Leu Leu Arg Pro Leu Gly Pro His Gly Leu Leu Ser Lys Ser Val
        450                 455                 460
Gln Leu Asn Gly Leu Thr Leu Lys Met Val Asp Asp Gln Thr Leu Pro
465                 470                 475                 480
Pro Leu Met Glu Lys Pro Leu Arg Pro Gly Ser Ser Leu Gly Leu Pro
                485                 490                 495
Ala Phe Ser Tyr Ser Phe Phe Val Ile Arg Asn Ala Lys Val Ala Ala
                500                 505                 510
Cys Ile

<210> SEQ ID NO 24
<211> LENGTH: 1710
<212> TYPE: DNA
<213> ORGANISM: Homo sapiens

<400> SEQUENCE: 24
aggagaaaag ggcgctgggg ctcggcggga ggaagtgcta gagctctcga ctctccgctg     60
cgcggcagct ggcgggggga gcagccaggt gagcccaaga tgctgctgcg ctcgaagcct    120
gcgctgccgc cgccgctgat gctgctgctc ctggggccgc tggtcccct ctcccctggc    180
gccctgcccc gacctgcgca agcacaggac gtcgtggacc tggacttctt cacccaggag    240
ccgctgcacc tggtgagccc ctcgttcctg tccgtcacca ttgacgccaa cctggccacg    300
gacccgcggt tcctcatcct cctgggttct ccaaagcttc gtaccttggc cagaggcttg    360
tctcctgcgt acctgaggtt tggtggcacc aagacagact tcctaatttt cgatcccaag    420
aaggaatcaa cctttgaaga gagaagttac tggcaatctc aagtcaacca ggatatttgc    480
aaatatggat ccatccctcc tgatgtggag gagaagttac ggttggaatg ccctaccag    540
gagcaattgc tactccgaga acactaccag aaaaagttca gaacagcac ctactcaaga    600

```
agctctgtag atgtgctata cacttttgca aactgctcag gactggactt gatctttggc    660
ctaaatgcgt tattaagaac agcagatttg cagtggaaca gttctaatgc tcagttgctc    720
ctggactact gctcttccaa ggggtataac atttcttggg aactaggcaa tgaacctaac    780
agtttcctta agaaggctga tattttcatc aatgggtcgc agttaggaga agattttatt    840
caattgcata aacttctaag aaagtccacc ttcaaaaatg caaaactcta tggtcctgat    900
gttggtcagc ctcgaagaaa gacggctaag atgctgaaga gctactattt gaatggacgg    960
actgctacca gggaagattt tctaaaccct gatgtattgg acattttat  ttcatctgtg   1020 caaaaagttt tccaggtggt tgagagcacc aggcctggca agaaggtctg gttaggagaa   1080
acaagctctg catatggagg cggagcgccc ttgctatccg acacctttgc agctggcttt   1140
atgtggctgg ataaattggg cctgtcagcc cgaatgggaa tagaagtggt gatgaggcaa   1200
gtattctttg gagcaggaaa ctaccattta gtggatgaaa acttcgatcc tttacctgat   1260
tattggctat ctcttctgtt caagaaattg gtgggcacca aggtgttaat ggcaagcgtg   1320
caaggttcaa agagaaggaa gcttcgagta taccttcatt gcacaaacac tgacaatcca   1380
aggtataaag aaggagattt aactctgtat gccataaacc tccataacgt caccaagtac   1440
ttgcggttac cctatccttt ttctaacaag caagtggata aataccttct aagacctttg   1500
ggacctcatg gattactttc caaatctgtc caactcaatg gtctaactct aaagatggtg   1560
gatgatcaaa ccttgccacc tttaatggaa aaacctctcc ggccaggaag ttcactgggc   1620
ttgccagctt tctcatatag ttttttttgtg ataagaaatg ccaaagttgc tgcttgcatc   1680
tgaaaataaa atatactagt cctgacactg                                     1710
```

<210> SEQ ID NO 25
<211> LENGTH: 481
<212> TYPE: PRT
<213> ORGANISM: Homo sapiens

<400> SEQUENCE: 25

```
Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Arg Ser Val Asp Val Leu
145                 150                 155                 160

Tyr Thr Phe Ala Asn Cys Ser Gly Leu Asp Leu Ile Phe Gly Leu Asn
                165                 170                 175

Ala Leu Leu Arg Thr Ala Asp Leu Gln Trp Asn Ser Ser Asn Ala Gln
```

```
                  180               185               190
Leu Leu Leu Asp Tyr Cys Ser Ser Lys Gly Tyr Asn Ile Ser Trp Glu
            195                 200                 205
Leu Gly Asn Glu Pro Asn Ser Phe Leu Lys Lys Ala Asp Ile Phe Ile
        210                 215                 220
Asn Gly Ser Gln Leu Gly Glu Asp Phe Ile Gln Leu His Lys Leu Leu
225                 230                 235                 240
Arg Lys Ser Thr Phe Lys Asn Ala Lys Leu Tyr Gly Pro Asp Val Gly
                245                 250                 255
Gln Pro Arg Arg Lys Thr Ala Lys Met Leu Lys Ser Phe Leu Lys Ala
            260                 265                 270
Gly Gly Glu Val Ile Asp Ser Val Thr Trp His His Tyr Tyr Leu Asn
        275                 280                 285
Gly Arg Thr Ala Thr Arg Glu Asp Phe Leu Asn Pro Asp Val Leu Asp
        290                 295                 300
Ile Phe Ile Ser Ser Val Gln Lys Val Phe Gln Val Val Glu Ser Thr
305                 310                 315                 320
Arg Pro Gly Lys Lys Val Trp Leu Gly Glu Thr Ser Ser Ala Tyr Gly
                325                 330                 335
Gly Gly Ala Pro Leu Leu Ser Asp Thr Phe Ala Ala Gly Phe Met Trp
            340                 345                 350
Leu Asp Lys Leu Gly Leu Ser Ala Arg Met Gly Ile Glu Val Val Met
            355                 360                 365
Arg Gln Val Phe Phe Gly Ala Gly Asn Tyr His Leu Val Asp Glu Asn
        370                 375                 380
Phe Asp Pro Leu Pro Asp Tyr Trp Leu Ser Leu Leu Phe Lys Lys Leu
385                 390                 395                 400
Val Gly Thr Lys Val Leu Met Ala Ser Val Gln Gly Ser Lys Arg Arg
                405                 410                 415
Lys Leu Arg Val Tyr Leu His Cys Thr Asn Thr Asp Lys Ser Val Gln
                420                 425                 430
Leu Asn Gly Leu Thr Leu Lys Met Val Asp Asp Gln Thr Leu Pro Pro
            435                 440                 445
Leu Met Glu Lys Pro Leu Arg Pro Gly Ser Ser Leu Gly Leu Pro Ala
        450                 455                 460
Phe Ser Tyr Ser Phe Phe Val Ile Arg Asn Ala Lys Val Ala Ala Cys
465                 470                 475                 480
Ile

<210> SEQ ID NO 26
<211> LENGTH: 1611
<212> TYPE: DNA
<213> ORGANISM: Homo sapiens

<400> SEQUENCE: 26
aggagaaaag ggcgctgggg ctcggcggga ggaagtgcta gagctctcga ctctccgctg      60
cgcggcagct ggcgggggga gcagccaggt gagcccaaga tgctgctgcg ctcgaagcct     120
gcgctgccgc cgccgctgat gctgctgctc ctggggccgc tgggtcccct ctcccctggc     180
gccctgcccc gacctgcgca agcacaggac gtcgtggacc tggacttctt cacccaggag     240
ccgctgcacc tggtgagccc ctcgttcctg tccgtcacca ttgacgccaa cctggccacg     300
gacccgcggt tcctcatcct cctgggttct ccaaagcttc gtaccttggc cagaggcttg     360
tctcctgcgt acctgaggtt tggtggcacc aagacagact tcctaatttt cgatcccaag     420
```

```
aaggaatcaa cctttgaaga gagaagttac tggcaatctc aagtcaacca ggatatttgc    480
aaatatggat ccatccctcc tgatgtggag gagaagttac ggttggaatg ccctaccag    540
gagcaattgc tactccgaga acactaccag aaaaagttca agaacagcac ctactcaaga    600
agctctgtag atgtgctata cacttttgca aactgctcag gactggactt gatctttggc    660
ctaaatgcgt tattaagaac agcagatttg cagtggaaca gttctaatgc tcagttgctc    720
ctggactact gctcttccaa ggggtataac atttcttggg aactaggcaa tgaacctaac    780
agtttcctta agaaggctga tattttcatc aatgggtcgc agttaggaga gatttttatt    840
caattgcata aacttctaag aaagtccacc ttcaaaaatg caaaactcta tggtcctgat    900
gttggtcagc ctcgaagaaa gacggctaag atgctgaaga gcttcctgaa ggctggtgga    960
gaagtgattg attcagttac atggcatcac tactatttga atggacggac tgctaccagg   1020
gaagattttc taaaccctga tgtattggac attttttattt catctgtgca aaaagttttc   1080
caggtggttg agagcaccag gcctggcaag aaggtctggt taggagaaac aagctctgca   1140
tatggaggcg agcgcccctt gctatccgac acctttgcag ctggctttat gtggctggat   1200
aaattgggcc tgtcagcccg aatgggaata gaagtggtga tgaggcaagt attctttgga   1260
gcaggaaact accatttagt ggatgaaaac ttcgatcctt tacctgatta ttggctatct   1320
cttctgttca agaaattggt gggcaccaag gtgttaatgg caagcgtgca aggttcaaag   1380
agaaggaagc ttcgagtata ccttcattgc acaaacactg acaaatctgt ccaactcaat   1440
ggtctaactc taaagatggt ggatgatcaa accttgccac cttttaatgga aaaacctctc   1500
cggccaggaa gttcactggg cttgccagct ttctcatata gttttttttgt gataagaaat   1560
gccaaagttg ctgcttgcat ctgaaaataa aatatactag tcctgacact g             1611
```

<210> SEQ ID NO 27
<211> LENGTH: 406
<212> TYPE: PRT
<213> ORGANISM: Homo sapiens

<400> SEQUENCE: 27

Met Leu Leu Leu Gly Pro Leu Gly Pro Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Ala
                85                  90                  95

Asp Ile Phe Ile Asn Gly Ser Gln Leu Gly Glu Asp Phe Ile Gln Leu
            100                 105                 110

His Lys Leu Leu Arg Lys Ser Thr Phe Lys Asn Ala Lys Leu Tyr Gly
        115                 120                 125

Pro Asp Val Gly Gln Pro Arg Arg Lys Thr Ala Lys Met Leu Lys Ser
    130                 135                 140

Phe Leu Lys Ala Gly Gly Glu Val Ile Asp Ser Val Thr Trp His His
145                 150                 155                 160

Tyr Tyr Leu Asn Gly Arg Thr Ala Thr Arg Glu Asp Phe Leu Asn Pro
                165                 170                 175

Asp Val Leu Asp Ile Phe Ile Ser Ser Val Gln Lys Val Phe Gln Val
            180                 185                 190

Val Glu Ser Thr Arg Pro Gly Lys Lys Val Trp Leu Gly Glu Thr Ser
        195                 200                 205

Ser Ala Tyr Gly Gly Ala Pro Leu Leu Ser Asp Thr Phe Ala Ala
    210                 215                 220

Gly Phe Met Trp Leu Asp Lys Leu Gly Leu Ser Ala Arg Met Gly Ile
225                 230                 235                 240

Glu Val Val Met Arg Gln Val Phe Phe Gly Ala Gly Asn Tyr His Leu
                245                 250                 255

Val Asp Glu Asn Phe Asp Pro Leu Pro Asp Tyr Trp Leu Ser Leu Leu
            260                 265                 270

Phe Lys Lys Leu Val Gly Thr Lys Val Leu Met Ala Ser Val Gln Gly
        275                 280                 285

Ser Lys Arg Arg Lys Leu Arg Val Tyr Leu His Cys Thr Asn Thr Asp
    290                 295                 300

Asn Pro Arg Tyr Lys Glu Gly Asp Leu Thr Leu Tyr Ala Ile Asn Leu
305                 310                 315                 320

His Asn Val Thr Lys Tyr Leu Arg Leu Pro Tyr Pro Phe Ser Asn Lys
                325                 330                 335

Gln Val Asp Lys Tyr Leu Leu Arg Pro Leu Gly Pro His Gly Leu Leu
            340                 345                 350

Ser Lys Ser Val Gln Leu Asn Gly Leu Thr Leu Lys Met Val Asp Asp
        355                 360                 365

Gln Thr Leu Pro Pro Leu Met Glu Lys Pro Leu Arg Pro Gly Ser Ser
    370                 375                 380

Leu Gly Leu Pro Ala Phe Ser Tyr Ser Phe Phe Val Ile Arg Asn Ala
385                 390                 395                 400

Lys Val Ala Ala Cys Ile
                405

<210> SEQ ID NO 28
<211> LENGTH: 1386
<212> TYPE: DNA
<213> ORGANISM: Homo sapiens

<400> SEQUENCE: 28
aggagaaaag gcgctgggg ctcggcggga ggaagtgcta gagctctcga ctctccgctg     60
cgcggcagct ggcgggggga gcagccaggt gagcccaaga tgctgctgcg ctcgaagcct    120
gcgctgccgc cgccgctgat gctgctgctc ctggggccgc tgggtcccct ctccctggc    180 gccctgcccc gacctgcgca agcacaggac gtcgtggacc tggacttctt cacccaggag    240
ccgctgcacc tggtgagccc ctcgttcctg tccgtcacca ttgacgccaa cctggccacg    300
gacccgcggt tcctcatcct cctgggttct ccaaagcttc gtaccttggc cagaggcttg    360
tctcctgcgt acctgaggtt tggtggcacc aagacagact tcctaatttt cgatcccaag    420
aaggctgata ttttcatcaa tgggtcgcag ttaggagaag attttattca attgcataaa    480
cttctaagaa agtccacctt caaaaatgca aaactctatg gtcctgatgt tggtcagcct    540
cgaagaaaga cggctaagat gctgaagagc ttcctgaagg ctggtggaga agtgattgat    600
tcagttacat ggcatcacta ctatttgaat ggacggactg ctaccaggga agattttcta    660
aaccctgatg tattggacat ttttatttca tctgtgcaaa aagttttcca ggtggttgag    720
agcaccaggc ctggcaagaa ggtctggtta ggagaaacaa gctctgcata tggaggcgga    780

```
gcgcccttgc tatccgacac ctttgcagct ggctttatgt ggctggataa attgggcctg   840
tcagcccgaa tgggaataga agtggtgatg aggcaagtat tctttggagc aggaaactac   900
catttagtgg atgaaaactt cgatccttta cctgattatt ggctatctct tctgttcaag   960
aaattggtgg gcaccaaggt gttaatggca agcgtgcaag gttcaaagag aaggaagctt  1020
cgagtatacc ttcattgcac aaacactgac aatccaaggt ataagaagg agatttaact   1080 ctgtatgcca taaacctcca taacgtcacc aagtacttgc ggttacccta tcctttttct  1140
aacaagcaag tggataaata ccttctaaga cctttgggac ctcatggatt actttccaaa  1200
tctgtccaac tcaatggtct aactctaaag atggtggatg atcaaacctt gccacccta   1260 atggaaaaac ctctccggcc aggaagttca ctgggcttgc cagctttctc atatagtttt  1320
tttgtgataa gaaatgccaa agttgctgct tgcatctgaa aataaaatat actagtcctg  1380
acactg                                                              1386

<210> SEQ ID NO 29
<211> LENGTH: 430
<212> TYPE: PRT
<213> ORGANISM: Homo sapiens

<400> SEQUENCE: 29

Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
                20                  25                  30

Gln Glu Pro Leu His Leu Val Ser Pro Ser Phe Leu Ser Val Thr Ile
            35                  40                  45

Asp Ala Asn Leu Ala Thr Asp Pro Arg Phe Leu Ile Leu Leu Gly Ser
        50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Glu
            100                 105                 110

Pro Asn Ser Phe Leu Lys Lys Ala Asp Ile Phe Ile Asn Gly Ser Gln
        115                 120                 125

Leu Gly Glu Asp Phe Ile Gln Leu His Lys Leu Leu Arg Lys Ser Thr
130                 135                 140

Phe Lys Asn Ala Lys Leu Tyr Gly Pro Asp Val Gly Gln Pro Arg Arg
145                 150                 155                 160

Lys Thr Ala Lys Met Leu Lys Ser Phe Leu Lys Ala Gly Gly Glu Val
                165                 170                 175

Ile Asp Ser Val Thr Trp His His Tyr Tyr Leu Asn Gly Arg Thr Ala
            180                 185                 190

Thr Arg Glu Asp Phe Leu Asn Pro Asp Val Leu Asp Ile Phe Ile Ser
        195                 200                 205

Ser Val Gln Lys Val Phe Gln Val Val Glu Ser Thr Arg Pro Gly Lys
    210                 215                 220

Lys Val Trp Leu Gly Glu Thr Ser Ser Ala Tyr Gly Gly Gly Ala Pro
225                 230                 235                 240

Leu Leu Ser Asp Thr Phe Ala Ala Gly Phe Met Trp Leu Asp Lys Leu
                245                 250                 255

Gly Leu Ser Ala Arg Met Gly Ile Glu Val Val Met Arg Gln Val Phe
            260                 265                 270
```

```
Phe Gly Ala Gly Asn Tyr His Leu Val Asp Glu Asn Phe Asp Pro Leu
                275                 280                 285
Pro Asp Tyr Trp Leu Ser Leu Leu Phe Lys Lys Leu Val Gly Thr Lys
            290                 295                 300
Val Leu Met Ala Ser Val Gln Gly Ser Lys Arg Arg Lys Leu Arg Val
305                 310                 315                 320
Tyr Leu His Cys Thr Asn Thr Asp Asn Pro Arg Tyr Lys Glu Gly Asp
                325                 330                 335
Leu Thr Leu Tyr Ala Ile Asn Leu His Asn Val Thr Lys Tyr Leu Arg
            340                 345                 350
Leu Pro Tyr Pro Phe Ser Asn Lys Gln Val Asp Lys Tyr Leu Leu Arg
        355                 360                 365
Pro Leu Gly Pro His Gly Leu Leu Ser Lys Ser Val Gln Leu Asn Gly
        370                 375                 380
Leu Thr Leu Lys Met Val Asp Asp Gln Thr Leu Pro Pro Leu Met Glu
385                 390                 395                 400
Lys Pro Leu Arg Pro Gly Ser Ser Leu Gly Leu Pro Ala Phe Ser Tyr
                405                 410                 415
Ser Phe Phe Val Ile Arg Asn Ala Lys Val Ala Ala Cys Ile
                420                 425                 430

<210> SEQ ID NO 30
<211> LENGTH: 1458
<212> TYPE: DNA
<213> ORGANISM: Homo sapiens

<400> SEQUENCE: 30
aggagaaaag gcgcgctgggg ctcggcggga ggaagtgcta gagctctcga ctctccgctg    60
cgcggcagct ggcgggggga gcagccaggt gagcccaaga tgctgctgcg ctcgaagcct   120
gcgctgccgc cgccgctgat gctgctgctc ctggggccgc tggtcccct ctcccctggc    180
gccctgcccc gacctgcgca agcacaggac gtcgtggacc tggacttctt cacccaggag   240
ccgctgcacc tggtgagccc ctcgttcctg tccgtcacca ttgacgccaa cctggccacg   300
gacccgcggt tcctcatcct cctgggttct ccaaagcttc gtaccttggc cagaggcttg   360
tctcctgcgt acctgaggtt tggtggcacc aagacagact tcctaatttt cgatcccaag   420
aaggaatcaa cctttgaaga gagaagttac tggcaatctc aagtcaacca ggaacctaac   480
agtttcctta agaaggctga tatttcatc aatgggtcgc agttaggaga agattttatt    540
caattgcata aacttctaag aaagtccacc ttcaaaaatg caaaactcta tggtcctgat   600
gttggtcagc ctcgaagaaa gacggctaag atgctgaaga gcttcctgaa ggctggtgga   660
gaagtgattg attcagttac atggcatcac tactatttga atggacggac tgctaccagg   720
gaagattttc taaaccctga tgtattggac attttttattt catctgtgca aaaagttttc   780
caggtggttg agagcaccag gcctggcaag aaggtctggt taggagaaac aagctctgca   840
tatggaggcg agcgcccttt gctatccgac acctttgcag ctggctttat gtggctggat   900
aaattgggcc tgtcagcccg aatgggaata gaagtggtga tgaggcaagt attctttgga   960
gcaggaaact accatttagt ggatgaaaac ttcgatcctt acctgattat tggctatctc  1020
ttctgttca agaaattggt gggcaccaag gtgttaatgg caagcgtgca aggttcaaag  1080
agaaggaagc ttcgagtata ccttcattgc acaaacactg acaatccaag gtataaagaa  1140
ggagattaa ctctgtatgc cataaacctc cataacgtca ccaagtactt gcggttaccc  1200
tatccttttt ctaacaagca agtggataaa taccttctaa gacctttggg acctcatgga  1260
```

```
ttactttcca aatctgtcca actcaatggt ctaactctaa agatggtgga tgatcaaacc    1320
ttgccacctt taatggaaaa acctctccgg ccaggaagtt cactgggctt gccagctttc    1380
tcatatagtt tttttgtgat aagaaatgcc aaagttgctg cttgcatctg aaaataaaat    1440
atactagtcc tgacactg                                                  1458

<210> SEQ ID NO 31
<211> LENGTH: 214
<212> TYPE: PRT
<213> ORGANISM: Homo sapiens

<400> SEQUENCE: 31

Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Arg Ser Ser Val Asp Val Leu
145                 150                 155                 160

Tyr Thr Phe Ala Asn Cys Ser Gly Leu Asp Leu Ile Phe Gly Leu Asn
                165                 170                 175

Ala Leu Leu Arg Thr Ala Asp Leu Gln Trp Asn Ser Ser Asn Ala Gln
            180                 185                 190

Leu Leu Leu Asp Tyr Cys Ser Ser Lys Gly Tyr Asn Ile Ser Trp Glu
        195                 200                 205

Leu Gly Asn Ala Thr Ile
    210

<210> SEQ ID NO 32
<211> LENGTH: 1541
<212> TYPE: DNA
<213> ORGANISM: Homo sapiens

<400> SEQUENCE: 32
aggagaaaag ggcgctgggg ctcggcggga ggaagtgcta gagctctcga ctctccgctg     60
cgcggcagct ggcgggggga gcagccaggt gagcccaaga tgctgctgcg ctcgaagcct    120
gcgctgccgc cgccgctgat gctgctgctc ctggggccgc tgggtcccct ctcccctggc    180
gccctgcccc gacctgcgca agcacaggac gtcgtggacc tggacttctt cacccaggag    240
ccgctgcacc tggtgagccc ctcgttcctg tccgtcacca ttgacgccaa cctggccacg    300
gacccgcggt tcctcatcct cctgggttct ccaaagcttc gtaccttggc cagaggcttg    360
tctcctgcgt acctgaggtt tggtggcacc aagacagact tcctaatttt cgatcccaag    420
```

```
aaggaatcaa cctttgaaga gagaagttac tggcaatctc aagtcaacca ggatatttgc    480
aaatatggat ccatccctcc tgatgtggag gagaagttac ggttggaatg ccctaccag    540
gagcaattgc tactccgaga acactaccag aaaaagttca agaacagcac ctactcaaga    600
agctctgtag atgtgctata cacttttgca aactgctcag gactggactt gatctttggc    660
ctaaatgcgt tattaagaac agcagatttg cagtggaaca gttctaatgc tcagttgctc    720
ctggactact gctcttccaa ggggtataac atttcttggg aactaggcaa tgctactatt    780
tgaatggacg gactgctacc agggaagatt ttctaaaccc tgatgtattg gacattttta    840
tttcatctgt gcaaaaagtt ttccaggtgg ttgagagcac caggcctggc aagaaggtct    900
ggttaggaga aacaagctct gcatatggag gcggagcgcc cttgctatcc gacacctttg    960
cagctggctt tatgtggctg ataaaattgg gcctgtcagc ccgaatggga atagaagtgg   1020
tgatgaggca agtattcttt ggagcaggaa actaccattt agtggatgaa aacttcgatc   1080
ctttacctga ttattggcta tctcttctgt tcaagaaatt ggtgggcacc aaggtgttaa   1140
tggcaagcgt gcaaggttca agagaagga agcttcgagt ataccttcat gcacaaaca   1200
ctgacaatcc aaggtataaa gaaggagatt taactctgta tgccataaac ctccataacg   1260
tcaccaagta cttgcggtta ccctatcctt tttctaacaa gcaagtggat aaataccttc   1320
taagaccttt gggacctcat ggattacttt ccaaatctgt ccaactcaat ggtctaactc   1380
taaagatggt ggatgatcaa accttgccac ctttaatgga aaaacctctc cggccaggaa   1440
gttcactggg cttgccagct ttctcatata gtttttttgt gataagaaat gccaaagttg   1500
ctgcttgcat ctgaaaataa aatatactag tcctgacact g                       1541
```

<210> SEQ ID NO 33
<211> LENGTH: 218
<212> TYPE: PRT
<213> ORGANISM: Homo sapiens

<400> SEQUENCE: 33

```
Met Leu Leu Leu Leu Gly Pro Leu Gly Pro Leu Ser Pro Gly Ala Leu
1               5                   10                  15

Pro Arg Pro Ala Gln Ala Gln Asp Val Val Asp Leu Asp Phe Phe Thr
            20                  25                  30

Gln Glu Pro Leu His Leu Val Ser Pro Ser Phe Leu Ser Val Thr Ile
        35                  40                  45

Asp Ala Asn Leu Ala Thr Asp Pro Arg Phe Leu Ile Leu Leu Gly Ser
    50                  55                  60

Pro Lys Leu Arg Thr Leu Ala Arg Gly Leu Ser Pro Ala Tyr Leu Arg
65                  70                  75                  80

Phe Gly Gly Thr Lys Thr Asp Phe Leu Ile Phe Asp Pro Lys Lys Glu
                85                  90                  95

Ser Thr Phe Glu Glu Arg Ser Tyr Trp Gln Ser Gln Val Asn Gln Asp
            100                 105                 110

Ile Cys Lys Tyr Gly Ser Ile Pro Pro Asp Val Glu Glu Lys Leu Arg
        115                 120                 125

Leu Glu Trp Pro Tyr Gln Glu Gln Leu Leu Leu Arg Glu His Tyr Gln
    130                 135                 140

Lys Lys Phe Lys Asn Ser Thr Tyr Ser Arg Ser Ser Val Asp Val Leu
145                 150                 155                 160

Tyr Thr Phe Ala Asn Cys Ser Gly Leu Asp Leu Ile Phe Gly Leu Asn
                165                 170                 175
```

Ala Leu Leu Arg Thr Ala Asp Leu Gln Trp Asn Ser Ser Asn Ala Gln
            180                 185                 190

Leu Leu Leu Asp Tyr Cys Ser Ser Lys Gly Tyr Asn Ile Ser Trp Glu
            195                 200                 205

Leu Gly Asn Asp Leu Ser Asn Ser Met Val
            210                 215

<210> SEQ ID NO 34
<211> LENGTH: 959
<212> TYPE: DNA
<213> ORGANISM: Homo sapiens

<400> SEQUENCE: 34
aggagaaaag ggcgctgggg ctcggcggga ggaagtgcta gagctctcga ctctccgctg      60
cgcggcagct ggcgggggga gcagccaggt gagcccaaga tgctgctgcg ctcgaagcct     120
gcgctgccgc cgccgctgat gctgctgctc ctggggccgc tgggtcccct ctcccctggc     180
gccctgcccc gacctgcgca agcacaggac gtcgtggacc tggacttctt cacccaggag     240
ccgctgcacc tggtgagccc ctcgttcctg tccgtcacca ttgacgccaa cctggccacg     300
gacccgcggt tcctcatcct cctgggttct ccaaagcttc gtaccttggc cagaggcttg     360
tctcctgcgt acctgaggtt tggtggcacc aagacagact tcctaatttt cgatcccaag     420
aaggaatcaa cctttgaaga gagaagttac tggcaatctc aagtcaacca ggatatttgc     480
aaatatggat ccatccctcc tgatgtggag gagaagttac ggttggaatg ccctaccag     540 gagcaattgc tactccgaga acactaccag aaaaagttca gaacagcac ctactcaaga      600 agctctgtag atgtgctata cacttttgca aactgctcag gactggactt gatctttggc     660
ctaaatgcgt tattaagaac agcagatttg cagtggaaca gttctaatgc tcagttgctc     720
ctggactact gctcttccaa ggggtataac atttcttggg aactaggcaa tgatctgtcc     780
aactcaatgg tctaactcta agatggtgg atgatcaaac cttgccacct ttaatggaaa       840
aacctctccg gccaggaagt tcactgggct tgccagcttt ctcatatagt tttttgtga      900 taagaaatgc caaagttgct gcttgcatct gaaaataaaa tatactagtc ctgacactg      959

<210> SEQ ID NO 35
<211> LENGTH: 573
<212> TYPE: PRT
<213> ORGANISM: mammalian

<400> SEQUENCE: 35

Met Glu Arg Ser Gly Arg Cys Gly Ala Gly Arg Trp Leu Glu Ser
1               5                   10                  15

Arg Thr Arg Ser Pro Ala Gly Gly Ser Arg Gly Ala Ser Ser Leu Gly
                20                  25                  30

Arg Cys Gln Pro Gly Glu Pro Glu Met Leu Arg Leu Ser Leu Leu Leu
            35                  40                  45

Trp Leu Trp Gly Pro Leu Ser Pro Leu Val Gln Cys Ile Leu Ala Ala
        50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

```
Lys Thr Asp Phe Leu Ile Phe Asp Pro Lys Lys Glu Pro Ser His Glu
        130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Asp Phe Lys
            180                 185                 190

Asn Ser Thr Tyr Ser Arg Ser Val Asp Met Leu Tyr Thr Phe Ala
            195                 200                 205

Arg Cys Ser Gly Leu Asp Leu Ile Phe Gly Leu Asn Ala Leu Leu Arg
        210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
                245                 250                 255

Pro Asn Ser Phe Trp Lys Lys Ala His Ile Ser Ile Asp Gly Leu Gln
            260                 265                 270

Leu Gly Glu Asp Tyr Ile Glu Leu His Lys Leu Leu Arg Lys Ser Thr
        275                 280                 285

Leu Lys Asn Val Lys Leu Tyr Gly Pro Asp Val Gly Gln Pro Arg Gly
290                 295                 300

Lys Thr Val Lys Leu Leu Arg Ser Phe Leu Lys Ala Gly Gly Glu Val
305                 310                 315                 320

Ile Asp Ser Val Thr Trp His His Tyr Tyr Leu Asn Gly Arg Ile Ala
                325                 330                 335

Thr Lys Glu Asp Phe Leu Ser Pro Asp Val Leu Asp Thr Phe Ile Leu
            340                 345                 350

Ser Val Gln Lys Ile Leu Gln Val Val Glu Glu Thr Arg Pro Gly Lys
        355                 360                 365

Lys Val Trp Leu Gly Glu Thr Ser Ser Ala Tyr Gly Gly Gly Ala Pro
    370                 375                 380

Leu Leu Ser Asn Thr Phe Ala Ala Gly Phe Met Trp Leu Asp Lys Leu
385                 390                 395                 400

Gly Leu Ser Ala Gln Met Gly Ile Glu Val Val Met Arg Gln Val Phe
                405                 410                 415

Phe Gly Ala Gly Asn Tyr His Leu Val Asp Lys Asn Phe Glu Pro Leu
            420                 425                 430

Pro Asp Tyr Trp Leu Ser Leu Leu Phe Lys Lys Leu Val Gly Ser Lys
        435                 440                 445

Val Leu Met Ala Arg Val Lys Gly Pro Asp Arg Ser Lys Leu Arg Val
    450                 455                 460

Tyr Leu His Cys Thr Asn Ile Asn His Pro Arg Tyr Gln Glu Gly Asp
465                 470                 475                 480

Leu Thr Leu Tyr Ala Leu Asn Leu Tyr Asn Val Thr Lys His Leu Lys
                485                 490                 495

Leu Pro Tyr Gln Leu Phe Asn Lys Pro Val Asp Lys Tyr Leu Val Lys
            500                 505                 510

Pro Leu Gly Pro Gly Leu Leu Ser Lys Ser Val Gln Leu Asn Gly
        515                 520                 525

Gln Ala Leu Lys Met Val Asp Asp Gln Thr Leu Pro Ala Leu Thr Glu
    530                 535                 540

Lys Pro Leu Arg Pro Gly Ser Leu Gly Leu Pro Ala Phe Ser Tyr Gly
```

```
545             550             555             560
Phe Phe Val Ile Arg Asn Ala Lys Val Ala Ala Cys Leu
            565             570
```

<210> SEQ ID NO 36
<211> LENGTH: 2078
<212> TYPE: DNA
<213> ORGANISM: mammalian

<400> SEQUENCE: 36

```
tcagatttgg gcaggctcaa gtgacaaata agtgttttaa ggcagatggg ggtaggggt     60
agcctaaaag ttcaacccag gctttactcc agggccagga atccggtgcc tagtgatggg   120
acctagaaga ggggcagtga gtgcaggaca tcaggaagct aggtcccagc ctctgcgcag   180
tcggggcag tccctcccca ggccgccccg atcttggatc ccggccatct ccgcacccctt   240
cagttgggtg tgggtgatga cgtgaccgcc accaaggga aagctaacac ggaaatggga    300
gagggcgggg aggagaggcg ctgggggcag gatgcagggg aggagtggga gggatggagc   360
gcagtgggag gtgtggagcc gggaggcgct ggcttgagag ccggactcgg agcccggcgg   420
gcggcagcag gggcgccagc tctctgggtc gctgccagcc aggtgagccc gagatgctgc   480
ggctgtcgct gctgctgtgg ctctgggggc cgctcagtcc cctagtccag tgcatcttgg   540
ccgcgcaggc tgaagatgtg gtagagctgg agttctccac ccagcggccg ctgcacctgg   600
tgagtccctc gttcctgtcc atcaccatcg acgccaacct ggccaccgac ccgcggttcc   660
tcaccttcct gggttcccca aaacttcggg ctttggccag aggtttgtct cctgcatacc   720
taagatttgg tggcaccaag acagacttcc ttatttttga ccccaagaag gaaccaagcc   780
atgaagaaag gagttactgg aaatctcaag tgaaccatga tatttgtaga tctggagcca   840
tccctgctgt tgtagtgagg agactacagg tggaatggcc cttccaggag cagttgctac   900
tcagagaaca gtaccaaaaa gattttaaaa acagcactta ctcacgaagc tcagtggaca   960
tgctgtacac gtttgctagg tgctcgggat tggacttgat cttttggtcta aatgcgttac  1020
taagaactgc ggattttcgg tggaacagct ccaatgctca gctcctgctg aactactgct  1080
cttccaagaa ctatgacata tcctgggaac tgggcaatga gcctaatagt ttttggaaga  1140
aggctcacat ttccatcgat ggattgcagt taggagaaga ttatattgag ttgcataagc  1200
ttctaagaaa atcaactctc aaaaatgtga aactctatgg tcctgatgtt ggtcaacctc  1260
gaggaaagac agttaagttg ctgagaagtt tcttgaaggc tggtggagaa gtgattgact  1320
cagttacatg gcatcactac tatttgaatg gacgaattgc taccaaagaa gattttttaa  1380
gccctgatgt tctggacact tttatttat ctgtgcaaaa aattctacag gtggttgagg   1440
agactagacc tggcaagaaa gtctggctgg agagacaag ctctgcatat ggcggtggag   1500
cacccttgct gtccaacacc tttgcagctg gctttatgtg gctggataaa ttgggcctgt   1560
cagcccaaat gggcatagaa gtggtgatga ggcaagtgtt ctttggagct ggaaactacc   1620
acttagtgga taaaaacttc gaacctttac ctgattattg gctgtctctt ctgttcaaga   1680
aactggtggg ttcaaggtg ttaatggcaa gagtgaaagg cccagacaga agcaagcttc   1740
gagtgtacct ccactgcaca aacatcaatc acccaaggta tcaagaagga gatttaactc   1800
tgtacgcctt aaacctttat aatgtcacca agcacttgaa gttaccttat cagttattta   1860
acaaaccagt ggataagtac cttgtaaaac ctttgggacc tggtggatta ctttccaaat   1920
ctgtccaact caatggtcaa gccttgaaga tggtggatga tcaaaccctg ccagctttga   1980
cagaaaagcc tctccgccca ggaagttcac taggcttgcc tgcctttttca tatgggtttt  2040
```
ttgtcataag aaatgccaaa gttgctgctt gtctatga                                    2078

<210> SEQ ID NO 37
<211> LENGTH: 574
<212> TYPE: PRT
<213> ORGANISM: mammalian

<400> SEQUENCE: 37

```
Met Glu Arg Ser Gly Arg Cys Gly Ala Gly Arg Arg Trp Leu Glu Ser
 1               5                  10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Lys Glu Pro Ser His Glu
    130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Glu Phe Lys
            180                 185                 190

Asn Ser Thr Tyr Ser Arg Ser Ser Val Asp Met Leu Tyr Thr Phe Ala
        195                 200                 205

Arg Cys Ser Gly Leu Asp Leu Ile Phe Gly Leu Asn Ala Leu Leu Arg
    210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
                245                 250                 255

Pro Asn Ser Phe Trp Lys Lys Ala His Ile Ser Ile Asp Gly Leu Gln
            260                 265                 270

Leu Gly Glu Asp Tyr Ile Glu Leu His Lys Leu Leu Arg Lys Ser Thr
        275                 280                 285

Leu Lys Asn Val Lys Leu Tyr Gly Pro Asp Val Gly Gln Pro Arg Gly
    290                 295                 300

Lys Thr Val Lys Leu Leu Arg Ser Phe Leu Lys Ala Gly Gly Glu Val
305                 310                 315                 320

Ile Asp Ser Val Thr Trp His His Tyr Tyr Leu Asn Gly Arg Ile Ala
                325                 330                 335

Thr Lys Glu Asp Phe Leu Ser Pro Asp Val Leu Asp Thr Phe Ile Leu
            340                 345                 350

Ser Val Gln Lys Ile Leu Gln Val Glu Glu Thr Arg Pro Gly Lys
        355                 360                 365
```

| Lys | Val | Trp | Leu | Gly | Glu | Thr | Ser | Ser | Ala | Tyr | Gly | Gly | Gly | Ala | Pro |
|---|---|---|---|---|---|---|---|---|---|---|---|---|---|---|---|
|  |  | 370 |  |  |  | 375 |  |  |  | 380 |  |  |  |  |  |

Leu Leu Ser Asn Thr Phe Ala Ala Gly Phe Met Trp Leu Asp Lys Leu
385                 390                 395                 400

Gly Leu Ser Ser Gln Met Gly Ile Glu Val Val Met Arg Gln Val Phe
            405                 410                 415

Phe Gly Ala Gly Asn Tyr His Leu Val Asp Lys Asn Phe Glu Pro Leu
            420                 425                 430

Pro Asp Tyr Trp Leu Ser Leu Leu Phe Lys Lys Leu Val Gly Ser Lys
            435                 440                 445

Val Leu Met Ala Arg Val Lys Gly Pro Asp Arg Ser Lys Leu Arg Val
450                 455                 460

Tyr Leu His Cys Thr Asn Ile Asn His Pro Arg Tyr Gln Glu Gly Asp
465                 470                 475                 480

Leu Thr Leu Tyr Ala Leu Asn Leu Tyr Asn Val Thr Lys His Leu Lys
                485                 490                 495

Leu Pro Tyr Gln Leu Phe Asn Lys Pro Val Asp Lys Tyr Leu Val Lys
            500                 505                 510

Pro Leu Gly Pro Gly Gly Leu Leu Ser Lys Ser Val Gln Leu Asn Gly
            515                 520                 525

Gln Ala Leu Lys Met Val Asp Asp Gln Thr Leu Pro Ala Leu Thr Glu
530                 535                 540

Lys Pro Leu Arg Pro Gly Ser Ser Leu Gly Leu Pro Ala Phe Ser Tyr
545                 550                 555                 560

Gly Phe Phe Val Ile Arg Asn Ala Lys Val Ala Ala Cys Leu
            565                 570

<210> SEQ ID NO 38
<211> LENGTH: 2085
<212> TYPE: DNA
<213> ORGANISM: mammalian

<400> SEQUENCE: 38

```
gtgatttcag attttggctg gctcaagtga caaataagtg ttttaaggca gatgggggta      60
gggggtagcc taaaagttca acccaggctt tactccaggg ccaggaatcc ggtgcctagt     120
gatgggacct agaagaggga cagtgagtgc aggacatcag gaagctaggt cccagcctct     180
gcgcagtcgg gggcagtccc tccccaggcc gccccggatc ttggatcccg gccatctccg     240
caccccttcag ttgggtgtgg gtgatgacgt gaccgccacc aaagggaaag ctaacacgga    300
aatgggagag ggcggggagg agaggcgctg ggggcaggat gcagggagg agtgggaggg      360
atggagcgca gtgggaggtg tggagccggg aggcgctggc ttgagagccg gactcggagc     420
ccggcgggcg gcagcagggg cgccagctct ctgggtcgct gccagccagg tgagcccgag     480
atgctgcggc tgtcgctgct gctgtggctc tggggccgc tcagtcccct agtccagtgc     540
atcttggccg cgcaggctga agatgtggta gagctggagt tctccaccca gcggccgctg     600
cacctggtga gtccctcgtt cctgtccatc accatcgacg ccaacctggc caccgacccg     660
cggttcctca ccttcctggg ttccccaaaa cttcgggctt tggccagagg tttgtctcct     720
gcatacctaa gatttggtgg caccaagaca gacttcctta tttttgaccc caagaaggaa     780
ccaagccatg aagaaggag ttactggaaa tctcaagtga accatgatat tgtagatct       840
ggagccatcc ctgctgttgt agtgaggaga ctacaggtgg aatggcccct tccaggagcag    900
ttgctactca gagaacagta ccaaaaagag tttaaaaaca gcacttactc acgaagctca     960
gtggacatgc tgtacacgtt tgctaggtgc tcgggattgg acttgatctt tggtctaaat    1020
```

```
gcgttactaa gaactgcgga ttttcggtgg aacagctcca atgctcagct cctgctgaac   1080
tactgctctt ccaagaacta tgacatatcc tgggaactgg gcaatgagcc taatagtttt   1140
tggaagaagg ctcacatttc catcgatgga ttgcagttag gagaagatta tattgagttg   1200
cataagcttc taagaaaatc aactctcaaa aatgtgaaac tctatggtcc tgatgttggt   1260
caacctcgag gaaagacagt taagttgctg agaagtttct tgaaggctgg tggagaagtg   1320
attgactcag ttacatggca tcactactat ttgaatggac gaattgctac caaagaagat   1380 ttttttaagcc ctgatgttct ggacactttt atttttatctg tgcaaaaaat tctacaggtg   1440
gttgaggaga ctagacctgg caagaaagtc tggctgggag agacaagctc tgcatatggc   1500
ggtggagcac ccttgctgtc caacaccttt gcagctggct ttatgtggct ggataaattg   1560
ggcctgtcat cccaaatggg catagaagtg gtgatgaggc aagtgttctt tggagctgga   1620
aactaccact tagtggataa aaacttcgaa cctttacctg attattggct gtctcttctg   1680
ttcaagaaac tggtgggttc caaggtgtta atggcaagag tgaaaggccc agacagaagc   1740
aagcttcgag tgtacctcca ctgcacaaac atcaatcacc caaggtatca agaaggagat   1800
ttaactctgt acgccttaaa cctttataat gtcaccaagc acttgaagtt accttatcag   1860
ttatttaaca aaccagtgga taagtacctt gtaaaacctt tgggacctgg tggattactt   1920
tccaaatctg tccaactcaa tggtcaagcc ttgaagatgg tggatgatca aaccctgcca   1980
gctttgacag aaaagcctct ccgcccagga agttcactag gcttgcctgc cttttcatat   2040
gggttttttg tcataagaaa tgccaaagtt gctgcttgtc tatga              2085
```

<210> SEQ ID NO 39
<211> LENGTH: 574
<212> TYPE: PRT
<213> ORGANISM: mammalian

<400> SEQUENCE: 39

```
Met Glu Arg Ser Gly Arg Cys Gly Ala Gly Arg Arg Trp Leu Glu Ser
1               5                   10                  15

Arg Thr Arg Ser Pro Ala Gly Gly Ser Arg Gly Ala Ser Ser Leu Gly
            20                  25                  30

Arg Cys Gln Pro Gly Glu Pro Glu Met Leu Arg Leu Ser Leu Leu Leu
        35                  40                  45

Trp Leu Trp Gly Pro Leu Ser Pro Leu Val Gln Cys Ile Leu Ala Ala
    50                  55                  60

Gln Ala Glu Asp Val Val Glu Leu Glu Phe Ser Thr Gln Arg Pro Leu
65                  70                  75                  80

His Leu Val Ser Pro Ser Phe Leu Ser Ile Thr Ile Asp Ala Asn Leu
                85                  90                  95

Ala Thr Asp Pro Arg Phe Leu Thr Phe Leu Gly Ser Pro Lys Leu Arg
            100                 105                 110

Ala Leu Ala Arg Gly Leu Ser Pro Ala Tyr Leu Arg Phe Gly Gly Thr
        115                 120                 125

Lys Thr Asp Phe Leu Ile Phe Asp Pro Lys Glu Pro Ser His Glu
    130                 135                 140

Glu Arg Ser Tyr Trp Lys Ser Gln Val Asn His Asp Ile Cys Arg Ser
145                 150                 155                 160

Gly Ala Ile Pro Ala Val Val Arg Arg Leu Gln Val Glu Trp Pro
                165                 170                 175

Phe Gln Glu Gln Leu Leu Leu Arg Glu Gln Tyr Gln Lys Glu Phe Lys
            180                 185                 190
```

Asn Ser Thr Tyr Ser Arg Ser Ser Val Asp Met Leu Tyr Thr Phe Ala
        195                 200                 205

Arg Cys Ser Gly Leu Asp Leu Ile Phe Gly Leu Asn Ala Leu Leu Arg
        210                 215                 220

Thr Ala Asp Phe Arg Trp Asn Ser Ser Asn Ala Gln Leu Leu Leu Asn
225                 230                 235                 240

Tyr Cys Ser Ser Lys Asn Tyr Asp Ile Ser Trp Glu Leu Gly Asn Glu
                245                 250                 255

Pro Asn Ser Phe Trp Lys Lys Ala His Ile Ser Ile Asp Gly Leu Gln
                260                 265                 270

Leu Gly Glu Asp Tyr Ile Glu Leu Arg Lys Leu Leu Lys Ser Thr
        275                 280                 285

Leu Lys Asn Val Lys Leu Tyr Gly Pro Asp Val Gly Gln Pro Arg Gly
        290                 295                 300

Lys Thr Val Lys Leu Leu Arg Ser Phe Leu Lys Ala Gly Gly Glu Val
305                 310                 315                 320

Ile Asp Ser Val Thr Trp His His Tyr Tyr Leu Asn Gly Arg Ile Ala
                325                 330                 335

Thr Lys Glu Asp Phe Leu Ser Pro Asp Val Leu Asp Thr Phe Ile Leu
            340                 345                 350

Ser Val Gln Lys Ile Leu Gln Val Val Glu Glu Thr Arg Pro Gly Lys
        355                 360                 365

Lys Val Trp Leu Gly Glu Thr Ser Ser Ala Tyr Gly Gly Gly Ala Pro
        370                 375                 380

Leu Leu Ser Asn Thr Phe Ala Ala Gly Phe Met Trp Leu Asp Lys Leu
385                 390                 395                 400

Gly Leu Ser Ala Gln Met Gly Ile Glu Val Val Met Arg Gln Val Phe
                405                 410                 415

Phe Gly Ala Gly Asn Tyr His Leu Val Asp Lys Asn Phe Glu Pro Leu
            420                 425                 430

Pro Asp Tyr Trp Leu Ser Leu Leu Phe Lys Lys Leu Val Gly Ser Lys
        435                 440                 445

Val Leu Met Ala Arg Val Lys Gly Pro Asp Arg Ser Lys Leu Arg Val
        450                 455                 460

Tyr Leu His Cys Thr Asn Ile Asn His Pro Arg Tyr Gln Glu Gly Asp
465                 470                 475                 480

Leu Thr Leu Tyr Ala Leu Asn Leu Tyr Asn Val Thr Lys His Leu Lys
                485                 490                 495

Leu Pro Tyr Gln Leu Phe Asn Lys Pro Val Asp Lys Tyr Leu Val Ile
                500                 505                 510

Pro Leu Gly Pro Gly Leu Leu Ser Lys Ser Val Gln Leu Asn Gly
        515                 520                 525

Gln Ala Leu Lys Met Val Asp Asp Gln Thr Leu Pro Ala Leu Thr Glu
        530                 535                 540

Lys Pro Leu Arg Pro Gly Ser Ser Leu Gly Leu Pro Ala Phe Ser Tyr
545                 550                 555                 560

Gly Phe Phe Val Ile Arg Asn Ala Lys Val Ala Ala Cys Leu
                565                 570

<210> SEQ ID NO 40
<211> LENGTH: 1794
<212> TYPE: DNA
<213> ORGANISM: mammalian

<400> SEQUENCE: 40

```
atggagcgca gtgggaggtg cggagccggg aggcgctggc ttgagagccg gactcggagc    60
ccggcgggcg gcagcagggg cgccagctct ctgggtcgct gccagccagg tgagcccgag   120
atgctgcggc tgtcgctgct gctgtggctc tggggccgc tcagtcccct agtccagtgc    180
atcttggccg cgcaggctga agatgtggta gagctggagt tctccaccca gcggccgctg   240
cacctggtga gtccctcgtt cctgtccatc accatcgacg ccaacctggc caccgacccg   300
cggttcctca ccttcctggg ttccccaaaa cttcgggctt tggccagagg tttgtctcct   360
gcatacctaa gatttggtgg caccaagaca gacttcctta ttttgaccc caagaaggaa    420
ccaagccatg aagaaaggag ctactggaaa tctcaagtga accatgatat tgtagatct    480
ggagccatcc ctgctgttgt agtgaggaga ctacaggtgg aatggccctt ccaggagcag   540
ttgctactca gagaacagta ccaaaaagag tttaaaaaca gcacttactc acgaagctca   600
gtggacatgc tgtacacgtt tgctaggtgc tcgggattgg acttgatctt tggtctaaat   660
gcgttactaa gaactgcgga ttttcggtgg aacagctcca atgctcagct cctgctgaac   720
tactgctctt ccaagaacta tgacatatcc tgggaactgg gcaatgagcc taatagtttt   780
tggaagaagg ctcacatttc catcgatgga ttgcagttag gagaagatta tattgagttg   840
cgtaagcttc taaaaaaatc aactctcaaa aatgtgaaac tctatggtcc tgatgttggt   900
caacctcgag aaagacagtt aagttgctga gaagtttct tgaaggctgg cggagaagtg    960
attgactcag ttacatggca tcactactat ttgaatggac gaattgctac caagaagat   1020
ttttaagcc ctgatgttct ggacactttt attttatctg tgcaaaaaat tctacaggtg   1080
gttgaggaga ctagacctgg caagaaagtc tggctgggag agacaagctc tgcatatggc   1140
ggtggagcgc ccttgctgtc caacaccttt gcagctggct ttatgtggct ggataaattg   1200
ggcctgtcag cccaaatggg catagaagtg gtgatgaggc aagtgttctt tggagctgga   1260
aactaccact agtggataaa aaacttcgaa ccttttacctg attattggct gtctcttctg   1320
ttcaagaaac tggtgggttc caaggtgtta atggcaagag tgaaaggccc agacagaagc   1380
aagcttcgag tgtacctcca ctgcacaaac atcaatcacc caaggtatca agaaggagat   1440
ttaactctgt acgccttaaa ccttatataat gtcaccaagc acttgaagtt acccttatcag   1500
ttatttaaca aaccagtgga taagtacctt gtaataccctt tgggacctgg tggattactt   1560
tccaaatctg tccaactcaa tggtcaagcc ttgaagatgg tggatgatca aaccctgcca   1620
gctttgacag aaaagcctct ccgcccagga agttcactag gcttgcctgc cttttcatat   1680
gggtttttgt tcataagaaa tgccaaagtt gctgcttgtc tatgaaaata aaaggcaaga   1740
cagttgccat aaaaaaaaaa aacctatagt gagtcgtatt aattctgtgc tcgc         1794
```

<210> SEQ ID NO 41
<211> LENGTH: 1758
<212> TYPE: DNA
<213> ORGANISM: Homo sapiens

<400> SEQUENCE: 41

```
aggagaaaag ggcgctgggg ctcggcggga ggaagtgcta gagctctcga ctctccgctg    60
cgcggcagct ggcgggggga gcagccaggt gagcccaaga tgctgctgcg ctcgaagcct   120
gcgctgccgc cgccgctgat gctgctgctc ctggggccgc tgggtcccct ctcccctggc   180
gccctgcccc gacctgcgca agcacaggac gtcgtggacc tggacttctt cacccaggag   240
ccgctgcacc tggtgagccc ctcgttcctg tccgtcacca ttgacgccaa cctgccacg    300
gacccgcggt tcctcatcct cctgggttct ccaaagcttc gtaccttggc cagaggcttg   360
```

-continued

```
tctcctgcgt acctgaggtt tggtggcacc aagacagact tcctaatttt cgatcccaag    420
aaggaatcaa cctttgaaga gagaagttac tggcaatctc aagtcaacca ggatatttgc    480
aaatatggat ccatccctcc tgatgtggag gagaagttac ggttggaatg ccctaccag     540 gagcaattgc tactccgaga acactaccag aaaaagttca agaacagcac ctactcaaga    600
agctctgtag atgtgctata cacttttgca aactgctcag gactggactt gatctttggc    660
ctaaatgcgt tattaagaac agcagatttg cagtggaaca gttctaatgc tcagttgctc    720
ctggactact gctcttccaa ggggtataac atttcttggg aactaggcaa tgaacctaac    780
agtttcctta agaaggctga tattttcatc aatgggtcgc agttaggaga agatttattt    840
caattgcata aacttctaag aaagtccacc ttcaaaaatg caaaactcta tggtcctgat    900
gttggtcagc ctcgaagaaa gacggctaag atgctgaaga gcttcctgaa ggctggtgga    960
gaagtgattg attcagttac atggcatcac tactatttga atggacggac tgctaccagg   1020
gaagattttc taaaccctga tgtattggac attttttattt catctgtgca aaaagttttc   1080
caggtggttg agagcaccag gcctggcaag aaggtctggt taggagaaac aagctctgca   1140
tatggaggcg gagcgccctt gctatccgac acctttgcag ctggctttat gtggctggat   1200
aaattgggcc tgtcagcccg aatgggaata gaagtggtga tgaggcaagt attctttgga   1260
gcaggaaact accatttagt ggatgaaaac ttcgatcctt tacctgatta ttggctatct   1320
cttctgttca agaaattggt gggcaccaag gtgttaatgg caagcgtgca aggttcaaag   1380
agaaggaagc ttcgagtata ccttcattgc acaaacactg acaatccaag gtataaagaa   1440
ggagatttaa ctctgtatgc cataaacctc cataacgtca ccaagtactt gcggttaccc   1500 tatcctttt ctaacaagca agtggataaa taccttctaa gacctttggg acctcatgga   1560
ttactttcca aatctgtcca actcaatggt ctaactctaa agatggtgga tgatcaaacc   1620
ttgccacctt taatggaaaa acctctccgg ccaggaagtt cactgggctt gccagctttc   1680
tcatatagtt tttttgtgat aagaaatgcc aaagttgctg cttgcatctg aaaataaaat   1740
atactagtcc tgacactg                                                 1758
```

```
<210> SEQ ID NO 42
<211> LENGTH: 22
<212> TYPE: DNA
<213> ORGANISM: Artificial
<220> FEATURE:
<223> OTHER INFORMATION: Synthetic

<400> SEQUENCE: 42
tcagatttgg gctggctcaa gt                                             22

<210> SEQ ID NO 43
<211> LENGTH: 19
<212> TYPE: DNA
<213> ORGANISM: Artificial
<220> FEATURE:
<223> OTHER INFORMATION: Synthetic

<400> SEQUENCE: 43
atggagcgca gtgggaggt                                                 19

<210> SEQ ID NO 44
<211> LENGTH: 20
<212> TYPE: DNA
<213> ORGANISM: Artificial
<220> FEATURE:
<223> OTHER INFORMATION: Synthetic
```

```
<400> SEQUENCE: 44
atgctgcggc tgtcgctgct                                              20

<210> SEQ ID NO 45
<211> LENGTH: 22
<212> TYPE: DNA
<213> ORGANISM: Artificial
<220> FEATURE:
<223> OTHER INFORMATION: Synthetic

<400> SEQUENCE: 45
cctcgttcct gtccatcacc at                                           22

<210> SEQ ID NO 46
<211> LENGTH: 21
<212> TYPE: DNA
<213> ORGANISM: Artificial
<220> FEATURE:
<223> OTHER INFORMATION: Synthetic

<400> SEQUENCE: 46
ggaacccagg aaggtgagga a                                            21

<210> SEQ ID NO 47
<211> LENGTH: 25
<212> TYPE: DNA
<213> ORGANISM: Artificial
<220> FEATURE:
<223> OTHER INFORMATION: Synthetic

<400> SEQUENCE: 47
ggtactgttc tctgagtagc aactg                                        25

<210> SEQ ID NO 48
<211> LENGTH: 21
<212> TYPE: DNA
<213> ORGANISM: Artificial
<220> FEATURE:
<223> OTHER INFORMATION: Synthetic

<400> SEQUENCE: 48
tttaaaaaca gcacttactc a                                            21

<210> SEQ ID NO 49
<211> LENGTH: 23
<212> TYPE: DNA
<213> ORGANISM: Artificial
<220> FEATURE:
<223> OTHER INFORMATION: Synthetic

<400> SEQUENCE: 49
acgtgtacag catgtccact gag                                          23

<210> SEQ ID NO 50
<211> LENGTH: 20
<212> TYPE: DNA
<213> ORGANISM: Artificial
<220> FEATURE:
<223> OTHER INFORMATION: Synthetic

<400> SEQUENCE: 50
atcctgggaa ctgggcaatg                                              20

<210> SEQ ID NO 51
<211> LENGTH: 26
```

```
<212> TYPE: DNA
<213> ORGANISM: Artificial
<220> FEATURE:
<223> OTHER INFORMATION: Synthetic

<400> SEQUENCE: 51
ggtcaacctc gaggaaagac agttaa                                          26

<210> SEQ ID NO 52
<211> LENGTH: 26
<212> TYPE: DNA
<213> ORGANISM: Artificial
<220> FEATURE:
<223> OTHER INFORMATION: Synthetic

<400> SEQUENCE: 52
ttaactgtct ttcctcgagg ttgacc                                          26

<210> SEQ ID NO 53
<211> LENGTH: 22
<212> TYPE: DNA
<213> ORGANISM: Artificial
<220> FEATURE:
<223> OTHER INFORMATION: Synthetic

<400> SEQUENCE: 53
atcacttctc cgccagcctt ca                                              22

<210> SEQ ID NO 54
<211> LENGTH: 22
<212> TYPE: DNA
<213> ORGANISM: Artificial
<220> FEATURE:
<223> OTHER INFORMATION: Synthetic

<400> SEQUENCE: 54
tgaaggctgg cggagaagtg at                                              22

<210> SEQ ID NO 55
<211> LENGTH: 19
<212> TYPE: DNA
<213> ORGANISM: Artificial
<220> FEATURE:
<223> OTHER INFORMATION: Synthetic

<400> SEQUENCE: 55
tggctttatg tggctggat                                                  19

<210> SEQ ID NO 56
<211> LENGTH: 22
<212> TYPE: DNA
<213> ORGANISM: Artificial
<220> FEATURE:
<223> OTHER INFORMATION: Synthetic

<400> SEQUENCE: 56
cataaagcca gctgcaaagg tg                                              22

<210> SEQ ID NO 57
<211> LENGTH: 21
<212> TYPE: DNA
<213> ORGANISM: Artificial
<220> FEATURE:
<223> OTHER INFORMATION: Synthetic

<400> SEQUENCE: 57
agtgtacctc cactgcacaa a                                               21
```

<210> SEQ ID NO 58
<211> LENGTH: 24
<212> TYPE: DNA
<213> ORGANISM: Artificial
<220> FEATURE:
<223> OTHER INFORMATION: Synthetic

<400> SEQUENCE: 58
tcatatgcaa gctgcgactt tggc                                    24

<210> SEQ ID NO 59
<211> LENGTH: 29
<212> TYPE: DNA
<213> ORGANISM: Artificial
<220> FEATURE:
<223> OTHER INFORMATION: Synthetic

<400> SEQUENCE: 59
tcatagacaa gcagcaactt tggcatttc                               29

<210> SEQ ID NO 60
<211> LENGTH: 26
<212> TYPE: DNA
<213> ORGANISM: Artificial
<220> FEATURE:
<223> OTHER INFORMATION: Synthetic

<400> SEQUENCE: 60
ggtcagcctc gaagaaagac ggctaa                                  26

<210> SEQ ID NO 61
<211> LENGTH: 26
<212> TYPE: DNA
<213> ORGANISM: Artificial
<220> FEATURE:
<223> OTHER INFORMATION: Synthetic

<400> SEQUENCE: 61
ttagccgtct tcttcgagg ctgacc                                   26

<210> SEQ ID NO 62
<211> LENGTH: 24
<212> TYPE: DNA
<213> ORGANISM: Artificial
<220> FEATURE:
<223> OTHER INFORMATION: Synthetic

<400> SEQUENCE: 62
tcagatgcaa gcagcaactt tggc                                    24

<210> SEQ ID NO 63
<211> LENGTH: 23
<212> TYPE: DNA
<213> ORGANISM: Artificial
<220> FEATURE:
<223> OTHER INFORMATION: Synthetic

<400> SEQUENCE: 63
ccagaggctt gtctcctgcg tac                                     23

<210> SEQ ID NO 64
<211> LENGTH: 22
<212> TYPE: DNA
<213> ORGANISM: Artificial
<220> FEATURE:
<223> OTHER INFORMATION: Synthetic -continued

<400> SEQUENCE: 64
cctcgttcct gtccgtcacc at                                              22

<210> SEQ ID NO 65
<211> LENGTH: 22
<212> TYPE: DNA
<213> ORGANISM: Artificial
<220> FEATURE:
<223> OTHER INFORMATION: Synthetic

<400> SEQUENCE: 65
agtccaggag caactgagca tt                                              22

<210> SEQ ID NO 66
<211> LENGTH: 22
<212> TYPE: DNA
<213> ORGANISM: Artificial
<220> FEATURE:
<223> OTHER INFORMATION: Synthetic

<400> SEQUENCE: 66
cataaagcca gctgcaaagg tg                                              22

<210> SEQ ID NO 67
<211> LENGTH: 19
<212> TYPE: DNA
<213> ORGANISM: Artificial
<220> FEATURE:
<223> OTHER INFORMATION: Synthetic

<400> SEQUENCE: 67
tggctttatg tggctggat                                                  19

<210> SEQ ID NO 68
<211> LENGTH: 21
<212> TYPE: DNA
<213> ORGANISM: Artificial
<220> FEATURE:
<223> OTHER INFORMATION: Synthetic

<400> SEQUENCE: 68
agtgtacctc cactgcacaa a                                               21

<210> SEQ ID NO 69
<211> LENGTH: 2145
<212> TYPE: DNA
<213> ORGANISM: Artificial Sequence
<220> FEATURE:
<223> OTHER INFORMATION: Synthetic

<400> SEQUENCE: 69
agatttgggc tggctcaagt gacaaataag tgttttaagg cagatggggg taggggtag      60 cctaaaagtt caacccaggc tttactccag ggccaggaat ccggtgccta gtgatgggac     120
ctagaagagg ggcagtgagt gcaggacatc aggaagctag gtcccagcct ctgcgcagtc    180
gggggcagtc cctccccagg ccgccccgat cttggatccc ggccatctcc gcacccttca    240
gttgggtgtg ggtgatgacg tgaccgccac caaagggaaa gctaacacgg aaatgggaga    300
gggcggggag gagaggcgct gggggcagga tgcagggag gagtgggagg gatgagcgc      360 agtgggaggt gcggagccgg gaggcgctgg cttgagagcc ggactcggag cccggcgggc    420
ggcagcaggg gcgccagctc tctggtcgc tgccagccag gtgagcccga gatgctgcgg    480
ctgtcgctgc tgctgtggct ctgggggccg ctcagtcccc tagtccagtg catcttggcc    540

```
gcgcaggctg aagatgtggt agagctggag ttctccaccc agcggccgct gcacctggtg    600
agtccctcgt tcctgtccat caccatcgac gccaacctgg ccaccgaccc gcggttcctc    660
accttcctgg gttccccaaa acttcgggct ttggccagag gtttgtctcc tgcatacctc    720
agatttggtg gcaccaagac agacttcctt attttttgacc ccaagaagga accaagccat    780
gaagaaagga gttactggaa atctcaagtg aaccatgata tttgtagatc tggagccatc    840
cctgctgttg tagtgaggag actacaggtg aatggccct tccaggagca gttgctactc    900
agagaacagt accaaaaaga gtttaaaaac agcacttact cacgaagctc agtggacatg    960
ctgtacacgt ttgctaggtg ctcgggattg gacttgatct ttggtctaaa tgcgttacta    1020
agaactgcgg attttcggtg aacagctcc aatgctcagc tcctgctgaa ctactgctct    1080
tccaagaact atgacatatc ctgggaactg ggcaatgagc ctaatagttt ttggaagaag    1140
gctcacattt ccatcgatgg attgcagtta ggagaagatt atattgagtt gcgtaagctt    1200
ctaagaaaat caactctcaa aaatgtgaaa ctctatggtc ctgatgttgg tcaacctcga    1260
ggaaagacag ttaagttgct gagaagtttc ttgaaggctg gcggagaagt gattgactca    1320
gttacatggc atcactacta tttgaatgga cgaattgcta ccaaagaaga tttttttaagc    1380 cctgatgttc tggacacttt tatttatct gtgcaaaaaa ttctacaggt ggttgaggag    1440
actagacctg gcaagaaagt ctggctggga gagacaagct ctgcatatgg cggtggagca    1500
cccttgctgt ccaacacctt tgcagctggc tttatgtggc tggataaatt gggcctgtca    1560
gcccaaatgg gcatagaagt ggtgatgagg caagtgttct ttggagctgg aaactaccac    1620
ttagtggata aaaacttcga accttttacct gattattggc tgtctcttct gttcaagaaa    1680 ctggtggggtt ccaaggtgtt aatggcaaga gtgaaaggcc cagacagaag caagcttcga    1740
gtgtacctcc actgcacaaa catcaatcac ccaaggtatc aagaaggaga tttaactctg    1800
tacgccttaa acctttataa tgtcaccaag cacttgaagt taccttatca gttatttaac    1860
aaaccagtgg ataagtacct tgtaaaacct ttgggacctg gtggattact ttccaaatct    1920
gtccaactca atggtcaagc cttgaagatg gtggatgatc aaaccctgcc agcttttgaca    1980 gaaaagcctc tcggcccagg aagttcacta ggcttgcctg ccttttcata tgggtttttt    2040
gtcataagaa atgccaaagt tgctgcttgt ctatgaaaat aaaaggcaag acagttgcca    2100 taaaaaaaa aaacctatag tgagtcgtat taattctgtg ctcgc              2145
```

<210> SEQ ID NO 70
<211> LENGTH: 543
<212> TYPE: PRT
<213> ORGANISM: Homo sapiens

<400> SEQUENCE: 70

```
Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
                20                  25                  30

Ala Gln Ala Gln Asp Val Val Asp Leu Asp Phe Phe Thr Gln Glu Pro
            35                  40                  45

Leu His Leu Val Ser Pro Ser Phe Leu Ser Val Thr Ile Asp Ala Asn
        50                  55                  60

Leu Ala Thr Asp Pro Arg Phe Leu Ile Leu Leu Gly Ser Pro Lys Leu
65                  70                  75                  80

Arg Thr Leu Ala Arg Gly Leu Ser Pro Ala Tyr Leu Arg Phe Gly Gly
                85                  90                  95
```

-continued

```
Thr Lys Thr Asp Phe Leu Ile Phe Asp Pro Lys Lys Glu Ser Thr Phe
            100                 105                 110
Glu Glu Arg Ser Tyr Trp Gln Ser Gln Val Asn Gln Asp Ile Cys Lys
        115                 120                 125
Tyr Gly Ser Ile Pro Pro Asp Val Glu Lys Leu Arg Leu Glu Trp
    130                 135                 140
Pro Tyr Gln Glu Gln Leu Leu Leu Arg Glu His Tyr Gln Lys Lys Phe
145                 150                 155                 160
Lys Asn Ser Thr Tyr Ser Arg Ser Ser Val Asp Val Leu Tyr Thr Phe
                165                 170                 175
Ala Asn Cys Ser Gly Leu Asp Leu Ile Phe Gly Leu Asn Ala Leu Leu
            180                 185                 190
Arg Thr Ala Asp Leu Gln Trp Asn Ser Ser Asn Ala Gln Leu Leu Leu
        195                 200                 205
Asp Tyr Cys Ser Ser Lys Gly Tyr Asn Ile Ser Trp Glu Leu Gly Asn
    210                 215                 220
Glu Pro Asn Ser Phe Leu Lys Lys Ala Asp Ile Phe Ile Asn Gly Ser
225                 230                 235                 240
Gln Leu Gly Glu Asp Phe Ile Gln Leu His Lys Leu Leu Arg Lys Ser
                245                 250                 255
Thr Phe Lys Asn Ala Lys Leu Tyr Gly Pro Asp Val Gly Gln Pro Arg
            260                 265                 270
Arg Lys Thr Ala Lys Met Leu Lys Ser Phe Leu Lys Ala Gly Gly Glu
        275                 280                 285
Val Ile Asp Ser Val Thr Trp His His Tyr Tyr Leu Asn Gly Arg Thr
    290                 295                 300
Ala Thr Arg Glu Asp Phe Leu Asn Pro Asp Val Leu Asp Ile Phe Ile
305                 310                 315                 320
Ser Ser Val Gln Lys Val Phe Gln Val Val Glu Ser Thr Arg Pro Gly
                325                 330                 335
Lys Lys Val Trp Leu Gly Glu Thr Ser Ser Ala Tyr Gly Gly Gly Ala
            340                 345                 350
Pro Leu Leu Ser Asp Thr Phe Ala Ala Gly Phe Met Trp Leu Asp Lys
        355                 360                 365
Leu Gly Leu Ser Ala Arg Met Gly Ile Glu Val Val Met Arg Gln Val
    370                 375                 380
Phe Phe Gly Ala Gly Asn Tyr His Leu Val Asp Glu Asn Phe Asp Pro
385                 390                 395                 400
Leu Pro Asp Tyr Trp Leu Ser Leu Leu Phe Lys Lys Leu Val Gly Thr
                405                 410                 415
Lys Val Leu Met Ala Ser Val Gln Gly Ser Lys Arg Arg Lys Leu Arg
            420                 425                 430
Val Tyr Leu His Cys Thr Asn Thr Asp Asn Pro Arg Tyr Lys Glu Gly
        435                 440                 445
Asp Leu Thr Leu Tyr Ala Ile Asn Leu His Asn Val Thr Lys Tyr Leu
    450                 455                 460
Arg Leu Pro Tyr Pro Phe Ser Asn Lys Gln Val Asp Lys Tyr Leu Leu
465                 470                 475                 480
Arg Pro Leu Gly Pro His Gly Leu Leu Ser Lys Ser Val Gln Leu Asn
                485                 490                 495
Gly Leu Thr Leu Lys Met Val Asp Asp Gln Thr Leu Pro Pro Leu Met
            500                 505                 510
Glu Lys Pro Leu Arg Pro Gly Ser Ser Leu Gly Leu Pro Ala Phe Ser
```

```
                515                 520                 525
Tyr Ser Phe Phe Val Ile Arg Asn Ala Lys Val Ala Ala Cys Ile
    530                 535                 540

<210> SEQ ID NO 71
<211> LENGTH: 2078
<212> TYPE: DNA
<213> ORGANISM: Artificial Sequence
<220> FEATURE:
<223> OTHER INFORMATION: Synthetic

<400> SEQUENCE: 71
tcagatttgg gctggctcaa gtgacaaata agtgttttaa ggcagatggg ggtaggggt      60 agcctaaaag ttcaacccag gctttactcc agggccagga atccggtgcc tagtgatggg    120
acctagaaga ggggcagtga gtgcaggaca tcaggaagct aggtcccagc ctctgcgcag    180 tcggggcag tccctcccca ggccgccccg atcttggatc ccggccatct ccgcacccett     240 cagttgggtg tgggtgatga cgtgaccgcc accaagggaa agctaacac ggaaatggga     300 gagggcgggg aggagaggcg ctgggggcag gatgcagggg aggagtggga gggatggagc    360
gcagtgggag gtgcggagcc gggaggcgct ggcttgagag ccggactcgg agcccggcgg    420
gcggcagcag gggcgccagc tctctgggtc gctgccagcc aggtgagccc gagatgctgc    480
ggctgtcgct gctgctgtgg ctctggggc cgctcagtcc cctagtccag tgcatcttgg     540
ccgcgcaggc tgaagatgtg gtagagctgg agttctccac ccagcggccg ctgcacctgg    600
tgagtccctc gttcctgtcc atcaccatcg acgccaacct ggccaccgac ccgcggttcc    660
tcaccttcct gggttcccca aaacttcggg ctttggccag aggtttgtct cctgcatacc    720
taagatttgg tggcaccaag acagacttcc ttattttga ccccaagaag gaaccaagcc     780
atgaagaaag gagttactgg aaatctcaag tgaaccatga tatttgtaga tctggagcca    840
tccctgctgt tgtagtgagg agactacagg tggaatggcc cttccaggag cagttgctac    900
tcagagaaca gtaccaaaaa gagtttaaaa acagcactta ctcacgaagc tcagtggaca    960
tgctgtacac gtttgctagg tgctcgggat tggacttgat ctttggtcta aatgcgttac   1020
taagaactgc ggattttcgg tggaacagct ccaatgctca gctcctgctg aactactgct   1080
cttccaagaa ctatgacata tcctgggaac tgggcaatga gcctaatagt ttttggaaga   1140
aggctcacat ttccatcgat ggattgcagt taggagaaga ttatattgag ttgcgtaagc   1200
ttctaagaaa atcaactctc aaaaatgtga aactctatgg tcctgatgtt ggtcaacctc   1260
gaggaaagac agttaagttg ctgagaagtt tcttgaaggc tggcggagaa gtgattgact   1320
cagttacatg gcatcactac tatttgaatg gacgaattgc taccaaagaa gatttttaa    1380 gccctgatgt tctggacact tttattttat ctgtgcaaaa aattctacag gtggttgagg   1440
agactagacc tggcaagaaa gtctggctgg gagagacaag ctctgcatat ggcggtggag   1500
cacccttgct gtccaacacc tttgcagctg gctttatgtg gctggataaa ttgggcctgt   1560
cagcccaaat gggcatagaa gtggtgatga ggcaagtgtt cttttggagct ggaaactacc   1620 acttagtgga taaaaacttc gaacctttac ctgattattg gctgtctctt ctgttcaaga   1680
aactggtggg ttccaaggtg ttaatggcaa gagtgaaagg cccagacaga agcaagcttc   1740
gagtgtacct ccactgcaca aacatcaatc acccaaggta tcaagaagga gatttaactc   1800
tgtacgcctt aaacctttat aatgtcacca agcacttgaa gttaccttat cagttattta   1860
acaaaccagt ggataagtac cttgtaaaac ctttgggacc tggtgggata cttttccaat   1920
ctgtccaact caatggtcaa gccttgaaga tggtggatga tcaaaccctg ccagctttga   1980
```

```
cagaaaagcc tctcggccca ggaagttcac taggcttgcc tgccttttca tatgggtttt    2040
ttgtcataag aaatgccaaa gtcgcagctt gcatatga                            2078

<210> SEQ ID NO 72
<211> LENGTH: 2078
<212> TYPE: DNA
<213> ORGANISM: Artificial Sequence
<220> FEATURE:
<223> OTHER INFORMATION: Synthetic

<400> SEQUENCE: 72
tcagatttgg gctggctcaa gtgacaaata agtgttttaa ggcagatggg ggtaggggggt    60 agcctaaaag ttcaacccag gctttactcc agggccagga atccggtgcc tagtgatggg   120
acctagaaga ggggcagtga gtgcaggaca tcaggaagct aggtcccagc ctctgcgcag   180 tcggggcag tccctcccca ggccgccccg atcttggatc ccggccatct ccgcaccctt   240
cagttgggtg tgggtgatga cgtgaccgcc accaaaggaa aagctaacac ggaaatggga   300
gagggcgggg aggagaggcg ctgggggcag gatgcagggg aggagtggga gggatggagc   360
gcagtgggag gtgcggagcc gggaggcgct ggcttgagag ccggactcgg agcccggcgg   420
gcggcagcag gggcgccagc tctctgggtc gctgccagcc aggtgagccc gagatgctgc   480
ggctgtcgct gctgctgtgg ctctgggggc cgctcagtcc cctagtccag tgcatcttgg   540
ccgcgcaggc tgaagatgtg gtagagctgg agttctccac ccagcggccg ctgcacctgg   600
tgagtccctc gttcctgtcc atcaccatcg acgccaacct ggccaccgac ccgcggttcc   660
tcaccttcct gggttcccca aaacttcggg ctttggccag aggtttgtct cctgcatacc   720
taagatttgg tggcaccaag acagacttcc ttatttttga ccccaagaag gaaccaagcc   780
atgaagaaag gagttactgg aaatctcaag tgaaccatga tatttgtaga tctggagcca   840
tccctgctgt tgtagtgagg agactacagg tggaatggcc cttccaggag cagttgctac   900
tcagagaaca gtaccaaaaa gagtttaaaa acagcactta ctcacgaagc tcagtggaca   960
tgctgtacac gtttgctagg tgctcgggat tggacttgat ctttggtcta aatgcgttac  1020
taagaactgc ggattttcgg tggaacagct ccaatgctca gctcctgctg aactactgct  1080
cttccaagaa ctatgacata tcctgggaac tgggcaatga gcctaatagt ttttggaaga  1140
aggctcacat ttccatcgat ggattgcagt taggagaaga ttatattgag ttgcgtaagc  1200
ttctaagaaa atcaactctc aaaaatgtga aactctatgg tcctgatgtt ggtcaacctc  1260
gaggaaagac agttaagttg ctgagaagtt tcttgaaggc tggcggagaa gtgattgact  1320
cagttacatg gcatcactac tatttgaatg gacgaattgc taccaaagaa gattttttaa  1380
gccctgatgt tctggacact tttatttat ctgtgcaaaa aattctacag gtggttgagg  1440
agactagacc tggcaagaaa gtctggctgg gagagacaag ctctgcatat ggcggtggag  1500
cacccttgct gtccaacacc tttgcagctg gctttatgtg gctggataaa ttgggcctgt  1560
cagcccaaat gggcatagaa gtggtgatga ggcaagtgtt cttttggagct ggaaactacc  1620 acttagtgga taaaaacttc gaaccttttac ctgattattg gctgtctctt ctgttcaaga  1680
aactggtggg ttccaaggtg ttaatggcaa gagtgaaagg cccagacaga agcaagcttc  1740
gagtgtacct ccactgcaca aacatcaatc acccaaggta tcaagaagga gatttaactc  1800
```

```
tgtacgcctt aaacctttat aatgtcacca agcacttgaa gttaccttat cagttattta    1860
acaaaccagt ggataagtac cttgtaaaac ctttgggacc tggtggatta ctttccaaat    1920
ctgtccaact caatggtcaa gccttgaaga tggtggatga tcaaaccctg ccagctttga    1980
cagaaaagcc tctcggccca ggaagttcac taggcttgcc tgccttttca tatgggtttt    2040
ttgtcataag aaatgccaaa gttgctgctt gcatctga                            2078
```

HEPARANASES AND SPLICE VARIANTS THEREOF, POLYNUCLEOTIDES ENCODING THEM AND USES THEREOF

FIELD OF THE INVENTION

The present invention relates to heparanases and heparanase splice variants, particularly to *Spalax* heparanase and human and *Spalax* heparanase splice variants, to polynucleotides encoding them, and to pharmaceutical compositions and methods comprising said heparanases or polynucleotides.

Abbreviations: ECM: extracellular matrix; HS: Heparan sulfate; HSPGs: Heparan sulfate proteoglycans; SH: *Spalax* heparanase; VEGF: vascular endothelial growth factor.

BACKGROUND OF THE INVENTION

Heparan sulfate proteoglycans (HSPGs) are macromolecules associated with the cell surface and extracellular matrix (ECM) of a wide range of cells of vertebrate and invertebrate tissues (1-3). Heparan sulfate (HS) binds to and assembles ECM proteins and plays important roles in the structural integrity of the ECM and in cell-cell and cell-ECM interactions. HS chains sequester a multitude of proteins and bioactive molecules and thereby function in the control of a large number of normal and pathological processes (1-4). Apart from sequestration of bioactive molecules, HSPGs have a coreceptor role in which the proteoglycan, in concert with the other cell surface molecule, comprises a functional receptor complex that binds the ligand and mediates its action (3-5).

Enzymatic degradation of HS by heparanase, a mammalian endoglucuronidase, affects the integrity and functional state of tissues and is involved in fundamental biological phenomena, ranging from pregnancy, morphogenesis and development to inflammation, angiogenesis and cancer metastasis (6-10). Heparanase elicits an indirect angiogenic response by releasing HS-bound angiogenic growth factors (e.g., basic fibroblast growth factor—bFGF and vascular endothelial growth factor—VEGF) from the ECM and by generating HS fragments that potentiate bFGF receptor binding, dimerization and signaling (5, 8).

By degradating HS of cell surface and ECM, heparanase facilitates locomotion of inflammatory and tumor cells, release growth factors bound to the ECM, and induce new blood vessels formation (angiogenesis). Heparanase expression in tumor cells is correlated with worse prognosis, and its expression in experimental tumor models resulted in increased tumor growth and metastasis formation. Moreover, elevated levels of heparanase have been detected in sera of animals and human cancer patients bearing metastatic tumors, and in the urine of some patients with aggressive metastatic disease. Regulation of heparanase activity in normal tissues is poorly understood.

Despite earlier reports on existence of several distinct mammalian HS-degrading endoglycosidases (heparanases), the cloning of the same single gene (SEQ ID NO: 41) by several groups (6, 7, 11, 12) suggests that mammalian cells express primarily a single dominant functional heparanase enzyme. Since the cloning of human heparanase, no splice variants were described.

Human heparanase is synthesized as a latent 65-kDa precursor whose processing involves proteolytic cleavage and formation of an active enzyme composed of two 50-kDa and 8-kDa subunits (13-15).

Heparanase exhibits endoglycosidase activity at acidic pH (5-6.7), which exists in nonvascularized core of tumor masses. Heparanase mRNA is increased in human breast, colon, lung, prostate, ovary and pancreas tumors compared with the corresponding normal tissues. In human normal tissues, heparanase mRNA expression is limited to the placenta and lymphoid organs.

Because heparanase promotes angiogenesis and cancer progression, the present inventors found of interest to investigate the evolution of this unique enzyme in a wild mammal that was exposed to underground hypoxic stress throughout the family Spalacidae evolutionary history (16).

The subterranean blind mole rat of the genus *Spalax* in Israel, belongs to the superspecies *Spalax ehrenbergi*, consisting of at least 12 allospecies in the Near East. The four Israeli species have been the subject of intensive and extensive interdisciplinary evolutionary studies (16, 17). They represent four species with different diploid chromosome number (2n) associated with four climatic regimes in Israel. These include: *Spalax galili* (2n=52), which lives in the humid-cool upper Galilee mountains; *S. golani* (2n=54), which lives in the semidry, cool Golan heights; *S. carmeli* (2n=58), which ranges in humid-warm central Israel; and *S. judaei* (2n=60), which lives in the dry and warm Samaria, Judea, and the northern Negev (16-18). *Spalax* lives all its life, averaging three years, in sealed underground tunnels (19), evolving a unique adaptive complex to cope with hypoxia and hypercapnia (20, 17).

Among the strategies used by *Spalax* to tolerate hypoxia are: higher myocardial maximal oxygen consumption (21), structural adaptations in tissues that result in a decreased diffusion distance of oxygen to the mitochondria (22), increase in the lung diffusion capacity (22), specific differences in myoglobin which augment oxygen delivery at low oxygen tensions (23), and increased density of blood vessels, correlated with a unique VEGF expression pattern (19, 24, 25). Hemoglobin and hematocrit are higher in the northern species which survive more hypoxia than the southern ones (17).

The present inventors have recently cloned and elucidated the expression of p53 (26, 27) and VEGF (24, 25) in *Spalax*. p53 gene in healthy *Spalax* individuals possesses two amino acid substitutions in its DNA binding domain, identical to mutations found in human tumors. These adaptive substitutions endow *Spalax* p53 with several-fold higher activation of cell arrest and DNA repair genes compared to human p53, and they also favor activation of DNA repair genes over apoptotic genes. Expression of VEGF was constitutively high in *Spalax* muscles, regardless of the oxygen levels, similar to its expression in highly metastatic tumor cells (28) and unlike its levels in rat muscle (25).

SUMMARY OF THE INVENTION

In accordance with the present invention, novel heparanases were found and isolated from the subterranean blind mole rat of the genus *Spalax* (hereinafter "*Spalax*"). The high rate of alternative splicing of the heparanase gene in *Spalax* enabled the identification of *Spalax* heparanase splice variants that until now could not be detected in other species. Based on the these *Spalax* variants, also human heparanase splice variants were isolated and identified.

Thus, in one aspect, the present invention relates to an isolated polypeptide comprising an amino acid sequence selected from:

(a) the amino acid sequence of a heparanase set forth in SEQ ID NO: 1, SEQ ID NO: 35, SEQ ID NO: 37 or SEQ ID NO: 39;

(b) the amino acid sequence of a heparanase splice variant of the sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33, or a fragment thereof;

(c) an amino acid sequence that includes at least about 88.7% amino acid sequence identity with the polypeptide of (a);

(d) an amino acid sequence that includes at least about 67.2% amino acid sequence identity with the polypeptide of (b); or (e) an amino acid sequence encoded by a nucleic acid sequence set forth in SEQ ID NO: 2, SEQ ID NO: 36, SEQ ID NO:38, SEQ ID NO: 40, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34, or by a polypeptide that that hybridizes along at least 85% of its full-length under conditions of high stringency to the coding nucleic acid sequence set forth in SEQ ID NO: 2, SEQ ID NO: 36, SEQ ID NO:38, SEQ ID NO: 40 SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

In another aspect, the present invention relates to an isolated polynucleotide encoding a polypeptide of the invention or a fragment thereof, as defined above.

In one embodiment, the polynucleotide has a nucleic acid sequence encoding a heparanase defined in (a) above such as a polynucleotide of the sequence set forth in SEQ ID NO: 2, SEQ ID NO: 36, SEQ ID NO: 38 or SEQ ID NO: 40. In another embodiment, the polynucleotide has a nucleic acid sequence encoding a heparanase splice variant defined in (b) above such as a polynucleotide of a sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

The invention further includes polynucleotides of a nucleic acid sequence having at least about 60% identity, for example, at least 85% sequence identity, at least 90% sequence identity, at least 95% sequence identity, or at least 99% sequence identity with a nucleic acid sequence identified above as well as polynucleotides encoding the polypeptides of the invention but comprising degenerate codons.

The invention also provides a vector, preferably an expression vector, comprising a polynucleotide of the invention, a host cell comprising said expression vector and a process of producing a polypeptide of the invention comprising culturing said host cell under suitable conditions to express said polypeptide, and isolating the polypeptide from the culture.

The invention further relates to pharmaceutical compositions comprising a polypeptide or a polynucleotide or a vector comprising said polynucleotide of the invention, and a pharmaceutically acceptable carrier.

In one embodiment of the invention, the pharmaceutical composition comprises a polypeptide/heparanase splice variant of the invention capable of downregulating the enzymatic activity of heparanase and is useful for treatment of diseases, disorders and conditions such as, for example, primary tumors and/or prevention or treatment of metastasis.

In another embodiment of the invention, the pharmaceutical composition comprises a *Spalax* heparanase and/or a polypeptide/heparanase splice variant of the invention capable of pro-angiogenic activity and is useful for treatment of diseases, disorders and conditions such as, for example, vascular diseases.

The invention also provides a method for the treatment of a subject suffering from a disease, disorder or condition caused by or associated with the enzymatic activity of heparanase comprising administering to said subject an effective amount of a polypeptide according to the invention, or a polynucleotide encoding said polypeptide or a vector comprising said polynucleotide.

BRIEF DESCRIPTION OF THE FIGURES

FIG. 1 shows nucleotide and predicted amino acid sequences of *Spalax* heparanase. The nucleotide sequence (SEQ ID NO:69) is shown above the predicted amino acid sequence (SEQ ID NO:1). Numbers on the right corresponding to nucleotides (Roman) and amino acid residues (bold italic). The two initiation codons (ATG) and their corresponding methionine residues (M) are in bold. The three potential N-glycosylation sites are shaded. Arrowheads (▲) mark the two cleavage sites generating the two subunits and releasing the linker peptide residing in between. The nucleotide and amino acid sequences lacking in splice variant SH7 are boxed. The hydrophobic potential membrane-spanning domain of 19 amino acids is underlined.

FIG. 2 shows a comparison of *Spalax* (SEQ ID NO:1) and human (SEQ ID NO:70) heparanase amino acid sequences. Vertical lines denote conserved amino acids, and double or single dots mark similar amino acids (Wisconsin Package, Version 103, GCG alignment program). The putative two catalytic Glu residues, the proton donor and the nucleophile, are marked in bold with * above. The potential N-glycosylation sites are shaded. The 8-kDa subunit is marked with a dotted box. The cleavage sites generating the mature enzyme are marked by arrows; amino acids between the two arrows denote the linker sequence. The sequence boxed with a continuous line denotes the amino acids lacking in splice variant 7 of the *Spalax* heparanase.

FIGS. 6A-6H show characterization aspects of *Spalax* heparanase splice variants. (A) schematic presentation of *Spalax* heparanase splice variants. (B) Schematic presentation of *Spalax* heparanase wild-type and splice variants S7, S12, S36. (C) PCR products obtained with primers located around splice variant 7. PCR reaction (color inverted): Lane 1, reaction mixture alone; lane 2, PCR on cDNA of *Spalax* kidney; lane 3, PCR on plasmid containing the wild-type cDNA sequence of *Spalax* heparanase; lane 4, PCR on plasmid containing the spliced form sequence of S7 *Spalax* heparanase. (D) PCR products obtained with primers located around splice variant 12. PCR reaction (color inverted): lane 1, reaction mixture alone; lane 2, PCR on cDNA of *Spalax* kidney; lane 3, PCR on plasmid containing the wild-type cDNA sequence of *Spalax* heparanase; lane 4, PCR on plasmid containing the spliced form sequence of S12 *Spalax* heparanase. (E) PCR products obtained with primers located around splice variant 36. PCR reaction (color inverted): lane 1, reaction mixture alone; lane 2, PCR on cDNA of *Spalax* kidney; lane 3, PCR on plasmid containing the wild-type cDNA sequence of *Spalax* heparanase; lane 4, PCR on plasmid containing the spliced form sequence of S36 *Spalax* heparanase. (F) molecular weight of recombinant *Spalax* heparanases splice variants. Flag sequence was inserted at the 3' end of the cDNA of wild-type, S7, S12, S36 *Spalax* heparanases in pcDNA3. HEK293 cells were transfected with each sequence and blotted with anti flag: lanes:1—transfection with empty vector, 2—wild-type, 3—SH7, 4—SH12, 5—SH36. (G) shows *Spalax Carmeli* heparanase sDNA sequences (SEQ ID NOs:71, 2 and 72) that differ at the 3' end, and the primers location: primers names ending with "F" are forward primes. Primers ending with "b" are backward (reverse) primers. The primers ordered for the "b" primers are the reverse complement sequence of the above nucleotide sequences. Next to the primer's name are the estimated melting temperatures. Nucleotide sequences in boxes are those missing in Splice 36, 7, and 12 respective to the order of their appearance. The junctions between exons are marked by ↑. (H) shows human heparanase sDNA sequence (SEQ ID NO:41), and the primers location: primers names ending with "F" are forward primes. Primers ending with "b" are backward (reverse) primers. The primers ordered for the "b" primers are the reverse complement sequence of the above nucleotide sequences. Next to the primer's name are the estimated melting temperatures. In parentheses is denoted the exon number, and next to it the exon nucleotide number divided by 3 to give the expected amino acid number. The junctions between exons are marked by ↑.

DETAILED DESCRIPTION OF THE INVENTION

Figure 3:
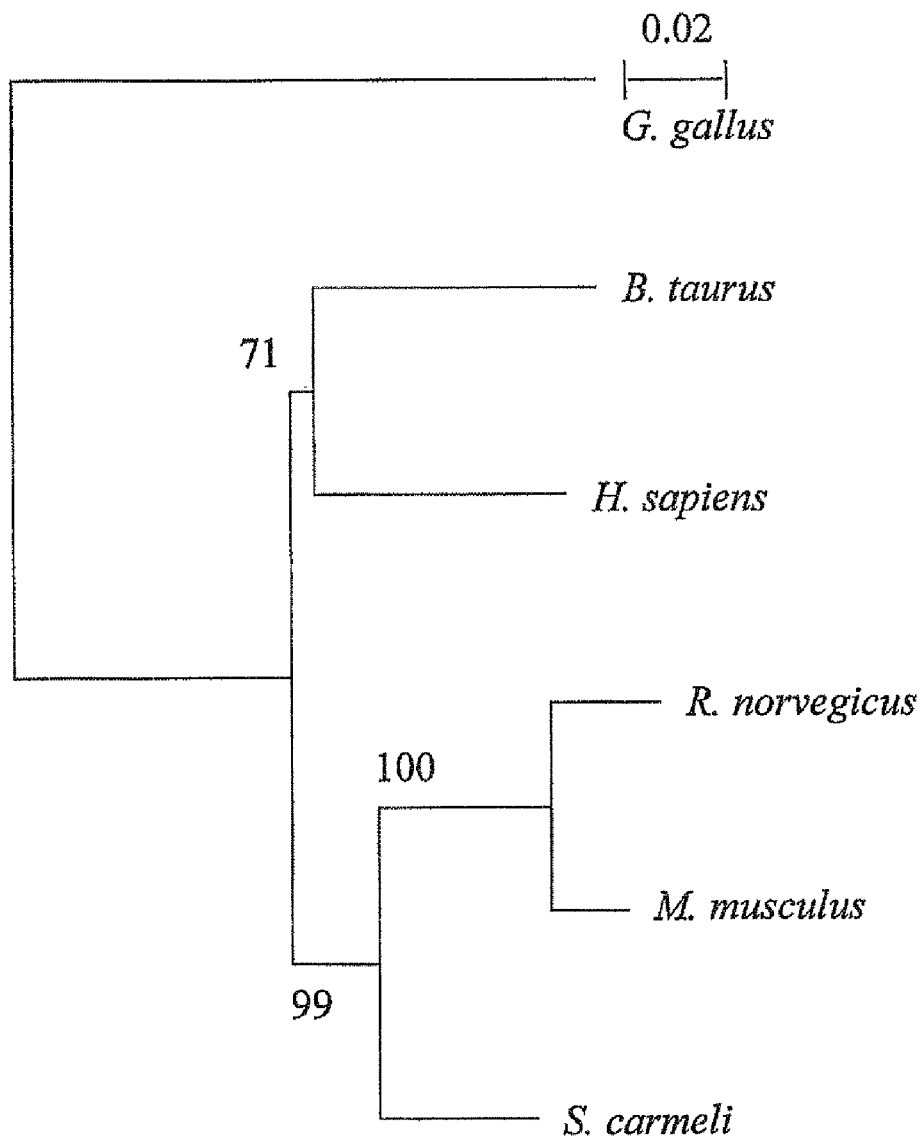
FIG. 3 shows the heparanase similarity tree: an amino acid-based tree using the Kimura distances. The bar represents substitutions per amino acid. The numbers in the junctions are bootstrapping (in percentage) based on 1,000 replications. Alignment of the *Spalax* amino acids sequence with that of the rat, mouse, human, bovine, and chicken shows 86.7%, 88.6%, 85%, 83.7% and 67.2% identity, respectively.

The present invention relates to novel heparanases and to splice variants of mammalian heparanases including, but not limited to, *Spalax* heparanase (SH) and SH splice variants as well as to human heparanase equivalent splice variants, and to their use.

Heparanase plays important roles in several diseases, disorders and conditions such as in cancer, cancer metastasis and angiogenesis (6-10). These roles and the cancer-like expression pattern of VEGF and p53 in *Spalax*, as well as the higher blood vessel density in some tissues of *Spalax* compared to other rodents (19, 23-25), led us to clone the *Spalax* heparanase and to investigate its putative contribution to *Spalax* adaptation to life underground.

Thus, according to the present invention, we identified a unique heparanase splice variant of the enzyme that lacks exon 7 and constitutes, to the best of our knowledge, the first naturally-occurring splice variant of the heparanase-coding region described to date.

The high rate of alternative splicing that we found in *Spalax* enabled the identification of the heparanase splice variants, which until now could not be detected in other species.

The subterranean blind mole rat of the genus *Spalax* in Israel is an excellent model of the twin evolutionary processes of adaptation and speciation (16, 17). The hypoxic, dark, and low productive, energetically stressful environment in which *Spalax* lives resulted in a variety of adaptations in the structural, functional, organismal and molecular levels. Structural adaptations include regression of less important organs (e.g., the eyes which are subcutaneous and atrophic, but still have an active retina used in photoperiodic perception) and progression of others (e.g., big teeth and strong neck muscles needed for underground digging). The hypoxic environment which *Spalax* tissues survive (20) is probably similar to the hypoxic conditions in tumor cores. This may explain the evolution in *Spalax* of physiological variants of oncogenes and angiogenic proteins with similarities to mutations found in human cancer cells (26, 27). For example, our group has recently shown that amino acid substitutions in the *Spalax* p53 gene are identical to known tumor associated mutations (26, 27). VEGF expression in *Spalax* muscle was constitutively high, a pattern similar to its expression in highly metastatic tumor cells (24, 25, 28). Also, erythropoietin expression levels in *Spalax* exhibit a higher increment under hypoxia, relative to other rodents (20). The four allospecies of *Spalax* developed in Israel, share similar morphology but differ in their unique adaptive complex to the different climatic stresses. Major changes in genomic DNA structure resulted in different chromosome number and structure (16, 17).

Figure 4A:
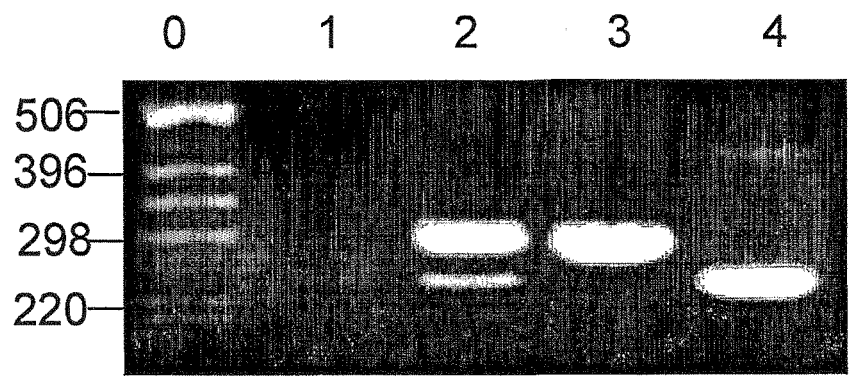
FIGS. 4A-4C show expression of heparanase in different *Spalax* tissues. Semiquantitive RT-PCR using *Spalax*-specific primers located around the heparanase cDNA region encoded by exon 7. Bands of 288 bp represent the wild type enzyme, while those of 240 bp represent its splice variant 7 form. (A). Lane 1, reaction mixture alone; Lane 2, cDNA of kidney of *Spalax Carmeli*; Lanes 3 and 4, plasmids containing the cDNA sequence of the wild type *Spalax* heparanase and the splice 7 variant, respectively. (B). Lane 1, reaction mixture alone; Lanes 2-6, cDNAs of *S. judaei* kidney, liver, heart, brain, and eye, respectively. (C) Comparison of heparanase expression of *S. galili* and *S. judaei* (g or j added to the lane number, respectively). Lane 1, reaction mixture alone; Lanes 2-4, cDNAs from kidney, brain, and liver, respectively. The same cDNA preparations were subjected to RT-PCR using primers specific for *Spalax* β-actin to control for equal loading. Note the higher expression of splice variant 7 in *S. judaei*. DNA ladder lanes are marked by (0). Shown to the left of the DNA ladder are the corresponding number of base pairs.
Figure 4B:
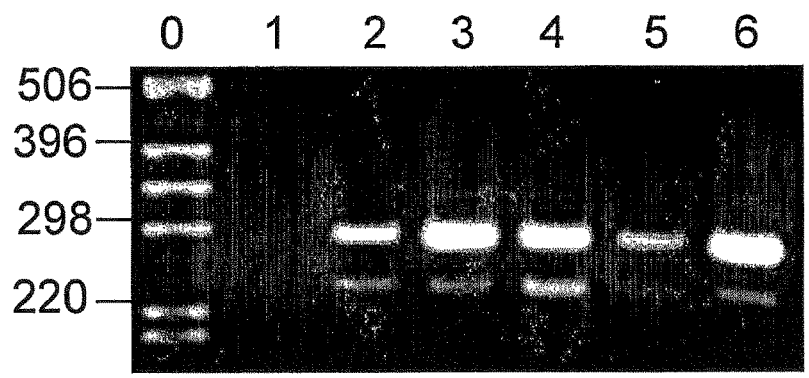

We found in accordance with the invention that heparanase, which in human is expressed mainly in malignant cancer cells, is highly expressed in diverse *Spalax* tissues (FIG. 4B). We demonstrate herein that, despite some differences in sequence, *Spalax* heparanase is as active as the human enzyme in degrading HS in the ECM.

*Spalax* expresses heparanase in a multitude of tissues and may hence contribute to the increased density of blood vessels observed in some of these tissues, relative to mammals residing above ground. Of special interest is the high expression of heparanase in the *Spalax* eye (FIG. 4B, lane 6), which is subcutaneous atrophic and visually blind (16, 17), but still has an active retina used in photoperiodic perception, by responding to signals that penetrate the soil, and is also involved in the circadian rhythm control (40-42).

*Spalax* heparanase possesses fewer N-glycosylation sites than any other described mammalian heparanase. Our results suggest that differences in molecular weights between *Spalax* and human heparanases are primarily due to a lower glycosylation of the *Spalax* protein, which lacks three out of the six N-glycosylation sites of the human heparanase.

We found, in accordance with the present invention, several heparanase splice variants. The DNA sequences of *Spalax* heparanase splice variants SH4, SH5, SH7, SH12, SH36, SH45, SH67, SH612 (SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18, respectively) and the corresponding predicted amino acid sequences (SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO:

17, respectively) were established according to the invention and are disclosed in the sequence listing.

Figure 5A:
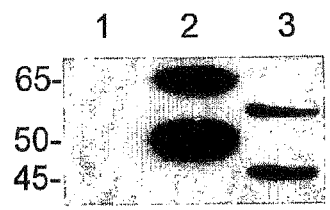
FIGS. 5A-5D show expression, glycosylation, secretion and enzymatic activity of splice variant 7 vs. *Spalax* heparanases. (A-C) Western blots using anti-heparanase antibodies 453 in 5A and 5C and 810 in 5B. (A) Lysates of 293HEK cells transfected with mock (lane 1), human (lane 2), or *Spalax* (lane 3) heparanases. (5B) 293HEK cells transfected with mock (lane 1), human (lanes 2, 4), or *Spalax* (lanes 3, 5) heparanases were preincubated without (lanes 2, 3) or with (lanes 4, 5) tunicamycin. Cell lysates were subjected to SDS-PAGE and Western blotting, as described in "Materials and Methods". Note that the molecular weight difference between the human (lane 2) and *Spalax* (lane 3) heparanases is abolished after treatment with tunicamycin (lanes 4, 5). (C) Comparison of *Spalax* wild-type and splice variant 7 heparanase processing, secretion and heparin binding. First panel: lysates, and second panel: conditioned medium of cells transfected with mock (lane 1), *Spalax* wild-type (lane 2) and splice variant 7 (lane 3) heparanases. Note the lack of processing (first blot) and secretion (second blot) of splice variant 7. The third and fourth blots show heparin-binding capacity. Lysates of 293HEK cells transfected with mock (lanes 1), *Spalax*-wild type (lane 2), or splice variant 7 (lane 3) heparanases were incubated with Fractogel (third blot), as a positive control, or with heparin beads (fourth blot). Proteins remaining bound to the resin and beads after washing were subjected to Western blot analysis using anti-heparanase antibodies, as described in "Material and Methods". Both wild-type and splice 7 *Spalax* heparanases bind to the heparin beads. (D) Heparanase enzymatic activity. Lysates of cell stably transfected with pcDNA3 vectors containing *Spalax* wild type (♦) or splice variant 7 (□) heparanases vs. mock, insert-free plasmid alone (■), were incubated (4 h, 37° C., pH 6.0) with $^{35}$S-labeled ECM. Labeled degradation fragments released into the incubation medium were analyzed by gel filtration on Sepharose 6B. Peak I (fractions 1-10), representing nearly intact HSPGs, was noticed in the mock (■) and splice variant 7 (□) transfected cells. Peak II (fractions 20-30), representing HS degradation products, was obtained in cells transfected with the wild type *Spalax* heparanase (♦).
Figure 5B:
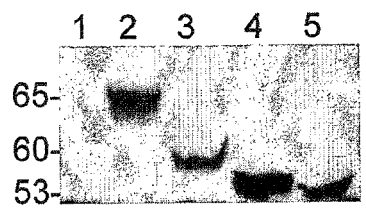
Figure 5C:
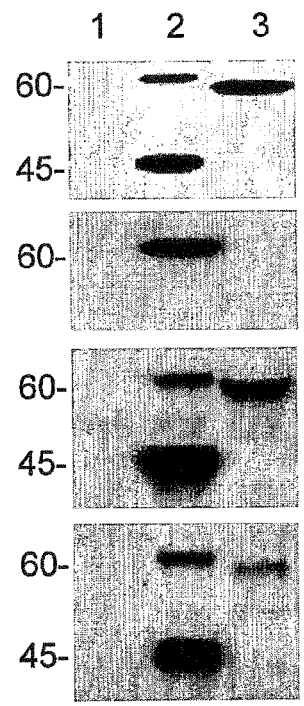
Figure 5D:
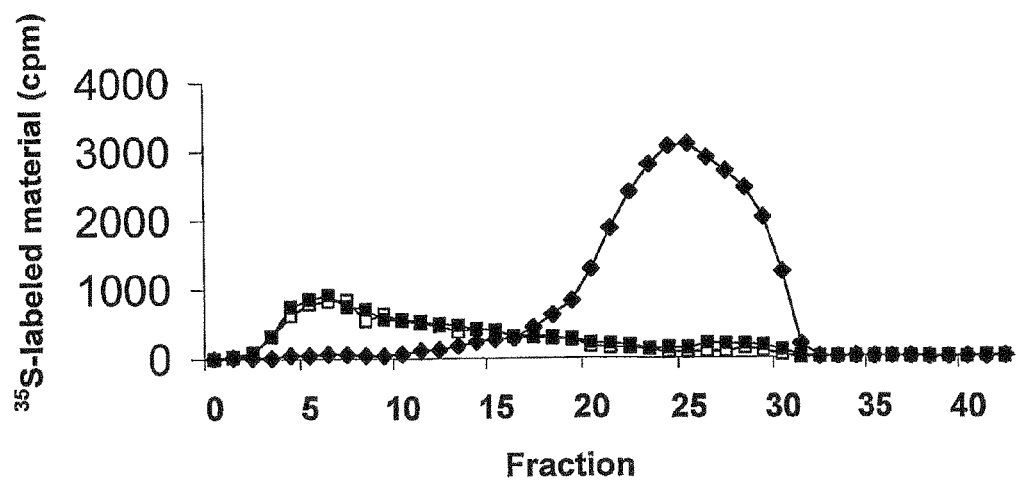

*Spalax* SH7 (SEQ ID NO: 7) is a unique splice variant of heparanase with interspecies variability of its expression. SH7 lacks 48 base pairs that encode 16 amino acids residing between the proton donor (Glu-256) and nucleophile (Glu-374) sites. We found that this deletion did not prevent heparanase binding to heparin (FIG. 5C). Unlike the wild-type heparanase, splice variant SH7 was not detected in the medium of transfected cells (FIG. 5C), suggesting a defect in its secretion. Likewise, processing of splice variant SH7 (i.e., conversion of the latent enzyme into its active form) could not be detected (FIG. 5C) and hence it showed no heparanase enzymatic activity (FIG. 5D). We have also constructed the human homolog of splice variant 7, which exhibits characteristics similar to the *Spalax* splice variant, and succeeded also to clone variant 7 from murine kidney (not shown).

A lower expression of splice variant SH7 was found in *Spalax galili* compared to *S. judaei* (FIG. 4C), which may be due to evolutionary adaptations to the burrow atmosphere differences experienced by these species. Of interest is the high expression of splice variant SH7 in the *Spalax* heart and eye. Alternative splicing may play in *Spalax* a key role in modulating gene functions in response to hypoxic stresses and to the unique evolution of this mammal under diverse fluctuating burrow oxygen levels. Recently, heparanase was shown to be implicated in a variety of non-enzymatic functions (e.g., cell adhesion and survival) (30, 35) that may still be conserved in splice variant SH7.

Several other splice variants of *Spalax* heparanase were identified according to the invention, resulting in expression of truncated forms compared with the wild-type protein. These *Spalax* heparanase splice variants, herein designated SH12, SH36, SH67 and SH612 were analyzed in a similar way as splice variant SH7.

The splice variants SH5, SH7, SH12, SH36, SH67, and SH612 result from skipping of exons #5; #7; #12; part of #3, #4, #5 and part of #6; #6 and #7; and #6, #7, #8, #9, #10, #11 and #12, respectively (see FIG. 6). Splice variants SH5, SH7, SH12, SH36 result from a deletion of a number of nucleic acids that is a multiple of three, hence no frame shift occurs. The predicted amino acid sequence of these variants is thus shorter by 174, 48, 147, and 372 base pairs, respectively, which encode for 58, 16, 49, and 124 amino acids, respectively. Splice variants SH67 and SH612 result in expression of truncated heparanases that possess a unique tail of 3 and 9 amino acids, respectively (FIG. 6).

Splice variant SH36 spans 372 nucleic acids extending upon four exons (3 through 6). This splice variant involves partial skipping of exons 3 and 6, which share the nucleic acid sequence: AAGAAGG. The deletion in splice variant SH36 starts immediately after this sequence occurs in exon #3 and ends exactly after this same sequence finishes in exon #6. The deleted nucleic acids in splice variant SH36 encode the last amino acid of the 8-kDa subunit, the linker sequence (combing the 8- and 45-kDa subunits) and the N-terminus of the 45-kDa subunit including the putative proton donor. Splice variant SH36 lacks two out of the three potential N-glycosylation sites described in the wild-type enzyme.

We found in accordance with the invention that the wild-type *Spalax* heparanase and spliced forms SH7, SH12, and SH36 are expressed in the kidney of *Spalax* and that, while recombinant wild-type heparanase is cleaved and secreted to the medium of transfected HEK293, the recombinant splice variants SH7, SH12 and SH36 are not cleaved in the cells and cannot be detected in the culture medium of transfected cells. We assessed the ability of *Spalax* heparanase and its splice variant, from lysates of transformed cells, to degrade heparan sulfate (HS) in intact ECM and found that H7, H12 and H36 lack heparanase enzymatic activity.

We further found, in accordance with the present invention, that splice variants SH7, SH12 and SH36 have a dominant negative effect on the enzymatic activity of heparanase and therefore can downregulate/inhibit heparanase activity. We evaluated the effect of the splice variants on the ability of endogenous heparanase of B16 melanoma cells to degrade HS, by transfecting the cells with a plasmid containing SH7, SH12, SH36 cDNA or empty vector as a control. The results obtained demonstrated that cells transfected with splice variant SH36, SH12 or SH7 degraded significantly less HS than those transfected with the control vector. With the SH12, we confirmed this result by employing HEK293 cells cotransfected with a plasmid carrying the wild-type *Spalax* heparanase and a plasmid carrying SH12 or empty plasmid and measuring heparanase activity.

We also found in accordance with the invention that splice variant SH36 can inhibit tumor growth in vivo. Due to the role of heparanase in angiogenesis and cancer development and the finding of the invention that splice variants can regulate heparanase activity, we explored the effect of splice variants and wild-type *Spalax* heparanase on tumor development in vivo. Using U87 glioma cells transfected with mock or with a splice variant containing plasmid and measuring tumor growth in subcutaneously injected nude mice, we found that tumors in mice injected with cells harboring splice variant SH36 were less developed than tumors in mice injected with mock containing plasmid. Similar experiments, carried out with different types of tumor cells transfected with SH36 confirmed that SH36 decreases tumor development in vivo. This was evident by smaller tumor size and weight in tumor derived from cell lines transfected with splice variant SH36 relative to controls.

In addition, we found in accordance with the invention that SH36 inhibited lung metastasis formation in a model mice which were injected with B16-BL6 melanoma cells transiently transfected with SH36 containing plasmid or with empty plasmid.

Similar in vivo experiments were carried out with U87 cells transfected with wild-type heparanase, mock, SH36, or SH7 containing plasmid. We observed that the wild-type *Spalax* heparanase as well as SH7 (shown herein to lack heparanase enzymatic activity) are potent inducers of tumor growth (compared with mock).

Based on these results, we anticipated that heparanase splice variants homologous or equivalent to the SH splice variants are present in humans as well. Therefore, we looked for equivalent splice variants to SH5 in human tissue and indeed found the human heparanase (HH) splice variant 5 (HH5) in human kidney. HH5 splice variant originates from splicing out of exon 5, which results in a deletion of 174 bp compared to the wild-type human heparanase cDNA. The reading frame of the splice variant is conserved compared to that of the wild-type gene and its predicted amino acid sequence (HH5, SEQ ID NO: 21) is shorter by 58 residues (485aa for splice 5 compared to 543 aa of the wild-type). HH5 is expressed in human kidney, it is non-cleaved in transfected cells and does not appear in the incubation medium, as opposed to the wild-type latent heparanase protein which accumulates in the medium.

Thus, our results enable identification of human heparanase splice variants. This can be performed, for example, by PCR, using primers around the spliced out exons (e.g. as exemplified below with the SH splice variants and with HH5 variant). Elucidation of HH splice variants function and physiological significance can be found as exemplified below with the SH splice variants.

Examples of herein identified human heparanase splice variants that are equivalent to the *Spalax* splice variants are HH4 (SEQ ID NO: 19), HH5 (SEQ ID NO: 21), HH7 (SEQ ID NO: 23), HH12 (SEQ ID NO: 25), HH36 (SEQ ID NO: 27), HH45 (SEQ ID NO: 29), HH 67 (SEQ ID NO: 31), and HH 612 (SEQ ID NO: 33) and the corresponding nucleic acid sequences encoding them are (SEQ ID NO: 20, SEQ ID NO: 22, SEQ ID NO: 24, SEQ ID NO: 26, SEQ ID NO: 28, SEQ ID NO: 30, SEQ ID NO: 32, and SEQ ID NO: 34, respectively).

In one aspect, the invention provides polypeptides that are heparanases and heparanase splice variants of mammalian origin.

A polypeptide of the invention includes, but is not limited to; each of the four *Spalax* heparanases set forth in SEQ ID NO: 1 (wild-type SH 58 from *S. carmeli*), SEQ ID NO: 35 (wild-type SH 52 from *S. galili*), SEQ ID NO: 37 (wild-type SH 54 from *S. golani*) and SEQ ID NO: 39 (wild-type SH 60 from *S. judaei*); a heparanase homolog having at least or about 88.7% amino acid sequence identity with any of the amino acid sequences set forth in SEQ ID NO: 1, SEQ ID NO: 35, SEQ ID NO: 37 or SEQ ID NO: 39; a heparanase encoded by a polynucleotide of the nucleic acid sequence set forth in SEQ ID NO: 2 (wild-type SH 58 from *S. carmeli*), SEQ ID NO: 36 (wild-type SH 52 from *S. galili*), SEQ ID NO: 38 (wild-type SH 54 from *S. golani*) and SEQ ID NO: 40 (wild-type SH 60 from *S. judaei*) or by a polynucleotide that hybridizes along at least 85% of its full-length under conditions of high stringency to the coding nucleic acid sequence set forth in SEQ ID NO: 2 (wild-type SH 58 from *S. carmeli*), SEQ ID NO: 36 (wild-type SH 52 from *S. galili*), SEQ ID NO: 38 (wild-type SH 54 from *S. golani*) and SEQ ID NO: 40 (wild-type SH 60 from *S. judaei*).

The invention also relates to a polypeptide having at least about 88.7% identity, for example, at least 89% sequence identity, at least 90% sequence identity, at least 95% sequence identity, or at least 99% of amino acid identity to a *Spalax* heparanase.

It should be noted that the definition above is not intended to include and does not include any known heparanase, presently unknown to the Applicants, that may have at least about 88.7% identity, for example, at least 89% sequence identity, at least 90% sequence identity, at least 95% sequence identity, or at least 99% to a *Spalax* heparanase.

The invention also provides polypeptides that are heparanase splice variants of mammalian origin, which include, but are not limited to, the *Spalax* heparanase splice variants set forth in sequence SEQ ID NO: 3 (SH variant 4); SEQ ID NO: 5 (SH variant 5); SEQ ID NO: 7 (SH variant 7); SEQ ID NO: 9 (SH variant 12); SEQ ID NO: 11 (SH variant 36); SEQ ID NO: 13 (SH variant 45); SEQ ID NO: 15 (SH variant 67); SEQ ID NO: 17 (SH variant 612), and the human heparanase (HH) splice variants set forth in sequence SEQ ID NO: 19 (HH variant 4); SEQ ID NO: 21 (HH variant 5); SEQ ID NO: 23 (HH variant 7); SEQ ID NO: 25 (HH variant 12); SEQ ID NO: 27 (HH variant 36); SEQ ID NO: 29 (HH variant 45); SEQ ID NO: 31 (HH variant 67); and SEQ ID NO: 33 (HH variant 612).

Also encompassed by the invention are polypeptides homologous to the heparanase splice variants of the invention, said homolog comprising an amino acid sequence that includes at least 67.2%, for example at least 70%, 83.7%, 85%, 86.7%, or about 88.6% amino acid sequence identity with a SH or HH splice variant polypeptide as identified above. It should be noted that the definition above is not intended to include and does not include any known heparanase splice variant, presently unknown to the Applicants, that may have at least or about 67.2% of amino acid sequence identity to a *Spalax* or human heparanase splice variant.

In some embodiments, the polypeptide is a fragment of a polypeptide of the invention. As used herein, the term "fragment of a polypeptide" refers to a part or fraction of the polypeptide molecule, provided that the shorter peptide retains the desired biological activity of the entire polypetide. Fragments may readily be prepared by removing amino acids from either end of the polypeptide and testing the resulting fragment for its heparanase regulatory activity. Proteases for removing one amino acid at a time from either the N-terminal or the C-terminal of a polypeptide are known, and thus polypeptide fragments that retain the desired biological activity can be obtaining as a matter of routine experimentation.

A polypeptide of the invention includes also a polypeptide having an amino acid sequence encoded by a nucleic acid sequence that hybridizes along at least 85% at least about 86%, for example, at least 89%, at least 90%, at least 95%, or at least 99% of its full-length under conditions of high stringency to the coding nucleic acid sequence set forth in SEQ ID NO: 4 (SH variant 4), SEQ ID NO: 6 (SH variant 5), SEQ ID NO: 8 (SH variant 7), SEQ ID NO: 10 (SH variant 12), SEQ ID NO: 12 (SH variant 36), SEQ ID NO: 14 (SH variant 45), SEQ ID NO: 16 (SH variant 67); SEQ ID NO: 18 (SH variant 612); SEQ ID NO: 20 (HH variant 4), SEQ ID NO: 22 (HH variant 5), SEQ ID NO: 24 (HH variant 7), SEQ ID NO: 26 (HH variant 12), SEQ ID NO: 28 (HH variant 36), SEQ ID NO: 30 (HH variant 45), SEQ ID NO: 32 (HH variant 67) or SEQ ID NO: 34 (HH variant 612). It should be understood that this definition is not intended to include and does not include any known heparanase or polypeptide, presently unknown to the Applicants, which may comprise an amino acid sequence encoded by a nucleic acid sequence that hybridizes along at least 85% at least about 86%, for example, at least 89%, at least 90%, at least 95%, or at least 99% of its full-length under conditions of high stringency to the coding nucleic acid sequence or polynucleotide sequence of a splice variant of the invention.

It should be understood that modified polypeptide molecules having qualitatively the same biological activity of the heparanase, splice variants or fragments of the invention are encompassed herein by the invention. These modified polypeptides include: (i) muteins, analogs in which one or more of the amino acid residues are deleted or replaced by different amino acid residues, and/or one or more amino acid residues are added, without changing considerably the activity of the resulting products as compared with the original protein, and obtained by known synthesis and/or site-directed mutagenesis techniques; (ii) functional derivatives, obtained by chemical substitution of functional groups in side chains of amino acid residues or at the N- and/or C-terminal groups, as long as they remain pharmaceutically acceptable, i.e., they do not destroy the activity of the protein. Such derivatives may, for example, include esters, amides and polyethylene glycol (PEG) side-chains; and (iii) salts, including both salts of carboxyl groups and acid addition salts of amino groups of the polypeptide.

In another aspect, the present invention provides a polynucleotide encoding a polypeptide of the invention or a fragment thereof.

In one embodiment, the polynucleotide codes for a *Spalax* heparanase of the invention and has the sequence set forth in SEQ ID NO: 2, SEQ ID NO: 36, SEQ ID NO: 38 or SEQ ID NO:40. In another embodiment, the polynucleotide codes for a *Spalax* heparanase splice variant of the invention and has the sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18. In a further embodiment, the polynucleotide codes for a human heparanase splice variant of the invention and has the sequence set forth in SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

In another embodiment, the polynucleotide of the invention comprises a sequence that includes at least or about 60% identity, for example, at least 85% sequence identity, at least 90% sequence identity, at least 95% sequence identity, or at least 99% sequence identity with a nucleic acid sequence coding for a *Spalax* heparanase, a *Spalax* heparanase splice variant or a human heparanase splice variant, said nucleic acid having a sequence as set forth hereinabove. It should be understood that this definition is not intended to include and does not include any known polynucleotide, presently unknown to the Applicants, which may comprise a sequence that includes at least or about 60% identity with said nucleic acid sequence of the invention.

The term "nucleic acid molecule" or "polynucleotide" as used herein refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The polynucleotides of the invention include also polynucleotides that comprise degenerate codons and/or which hybridize under highly stringent conditions to the complementary sequences of the sequences set forth hereinabove.

The term "stringent conditions" refers to a temperature and ionic conditions used in a nucleic acid hybridization reaction (See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.). Stringent conditions are sequence dependent and are different under different environmental parameters. Generally, stringent conditions are selected to be about 5 to 10° C. or to 20° C. lower than the thermal melting point (Tm) for the specific sequence at a defined ionic strength and pH. The Tm is the temperature, under defined ionic strength and pH, at which 50% of the target sequence hybridizes to a perfectly matched probe. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions may also be achieved with the addition of destabilizing agents such as formamide. Examples of stringent conditions include washing conditions 5° C. to 10° C. lower than the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes.

The polynucleotides of the invention include also polynucleotides that comprise degenerate codons. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. It will also be recognized that each codon in a polynucleotide, except AUG, which is ordinarily the only codon for methionine, and UUG, which is ordinarily the only codon for tryptophan, can be modified to yield a functionally identical molecule by standard techniques.

Fragments of the polynucleotides of the invention may be used as probes and/or primers to detect the presence of a heparanase splice variant in a sample, for example by Northern blot analysis or PCR. A fragment spanning at least 10, preferably 19-29, consecutive nucleotides, can be used as a primer and a fragment spanning 200-2500 consecutive nucleotides can be used as a probe. According to the invention, a fragment has at least 10, preferably 19-29 or 200-2500 consecutive nucleotides of a nucleic acid sequence that is identical to a sequence of SEQ ID NO: 2, SEQ ID NO: 36, SEQ ID NO: 38, SEQ ID NO:40, SEQ ID NO: 3; SEQ ID NO: 5; SEQ ID NO: 7; SEQ ID NO: 9; SEQ ID NO: 11; SEQ ID NO: 13; SEQ ID NO: 15; SEQ ID NO: 17; SEQ ID NO: 19; SEQ ID NO: 21; SEQ ID NO: 23; SEQ ID NO: 25; SEQ ID NO: 27; SEQ ID NO: 29; SEQ ID NO: 31; and SEQ ID NO: 33.

Examples of polynucleotide fragments according to the invention include, but are not limited, to those set forth in SEQ ID NO: 42 to SEQ ID NO: 67.

Other fragments of the polynucleotides of the invention may be used as small interference RNA (siRNA) to silence or inhibit a heparanase splice variant in a cell. Thus, the invention provides a siRNA comprising between 15 and 30 consecutive nucleotides of a nucleic acid sequence that is identical on the RNA level to a sequence of SEQ ID NO: 2, SEQ ID NO: 36, SEQ ID NO: 38, SEQ ID NO:40, SEQ ID NO: 3; SEQ ID NO: 5; SEQ ID NO: 7; SEQ ID NO: 9; SEQ ID NO: 11; SEQ ID NO: 13; SEQ ID NO: 15, SEQ ID NO: 17; SEQ ID NO: 19; SEQ ID NO: 21; SEQ ID NO: 23; SEQ ID NO: 25; SEQ ID NO: 27; SEQ ID NO: 29; SEQ ID NO: 31; and SEQ ID NO: 33. It should be noted that the invention is not intended to include and does not include any fragment/siRNA that contains a sequence that is present as a continuous stretch of nucleotides in the nucleic acid sequence of known heparanases.

siRNA is widely used for post-transcriptional silencing of specific mRNA targets (46). siRNA consists of double stranded RNA, of 15 and 30 bp long and typically of 9-21 bp long, with two nucleotides overhanging at each 3' end. Alternatively, 27-mer blunt-ended nucleotides may be used (47).

In another aspect, the present invention relates to a vector for containing a polynucleotide encoding a heparanase protein, a heparanase splice variant or a fragment of the foregoing, as defined by the invention, and a host cell containing a polynucleotide or vector. The vector can be a cloning vector or an expression vector, and can be a plasmid vector, viral vector, and the like. Generally, the vector contains a selectable marker independent of that encoded by a polynucleotide of the invention, and further can contain transcription regulatory element such as a promoter or polyadenylation signal sequence, or a translation regulatory element such as a ribosome binding site. A promoter sequence can provide tissue specific expression of a polynucleotide operatively linked thereto.

Also provided is a recombinant nucleic acid molecule, which includes a polynucleotide of the invention operatively linked to one or more other polynucleotides such as transcription and translation regulatory elements. Such a recombinant nucleic acid molecule can be contained in a vector, which can be an expression vector, and the nucleic acid molecule or the vector can be contained in a host cell.

The vector generally contains elements required for replication in a prokaryotic or eukaryotic host system, or both, as desired. Such vectors include plasmid vectors and viral vectors such as bacteriophage, baculovirus and viral vectors developed for use in particular host systems, particularly mammalian systems and include, for example, retroviral vectors, other lentivirus vectors such as those based on the human immunodeficiency virus (HIV), adenovirus vectors, adeno-associated virus vectors, herpes virus vectors, vaccinia virus vectors, and the like. These virus vectors are well known and commercially available.

An expression vector can be transfected into a recombinant host cell for expression of a heparanase protein or variant of the invention. The host cell can be prokaryotic, e.g., bacterial cells, or eukaryotic, e.g., yeast or mammalian cells. The host cells can be selected, for example, for high levels of expression in order to obtain a large amount of isolated protein. A host cell can be maintained in cell culture, or can be a cell in vivo in an organism.

Polypeptides of the invention and fragments thereof, can be produced either in bacterial or eukaryotic host cells transfected, transformed or infected with vectors encoding such polypeptides, or in transgenic animals. When using transgenic animals, it is particularly advantageous to produce heterologous polypeptides in their milk.

Expression of a polypeptides of the invention and fragments thereof in a mammalian cell may be carried out by inserting the DNA encoding the polypeptide into a vector comprising a promoter, optionally an intron sequence and splicing donor/acceptor signals, and further optionally comprising a termination sequence and signal peptide for secretion, by well-known techniques (for example, as described in Current Protocols in Molecular Biology, chapter 16).

The invention further relates to the production of a polypeptide of the invention or a fragment thereof by culturing host cells containing a vector comprising a polynucleotide of the invention or a fragment thereof under suitable conditions to express said polypeptide or fragment thereof, and optionally isolating the polypeptide or fragment from the culture medium.

In another aspect, the present invention relates to antibodies that recognize and bind specifically to a polypeptide or fragment of the invention. This definition excludes antibodies capable of binding also to known heparanases.

The antibodies of the invention may be polyclonal or monoclonal antibodies and can be prepared by methods well-known in the art. These specific antibodies or fragments thereof may be used to detect heparanase splice variants in a sample or to detect cells that express heparanase splice variants. For example, the antibodies may be employed for in situ detection of heparanase splice variants in histological analysis of samples. In situ detection may be accomplished by removing a histological specimen from a patient and contacting the labeled antibody to such a specimen. By using of such a procedure, it is possible to determine the presence of heparanase splice variants and their distribution on the examined tissue.

Antibodies of the invention prepared against *Spalax* wild-type heparanase and/or heparanase splice variants can be used for altering the activity of these proteins inside the cells. For example, a heparanase and/or heparanase splice variant of a cell by may be selectively targeted by transducing the cell with an intracellularly expressed antibody, or intrabody, against the *Spalax* wild-type heparanase and/or heparanase splice variants. The intrabodies can be prepared as disclosed, for example, in WO 99/14353.

It will be understood by the person skilled in the art that it is also possible to shut down heparanase splice variants expression in order to prevent and/or treat diseases by introducing a negative regulation element, like a specific silencing siRNA, leading to downregulation or prevention of heparanase splice variants expression. The person skilled in the art will understand that such down-regulation or silencing of heparanase splice variants expression has the same effect as the use of a heparanase splice variants inhibitor.

A polypeptide of the invention or fragment thereof, a specific antibody, a polynucleotide encoding said polypeptide or fragment thereof, a specific primer such as the ones set forth in SEQ ID NO: 42 to SEQ ID NO: 67 and a probe according to the invention may serve as important diagnostic tools.

Until now, assays measuring heparanase levels in tissues, blood, urine, or other body components and also in experimental systems including tools such as antibodies, real time PCR, and microarrays and others, did not take into consideration the possibility of the presence of splice variants. Hence said assays measuring heparanase levels are aimed to test total heparanase and therefore are not precise. The findings according to the invention make the picture clearer.

Thus, in another aspect, the invention provides assays and kits especially designed for testing specific heparanase splice variants and/or including the wild-type enzyme. Examples for a kit or assay component of the invention include, but is not limited to, antibodies directed to a specific variant or specific nucleic acid such as polynucleotide probes or PCR and sequencing primers allowing detection of the splice variants in a sample as exemplified below in the examples for HH5, SH12, SH7 and SH36.

Using specific assays and kits of the invention, splice variants of human heparanase equivalent to SH variants may be found in association with a human disease, disorder or condition that may then be prevented, treated or alleviated by administrating an agent that is capable of regulating the level of said splice variant. Examples of specific reagents, which can be used to regulate an endogenous splice variant level include, but are not limited to, a splice variant different from the one associated with the disease, disorder or condition, a specific antibody or a small inhibitory molecule such as a variant specific siRNA.

In accordance with the invention, the heparanase splice variants were found to be capable of regulating/modulating heparanase activity. Some of the polypeptides of the invention downregulate/inhibit heparanase activity, while others upregulate/induce heparanase activity.

The results according to the invention indicate that splice variant SH36 is capable of downregulating heparanase activity and can thus be used in treatment or prevention of diseases, disorders or conditions associated with heparanase activity in which the enzyme activity should be downregulated or inhibited such as cancer/tumors including metastasis, inflammatory diseases and disorders and autoimmune diseases.

On the other hand, it is shown in accordance with the invention that SH7 has proangiogenic activity since, regardless the fact that SH7 does not posses heparanase enzymatic activity, tumors removed from mice injected with cells expressing SH7 appear to have augmented vasculature compared to tumors removed from mock control mice. Therefore, *Spalax* variant 7 can be used as a pro-angiogenic agent, for example, in vascular diseases.

Thus, *Spalax* heparanase and *Spalax* splice variants and human heparanase splice variants of the invention can be used to modulate heparanase activity in the treatment of diseases, disorders or conditions in which the enzyme should be either upregulated or down-regulated.

Examples of diseases associated with heparanase activity can be found in U.S. Pat. Nos. 5,968,822, 6,190,875 and WO9940207, which are herewith incorporated by reference in their entirety as if fully disclosed herein.

Diseases, disorders or conditions associated with increased heparanase activity such as malignancies, including both primary tumor and metastasis, may be treated by administering a polypeptide of the invention capable of downregulating/inhibiting the activity of heparanase, such as splice variant 36 (SEQ ID NO: 11 and SEQ ID NO: 27).

Examples of such malignancies include non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, and solid tumors such as tumors in lip and oral cavity, pharynx, larynx, paranasal sinuses, major salivary glands, thyroid gland, esophagus, stomach, small intestine, colon, colorectum, anal canal, liver, gallbladder, extrahepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma, Kaposi's sarcoma and tumors of the central nervous system.

In one preferred embodiment, the heparanase downregulators/inhibitors of the invention are useful for prevention and treatment of metastasis.

Heparanase is involved in inflammation and polypeptides of the invention capable of downregulating/inhibiting heparanase activity such as splice variant 36 (SEQ ID NO: 11 and SEQ ID NO: 27), may be used in the treatment of diseases, disorders and conditions associated with inflammatory processes and autoimmune diseases such as, but not limited to, an opthalmologic disorder such as diabetic retinopathy and macular degeneration, particularly age-related macular degeneration; a cell proliferative disease or disorder such as psoriasis, hypertrophic scars, acne and sclerosis/scleroderma; polyps; multiple exostosis; hereditary exostosis; retrolental fibroplasias; hemangioma; reperfusion of gastric ulcer and arteriovenous malformation; inflammatory symptoms in any disease, condition or disorder where immune and/or inflammation suppression is beneficial such as inflammatory symptoms in the joints, musculoskeletal and connective tissue disorders, inflammatory symptoms associated with hypersensitivity, allergic reactions, asthma, atherosclerosis, otitis and other otorhinolaryngological diseases, dermatitis and other skin diseases, posterior and anterior uveitis, conjunctivitis, optic neuritis, scleritis and other immune and/or inflammatory ophthalmic diseases; or an autoimmune disease such as Eaton-Lambert syndrome, Goodpasture's syndrome, Grave's disease, Guillain-Barré syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjögren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behcet's syndrome, ankylosing spondylitis, pemphigus, bullous pemphigoid, dermatitis herpetiformis, inflammatory bowel diseases including Crohn's disease and ulcerative colitis; or autism.

Heparanase is also implicated in bone formation. Transgenic mice over expressing heparanase have higher bone density. Therefore, polypeptides of the invention capable of inducing/upregulating heparanase activity may be used to treat diseases or disorders associated with decreased bone formation or associated with bone loss such as osteoporosis. On the other hand, splice variants capable of down regulating heparanase, such as splice variant 36 (SEQ ID NO: 11 and SEQ ID NO: 27), can be used to treat Paget's disease, in which there is increased and irregular formation of bone.

Other diseases, disorders or conditions in which a polypeptide of the invention may be useful include neurodegenerative CNS diseases such as Alzheimer's disease and prion diseases, e.g. Jacob-Creutzfeld disease; kidney diseases in which a wild-type heparanase or a splice variant is unregulated leading to proteinuria, minimal change disease or membranous nephropaty; disorders associated with diabetes and pathological angiogenesis, in which the enzymatic activity of heparanase should be downregulated; since heparanase neutralizes the anti coagulation properties of heparin (48), down-regulators can halt undesired degradation of heparin and be useful as antidote to heparanase resistance; viral diseases in which the enzymatic activity of heparanase should be downregulated; wound healing, in which heparanase and/or a heparanase splice variant capable of upregulating the enzymatic heparanase activity may be applied to the wound area alone or bound to a matrix such as a synthetic membrane; diseases in which proangiogenic agents (such as splice variant SH7) are useful, such as ischemic diseases, e.g., coronary vessel diseases, stroke, peripheral vascular diseases, genital vascular diseases and impotence; disorders characterized by lack or excess of hair growth; enhancement of implantation rate of a fertilized egg in in-vitro fertilization procedures by heparanase inducers or inducing abortion at early stages of pregnancy by heparanase inhibitors; hypoxic states such as those found in space and in submarines.

Modulation of an endogenous heparanase splice variant, for example, inhibition of an endogenous splice variant capable of upregulating the enzymatic activity of heparanase, may be useful in some diseases, disorders or conditions. This can be achieved by using a heparanase variant specific siRNA or specific intrabodies of the invention.

Alternatively to the use of a polypeptide of the invention, administration of a a polynucleotide of the invention or a fragment thereof, a vector comprising a polynucleotide of the invention, or a host cell comprising said vector can be used for treatment or prevention of the above-mentioned diseases, disorders or conditions.

In a further aspect, the invention provides a pharmaceutical composition comprising a polypeptide or a fragment thereof of the invention, a polynucleotide or a fragment thereof of the invention, a vector comprising said polynucleotide, or a host cell harboring said vector, and a pharmaceutically acceptable carrier.

The pharmaceutical composition according to the present invention includes a therapeutically effective amount of polypeptides, polynucleotide and/or fragment thereof according to the invention to achieve its intended purpose. In addition, the pharmaceutical compositions may contain suitable pharmaceutically acceptable carriers comprising excipients and auxiliaries such as pharmaceutically acceptable surfactants, excipients, carriers, diluents and vehicles which facilitate processing of the active compounds into preparations and can stabilize such preparations, as well-known in the art.

The compositions according to the invention can be administered to a patient in a variety of ways. Any suitable route of administration is envisaged by the invention such as, but not limited to, intraliver, intradermal, transdermal (e.g. in slow release formulations), intramuscular, intraperitoneal, intravenous, subcutaneous, oral, epidural, topical, and intranasal routes. The composition can be administered together with other biologically active agents.

The definition of "pharmaceutically acceptable" is meant to encompass any carrier, which does not interfere with effectiveness of the biological activity of the active ingredient and that is not toxic to the host to which it is administered. For example, for parenteral administration, the substance according to the invention may be formulated in a unit dosage form for injection in vehicles such as saline, dextrose solution, serum albumin and Ringer's solution.

A "therapeutically effective amount" is such that when administered, the said substances of the invention induce a beneficial effect in therapy. The dosage administered, as single or multiple doses, to an individual may vary depending upon a variety of factors, including the route of administration, patient conditions and characteristics (sex, age, body weight, health, size), extent and severity of symptoms, concurrent treatments, frequency of treatment and the effect desired. Adjustment and manipulation of established dosage ranges are well within the ability of those skilled in the art.

The term "dosage" relates to the determination and regulation of the frequency and number of doses.

In a further aspect, the present invention relates to a method for treatment and/or prevention of a disease, disorder or condition caused by or associated with the enzymatic activity of heparanase, which comprises administering to a subject in need a polypeptide, a polynucleotide, a vector or a host cell according to the invention.

The invention will now be illustrated by the following non-limiting examples.

EXAMPLES

Materials and Methods (i) Animals. The animals used for cloning of the *Spalax* heparanase belong to the four species of the *S. ehrenbergi* superspecies in Israel. All the animals were captured in the field and kept in our animal facility for at least 3 months before use. Animals were housed in individual cages, each species in a separate room. They were kept under controlled conditions at 22-24° C. and fed with carrots and apples. Animals used in this study were adults and ranged in weight from 100-150 g.

(ii) Tissues. Animals were sacrificed by injection of Ketaset CIII (Fort Dodge, Iowa) at 5 mg/kg of body weight. Whole organs were taken out and immediately frozen in liquid nitrogen. The ethics committee of the University of Haifa approved all experiments.

(iii) RNA and cDNA Preparation. Total RNA was extracted from tissues by using TRI Reagent (Molecular Research Center, Cincinnati, Ohio) according to the manufacturer's instructions. cDNA was prepared by reverse transcription (M-MLV reverse transcriptase, Promega, Madison, Wis.) of 1 µg total RNA, using oligo(dT) 15 and random primers (6).

(iv) Gene cloning. For cloning of *Spalax* heparanase, kidney cDNAs from four *Spalax* species were prepared. The open reading frame (ORF) of heparanase was isolated by polymerase chain reactions (PCR) using TaqDNA polymerase (Qbiogene, Illkrich, France). The oligonucleotides (Sigma Genosys, Rehovot, Israel) used for cloning were designed according to published sequences of the mouse, rat and human heparanases (6, 7, 11, 12). *Spalax* heparanase cDNAs were subcloned into the eukaryotic expression plasmid pcDNA3 (Invitrogen, NV Leek, Netherlands) at the EcoRI site. For cloning the 3' end and the 3' untranslated regions (UTR), 3' RACE (RLM-RACE, Ambion, Austin, Tex.) was performed, using the *Spalax* specific sense primer in SEQ ID NO: 68, according to the manufacturer's instructions.

(v) Tissue distribution of the wild type *Spalax* heparanase and its splice variant SH7. Screening of cDNAs from a variety of tissues for expression of wild type heparanase, or its splice variant SH7, was performed by means of PCR. The primers used were located around the *Spalax* heparanase cDNA region encoded by exon 7 (SEQ ID NO: 51, anti-sense SEQ ID NO: 66)

(vi) DNA Sequencing. DNA sequencing was performed using vector-specific and gene-specific primers, with an automated DNA sequencer (ABI Prism™ model 310 Genetic Analyzer, Perkin Elmer, Foster city, Calif.).

(vii) Similarity tree. Protein (amino acids)-based tree was established, using Kimura's protein distance (29) and the neighbor-joining method. The tree is derived from the Wisconsin package version 103 (GCG103, Genetics Computer Group, Madison, Wis., USA).

(vii) Cells and transfections. Human embryonic kidney cells (HEK293) were cultured in Dulbecco's modified Eagle's medium (DMEM, 4.5 gr. glucose/liter) containing 10% fetal calf serum (FCS), and antibiotics, as described (30, 31). Cells were grown in 60 mm tissue culture dishes and transfected with a total of 1-2 µg plasmid DNA mixed with 6 µl of FuGene transfection reagent (Roche Applied Science, Mannheim, Germany) and 94 µl DMEM. Transiently transfected cells were obtained after 24-48 h incubation at 37° C. Stable populations of transfected cells were selected with G418 (6, 30, 31).

Murine B16-BL6 melanoma cells were electroporated with pcDNA vector containing heparanase splice variant SH7, SH36 or empty construct (4×106 cells in 400 µL of medium containing 10 µg of plasmid DNA) by using a single 70-ms pulse at 140 V and an ECM 830 Electro Square porator and disposable cuvettes (model 640, 4-mm gap; BTX, San Diego, Calif.). After electroporation, the transfected cells were plated at a density of 0.4×106 cells per 100-mm dish and allowed to grow for 24-48 hours. Efficiency of transfection (80%) was evaluated 48 hours after electroporation of a vector containing the gene encoding green fluorescent protein by fluorescence microscopy.

(viii) Heparanase activity. Cell lysates prepared from 1×10$^6$ cells by three cycles of freezing and thawing in heparanase reaction buffer (20 mM phosphate-citrate buffer, pH 6.0, 1 mM dithiothreitol, 1 mM $CaCl_2$, and 50 mM NaCl) were incubated (4 h, 37° C., pH 6.0) with $^{35}$S-labeled ECM, prepared as described (6). The incubation medium containing $^{35}$S-labeled HS degradation fragments was analyzed by gel filtration on a Sepharose CL-6B column (6, 31). Fractions (0.2 ml) were eluted with phosphate-buffered saline (PBS) and their radioactivity counted in a β-scintillation counter. Degradation fragments of HS side chains were eluted from Sepharose 6B at $0.5<K_{av}<0.8$ (peak II, fractions 20-30) (6, 31, 32). Each experiment was performed at least three times and the variation in elution positions ($K_{av}$ values) did not exceed ±15% of the mean.

(ix) Western blot analysis. Cells ($2\times10^6$) transfected with either insert free pcDNA3 vector alone, or pcDNA3 containing the *Spalax* heparanase, were lysed in 1 ml lysis buffer containing 50 mM Tris-HCl, pH 7.4, 150 mM NaCl, 0.5% Triton X-100, and a mixture of protease inhibitors (Roche Applied Science, Mannheim, Germany). Heparanase was concentrated by incubating (4° C., 1 h) the cell lysate with ConA beads (Amersham Biosciences, Uppsala, Sweden), or Fractogel (Merck, Darmstadt, Germany) and washing (×2) with PBS (33-35). The beads were boiled (3 min) in sample buffer, centrifuged and the supernatant subjected to SDS-PAGE and immunoblot analysis, using polyclonal anti-heparanase antibodies #1453 or #810 (1:2500), as described (33-35). Antibody #1453 was raised in rabbit against the entire 65 kDa heparanase precursor (35). Antibody #810 was raised in rabbit against the C-terminus of the 8 kDa human heparanase subunit (14, 35). Immunoreactive bands were detected by the enhanced chemiluminescence reagent, as described (6, 33-35).

(x) Experimental and Spontaneous Metastasis. For the experimental metastasis studies, the lateral tail vein of 6-week-old C57BL/6 mice was injected with 0.4 mL of a cell suspension containing $0.4\times10^6$ B16-BL6 melanoma cells transiently transfected with pcDNA vector containing heparanase splice variant SH7, SH36 or empty construct. Fifteen days after cell injection, mice were killed and their lungs were removed, fixed in Bouin's solution, and scored under a dissecting microscope for the number of metastatic nodules on the lung surface. Five mice were used per group.

(xi) PCR reactions and primers. *Spalax* Heparanase Splice 7 was cloned by PCR reaction utilizing the following primers (see FIG. 6G): Mf-3b (see Primers below) on cDNA of *Spalax* kidney, and was screened for by PCR reaction utilizing the primer pair: sMF-M2b. *Spalax* Heparanase Splice 12 was cloned by PCR reaction utilizing the primers: Mf-s3'Lb on cDNA of *Spalax* kidney, and was screened for by PCR reaction utilizing the primer pair: sHep1742f-s3'Lb. *Spalax* Heparanase Splice 36 was cloned by PCR reaction utilizing the primers: M4f-M3b on cDNA of *Spalax* hypoxic kidney. *Spalax* Heparanase Splice 67 was cloned by PCR reaction utilizing the primers: M1f-M2b on cDNA of *Spalax* hypoxic kidney. *Spalax* Heparanase Splice 612 was cloned by PCR reaction utilizing the primers: M4f-s3'Lb on cDNA of *Spalax* hypoxic kidney.

*Spalax* Primers:
5'UTRf: SEQ ID NO: 42, sATG1f: SEQ ID NO: 43, sATG2F: SEQ ID NO: 44, M4f: SEQ ID NO: 45, sM5b: SEQ ID NO: 46, sM8b: SEQ ID NO: 47, M1f: SEQ ID NO: 48, sM9b: SEQ ID NO: 49, sM2F: SEQ ID NO: 50, Mf: SEQ ID NO: 51, Mb: SEQ ID NO: 52, sM3b: SEQ ID NO: 53, sM3F: SEQ ID NO: 54, srmhHep1529f: SEQ ID NO: 55, M2b: SEQ ID NO: 56, sHep1742f: SEQ ID NO: 57, 3'b: SEQ ID NO: 58, sHep 3'Lb: SEQ ID NO: 59.

Figures 6A, 6B:
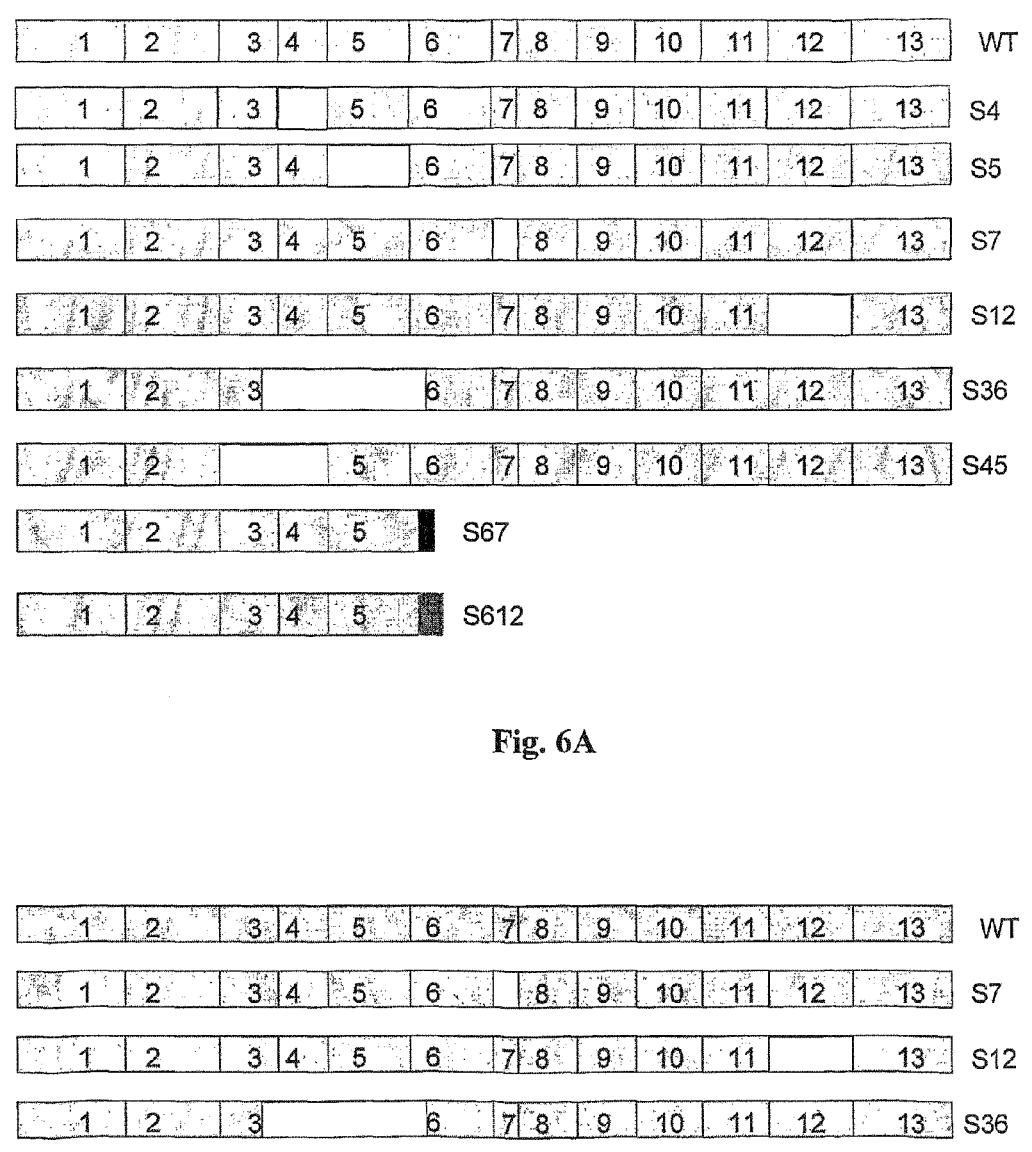
Figure 6C:
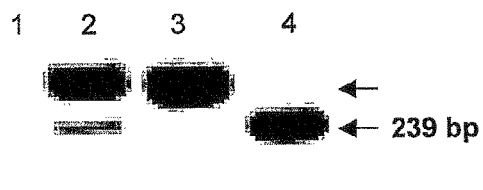
Figure 6D:
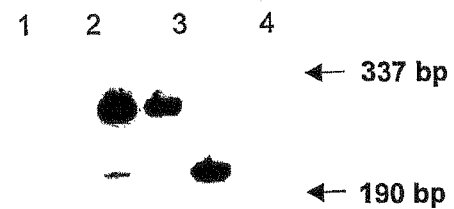
Figure 6E:
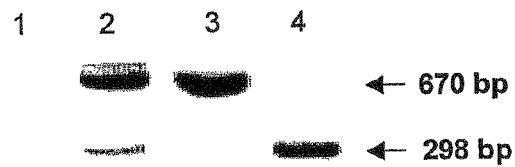

Human splice variant 5 was cloned by PCR reaction utilizing M45f-M2b (see FIG. 6H). Human Primers:
hMf: SEQ ID NO: 60, hMb: SEQ ID NO: 61, h3'b: SEQ ID NO: 62, hM45f: SEQ ID NO: 63, hM4f: SEQ ID NO: 64, hM9b: SEQ ID NO: 65, hM2b: SEQ ID NO: 66, and h1529f: SEQ ID NO: 67.

Example 1

Cloning of the *Spalax* Heparanase cDNA

The full length *Spalax* heparanase cDNAs (including 351 nucleotides in the 5'UTR and 74 nucleotides in the 3'UTR) from the four Israeli species were obtained and sequenced (FIG. 1, SEQ ID NO:69). The sequences presented in FIG. 1 (nucleic acid sequence SEQ ID NO: 69 and amino acid sequence SEQ ID NO:1) are that of *S. carmeli* (2n=58). The amino acid sequences of the other species vary in a few amino acids (*S. judaei*, $Arg^{285}$ is substituted to Lys, $Cys^{483}$ to Val, $Gly^{548}$ to Arg; *S. galili* $Glu^{190}$ to Asp, $Gly^{548}$ to Arg; *S. golani*, $Ala^{404}$ to Ser, $Gly^{548}$ to Arg) and are otherwise identical.

The cloned *Spalax* heparanase (FIG. 1) contains two initiation codons (ATG1 and ATG2) of which ATG2 corresponds to that of heparanase cloned from other species. The open reading frame starting from ATG2 consists of 1602 bp that encode for a polypeptide of 534 amino acids (compared to 543 amino acids of the human protein). Alignment of the amino acid sequences shows that the signal peptide in the N-terminus contains 26 amino acids, compared to 35 residues in the human enzyme (FIG. 2). A hydrophobic, possibly transmembrane region was identified at the C terminus ($Pro^{546}$-$Val^{564}$) (FIG. 1). Similar to other glycosyl hydrolases and to the human enzyme (7, 9), *Spalax* heparanase has a catalytic mechanism that involves two conserved acidic residues, a putative proton donor ($Glu^{256}$) and a nucleophile ($Glu^{374}$) (FIG. 1).

Human heparanase is synthesized as a latent 65 kDa precursor whose activation involves proteolytic cleavage at two potential sites located at the N-terminal region of the molecule ($Glu^{109}$-$Ser^{110}$ and $Gln^{157}$-$lys^{158}$), resulting in the formation of two subunits that heterodimerize to form the active heparanase enzyme (13-15). Homologous cleavage sites were identified in the *Spalax* heparanase at $Glu^{140}$-$Pro^{141}$ and $Gln^{188}$-$lys^{189}$. Alignment of the *Spalax* amino acid sequence with that of the rat, mouse, human, bovine, and chicken showed 86.7%, 88.6%, 85%, 83.7% and 67.2% identity, respectively. The predicted amino acid sequence of the *Spalax* heparanase has three potential N-glycosylation sites (FIG. 1), compared to six in the human (FIG. 2), and four in the mouse and rat heparanases (6-8, 36). All three N-glycosylation sites of the *Spalax* enzyme are conserved in the human, mouse and rat heparanases.

We have used the Kimura distances to generate a tree based on amino acid distances (FIG. 3). The similarity tree shows that *Spalax* is situated on a branch separate from the mouse and rat heparanases, and rodents are situated in a cluster separate from the other mammals (human and bovine) and markedly different from the chicken heparanase. The highest similarity in amino acids is between *Spalax* and mouse (88.6%). Alignment of human heparanase with *Spalax*, mouse or rat heparanases revealed that the *Spalax* enzyme possesses the highest similarity to human (85% vs. 81% and 80.5% similarity for the mouse and rat enzymes, respectively).

Example 2

Identification and Cloning of a Splice Variant of *Spalax* Heparanase Lacking Exon 7

A splice variant of *Spalax* heparanase was cloned from *Spalax* kidney. Sequence analysis revealed that it originates from splicing-out of exon 7 (37) (nucleotides 1287-1334), resulting in shortening of the wild type cDNA by 48 base pairs with no frame-shift (FIG. 1). Gel electrophoresis of PCR products amplified using primers designed around this deletion segment and kidney cDNA as a template, revealed both the wild type and spliced forms. Plasmids containing the coding region of either form were subjected to PCR and used as positive controls (FIG. 4A). The amino acid sequence of the splice variant lacks 16 amino acids in comparison to the wild type protein, the deletion located in a region between the nucleophile and proton donor residues ($Phe^{313}$-$His^{328}$) (FIGS. 1 & 2).

Figure 4C:
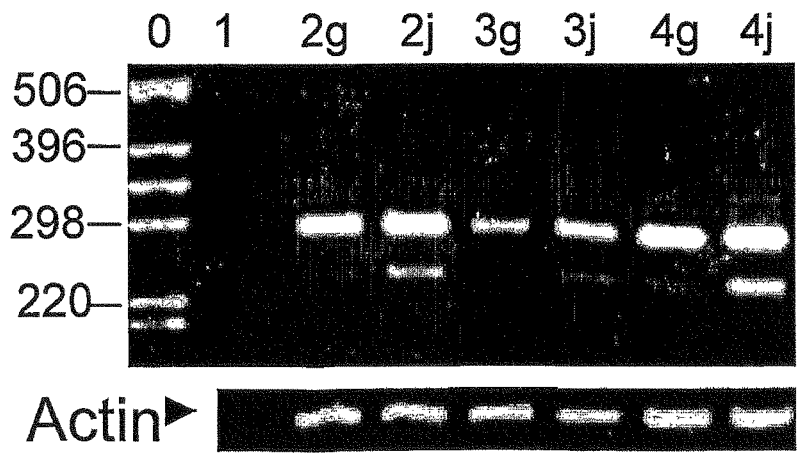

To evaluate the tissue distribution of heparanase and its splice variant in Spalax, cDNAs from different tissues were prepared and subjected to PCR using specific primers designed around exon 7. Both the splice variant and wild type heparanases were detected in cDNAs from kidney, liver, heart, brain and eye (FIG. 4B). The wild type cDNA constituted the principal form of heparanase, while splice variant SH7 ranged from 0 to 25% of the total heparanase, in different tissues and animals. A marked variation in tissue expression of Spalax heparanase splice variant SH7 was noted between individual animals from different ecogeographical locations. Splice variant SH7 was markedly higher in S. judaei which lives in a dry, normoxic environment than in S. galili which resides in humid-cool and frequently hypoxic conditions during the winter (FIG. 4C).

Example 3

Functional Expression of Wild Type and Splice Variant SH7 Spalax Heparanases in Mammalian Cells The full length human and Spalax heparanase cDNAs, as well as Spalax splice variant SH7 cDNA, were subcloned into the expression vector pcDNA3 and transfected into HEK293 cells. Stable transfected cells were obtained following selection with G418. Western blot analysis of wild type Spalax heparanase partially purified from cell lysates (utilizing anti heparanase antibody #1453 which recognizes both the unprocessed and processed enzyme) revealed 60- and 45-kDa protein bands (FIG. 5A, lane 3) compared with the 65- and 50-kDa latent and active forms of the human enzyme (FIG. 5A, lane 2). In order to evaluate the contribution of glycosylation to the molecular weight difference between the human and Spalax heparanases, cells stably transfected with each heparanase species were incubated (48 h, 37° C.) without or with 10 µg/ml tunicamycin (N-glycosylation inhibitor). Western blotting of cell lysates, utilizing anti-heparanase antibody #810 which recognizes the unprocessed protein, revealed a single band in both species, corresponding to the unprocessed heparanase. In cells that were not treated with tunicamycin, the human heparanase appeared as a 65 kDa band (FIG. 5B, lane 2) while that of Spalax corresponded to a 60 kDa protein (FIG. 5B, lane 3). Following treatment with tunicamycin, both the human and Spalax heparanases appeared as 53 kDa proteins (FIG. 5B, lanes 4 and 5), most likely due to their complete deglycosylation.

Next, we compared the expression pattern of splice variant SH7 and wild type Spalax heparanases, applying HEK293 cells transfected with each form. As shown in FIG. 5C (lane 1-mock, lane 2-wild type, lane 3-splice variant SH7), splice variant SH7 appeared as a 59 kDa band, as compared to the 60- and 45 kDa proteins of the wild type latent and active Spalax enzymes, respectively (FIG. 5C, upper panel). In order to evaluate secretion of the Spalax heparanase and its splice variant SH7, we cultured (24 h, 37° C.) HEK293 cells stably transfected with Spalax heparanase, splice variant SH7, or insert free mock plasmid in the absence or presence of 20 µg/ml heparin. We have previously demonstrated accumulation of secreted heparanase in the presence of heparin (38). Western blot analysis of the incubation medium using anti-heparanase antibodies revealed secretion and accumulation of the wild type latent enzyme in the culture medium (FIG. 5C, second panel). In contrast, splice variant SH7 was not detected in the incubation medium (FIG. 5C, second panel) regardless of the presence of heparin, indicating its inability to be secreted and to accumulate in the culture medium (38). In order to assess the binding of Spalax heparanase and Splice variant SH7 to heparin, lysates of cells transfected with each variant or with a mock control plasmid, were incubated with heparin-Sepharose beads or with Fractogel (cation exchange resin) as a positive control. The beads were washed with PBS and the bound proteins were subjected to immunoblotting. Both the wild type and splice variant SH7 Spalax heparanases bind to heparin beads and were readily detected following SDS/PAGE of the bound proteins and Western blotting (FIG. 5C, fourth panel).

Example 4

Heparanase Enzymatic Activity

We assessed the ability of Spalax heparanase and its splice variant SH7 to degrade HS in intact ECM. For this purpose, lysates of HEK293 cells stably transfected with the full length Spalax heparanase, splice variant SH7, or a mock control were incubated (4 h, 37° C., pH 6.0) with intact naturally produced sulfate-labeled ECM. Labeled degradation fragments released into the incubation medium were then analyzed by gel filtration on Sepharose 6B. Sulfate labeled material released by the mock transfected cells eluted just after the void volume ($V_o$) (peak I, fractions 1-10, $K_{av}$<0.2) and consisted almost entirely of intact, high-molecular weight HSPGs released from the ECM by proteolytic enzymes present in the cell lysate and/or residing in the ECM itself (39). Similar results were obtained with Splice variant SH7 transfected cells. In contrast, incubation of the ECM with lysates of cells transfected with the wild type Spalax heparanase resulted in release of low-molecular weight labeled degradation fragments eluted toward the $V_t$ of the column (peak II, fractions 20-30, $0.5<K_{av}<0.8$) (FIG. 5D). These fragments were shown to be degradation products of HS as they were i) 5-6 fold smaller than intact HS side chains; ii) resistant to further digestion with papain and chondroitinase ABC, and iii) susceptible to deamination by nitrous acid (39).

Example 5

Cloning of Additional Splice Variants of Spalax Heparanase (SH)

Additional splice variants of Spalax heparanase (SH), SH12, SH36, SH67 and SH612 were cloned in a similar way as splice variant SH7. FIG. 6A shows the schematic structure of the cloned Spalax heparanase splice variants: SH7, SH12, SH36, SH67 and SH612 as well as Spalax heparanase splice variants SH5, SH4 and SH45 predicted according to a mathematical model. FIG. 6 illustrates the structures of the different splice variants. The DNA sequence of SH4, SH5, SH7, SH12, SH36, SH45, SH67, SH612 (SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18 respectively) and the corresponding predicted amino acid sequences (SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17 respectively) are disclosed in the sequence listing below.

Splice variants SH5, SH7, SH12, SH36, SH67, and SH612 result from skipping of exons #5; #7; #12; part of #3, #4, #5 and part of #6; #6 and #7; and #6, #7, #8, #9, #10, #11, and #12, respectively (see Table 1 and FIG. 6G). Splice variants SH5, SH7, SH12, SH36 result from deletion of a number of nucleic acids that is a multiple of three, hence no frame shift occurs and the predicted amino acid sequence of these variants is shorter by 174, 48, 147, and 372 base pairs respectively which encodes for 58, 16, 49, and 124 amino acids respectively. Splice variant SH67 and SH612 results in truncated heparanase which possess a unique tail of 3 and 9 amino acids respectively (FIG. 6). *Structure of Splice variant SH36.* Splice variant SH36 spans 372 nucleic acids extending upon four exons (3 through 6). This splice variant involves partial skipping of exons 3 and 6, which shares the nucleic acid sequence: AAGAAGG. Actually, the deletion in splice variant SH36 starts immediately after this sequence occurs in exon #3 and finishes exactly after this same sequence finishes in exon #6, indicating it as a possible signal to the splicing machinery.

Gel electrophoresis of polymerase chain reaction (PCR) products amplified using primers designed around the deletion segment of splice variant SH7, SH12, and SH36 and *Spalax* kidney cDNA as a template, revealed both the wild type and spliced forms (FIGS. 6 *c, d,* and *e,* respectively). Plasmids containing the coding region of either form were subjected to PCR and used as positive controls.

The deleted nucleic acids in splice variant SH36 encodes the last amino acid of the 8 kDa subunit, the linker sequence (combing the 8 and 45 kDa subunits) and the N-terminus of the 45 kDa subunit including the putative proton donor. Splice variant SH36 lacks two out of the three potential N-glycosylation sites described in the wild type enzyme.

Figure 6F:
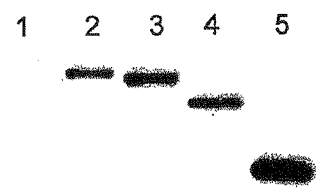

FIG. 6F shows the molecular weight of the recombinant SH WT, and splice variants SH7, SH12 and SH36 expressed in HEK293 cells.

Recombinant wild type heparanase is secreated to the medium of cultured cells, and accumulates upon addition of heparin. We observed that recombinant splice variant SH36, similar to SH7, is not detected in the medium regardless to presence of heparin. Table 1 shows the initiation and end of each of the *Spalax* heparanase exons.

TABLE 1

| Exon # | Start | End |
|---|---|---|
| 3 | 674 | 819 |
| 4 | 820 | 945 |
| 5 | 946 | 1119 |
| 6 | 1120 | 1288 |
| 7 | 1289 | 1336 |
| 8 | 1337 | 1430 |
| 9 | 1431 | 1537 |
| 10 | 1538 | 1537 |
| 11 | 1653 | 1771 |
| 12 | 1772 | 1918 |

Example 6

Evaluation of Heparanase Enzymatic Activity of Splice Variants and WT SH

We assessed the ability of *Spalax* heparanase and its splice variant to degrade heparan sulfate (HS) in intact ECM. For this purpose, full length *Spalax* heparanase cDNA or splice variant SH7 cDNA, were subcloned into the expression vector pcDNA3 and stably transfected into HEK293 cells (FIG. 5). Lysates of HEK293 cells transfected with the full length *Spalax* heparanase, splice variants, or a mock control were incubated (4 h, 37° C., pH 6.0) with intact naturally produced sulfate-labeled ECM and the pattern of the labeled degradation products of HS released into the incubation medium was analyzed by gel filtration on Sepharose 6B. Sulfate labeled material released by the mock and splice variant SH7 cells eluted just after the void volume ($V_0$) (peak I, fractions 1-10, $K_{av}$<0.2) and consisted almost entirely of intact, high-molecular weight HSPGs released from the ECM by proteolytic enzymes present in the cell lysate and/or residing in the ECM itself. Similar results were obtained with Splice SH36 transfected cells. In contrast, incubation of the ECM with lysates of cells transfected with the wild type *Spalax* heparanase resulted in release of low-molecular weight labeled degradation fragments eluted toward the $V_t$ of the column (peak II, fractions 20-30, 0.5<$K_{av}$<0.8). These fragments were shown to be degradation products of HS as they were i) 5-6 fold smaller than intact HS side chains; ii) resistant to further digestion with papain and chondroitinase ABC, and iii) susceptible to deamination by nitrous acid.

Figure 7:
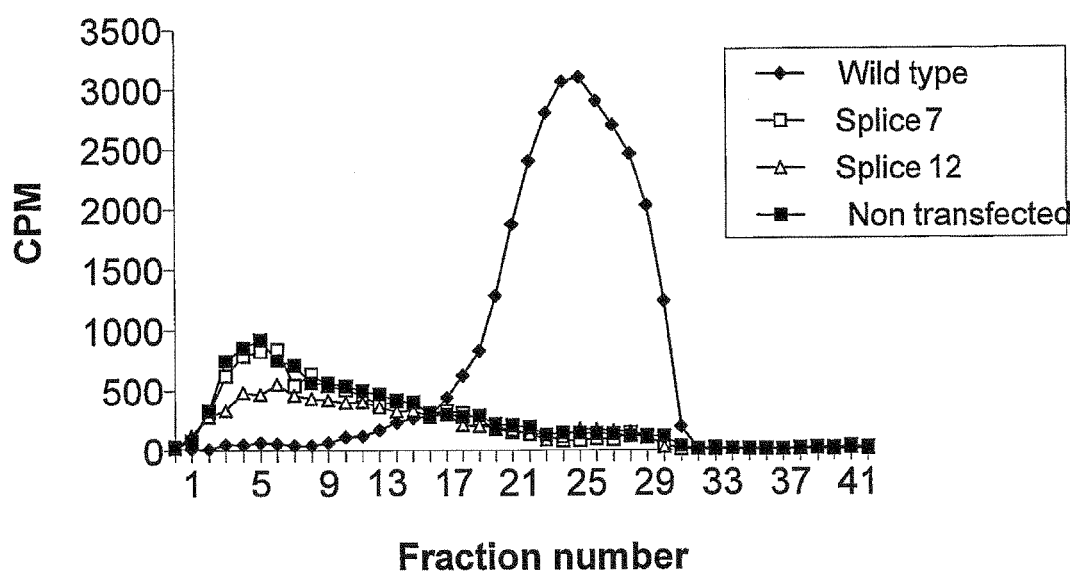
FIG. 7 is a graph showing that S7 and S12 variants themselves lack heparanase enzymatic activity. Lysates of cell stably transfected with pcDNA3 vectors containing *Spalax* wild-type (♦), splice variant 7 (□) or splice variant 12 (Δ) heparanases vs. mock, non transfected (■), were incubated (4 h, 37° C., pH 6.0) with $^{35}$S-labeled ECM. Labeled degradation fragments released into the incubation medium were analyzed by gel filtration on Sepharose 6B. Peak I (fractions 1-10), representing nearly intact HSPGs, was noticed in the mock (■) and splice variant 7 (□) and 12 (Δ) transfected cells. Peak II (fractions 20-30), representing HS degradation products, was obtained in cells transfected with the wild type *Spalax* heparanase (♦).

In a similar experiment summarized in FIG. 7 we found that splice variant SH12 lack the ability to degrade heparan sulfate as well.

Thus, the results obtained show that SH 7, 12 and 36 lack heparanase enzymatic activity.

Figure 8A:
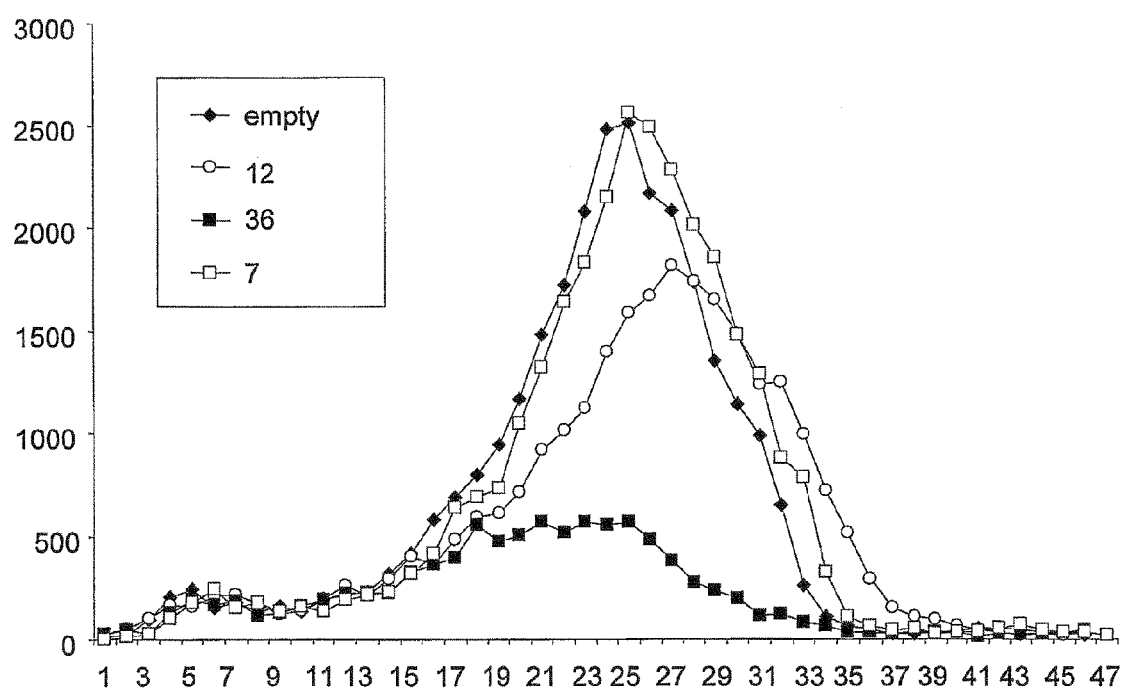
FIGS. 8A-8C depict graphs showing dominant negative effect of *Spalax* heparanase splice variants on endogenous heparanase activity of melanoma B16 cells. B16 cells were transfected with empty vector (control) and vector containing SH7, SH12 or SH36. The ability of the transfected cells to degrade HS was monitored after a 2-hour (A), 3-hour (B) and overnight (C) incubation of the cells with labeled HS, and enzymatic activity of heparanase was measured as described in FIG. 5D.
Figure 8B:
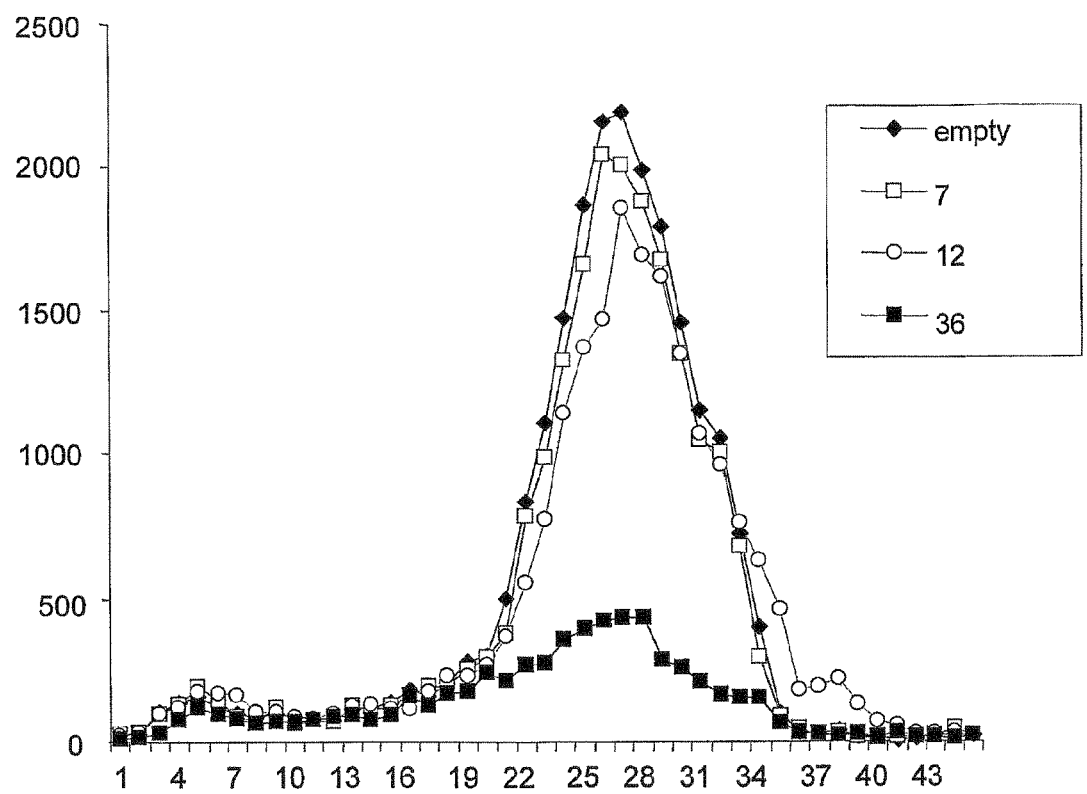
Figure 8C:
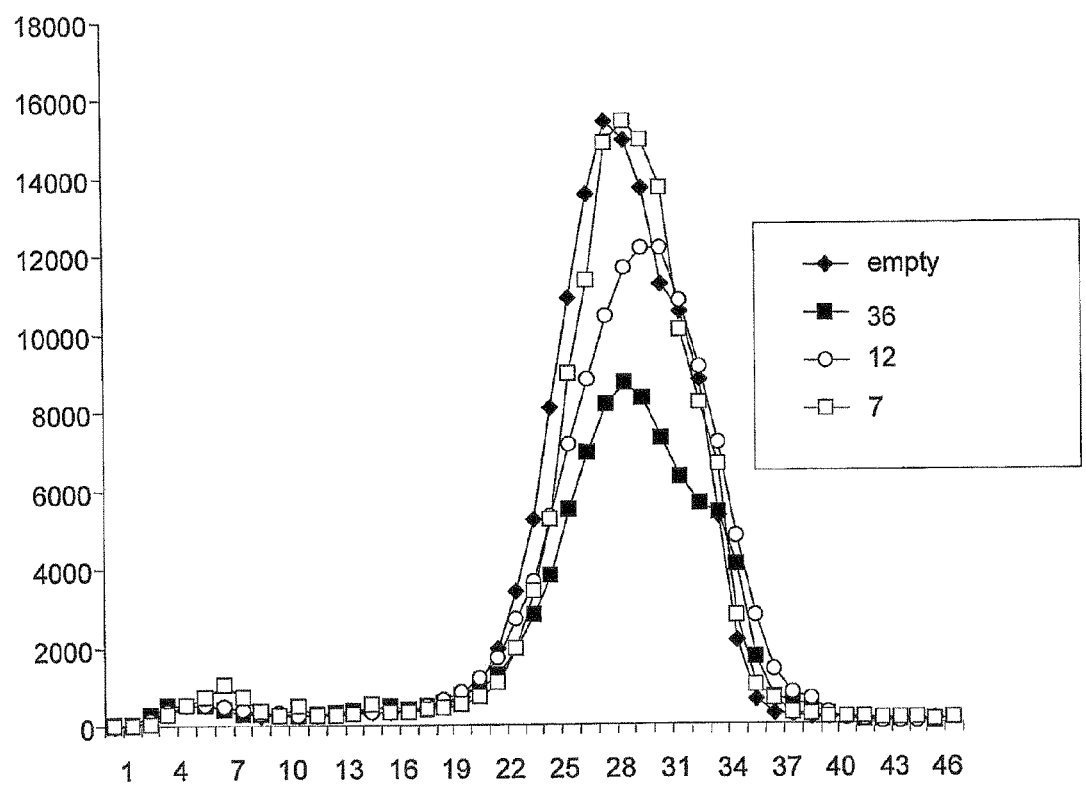

In order to evaluate the effect of splice variants on the ability of endogenous heparanase to degrade HS, we transfected B16 melanoma cells with plasmid containing splice SH12, SH36 or empty vector as a control. Cells transfected with the control vector degraded labeled HS chains of ECM significantly more than those transfected with splice variant SH36 or SH12 (FIG. 8). This result shows that heparanase splice variant SH36 and SH12 behave as dominant negatives to the endogenous heparanase of B16 melanoma cells. In a similar experiment carried out with SH7, we found in some experiments that SH7 can inhibit the enzymatic activity of heparanase (not shown).

Figure 9:
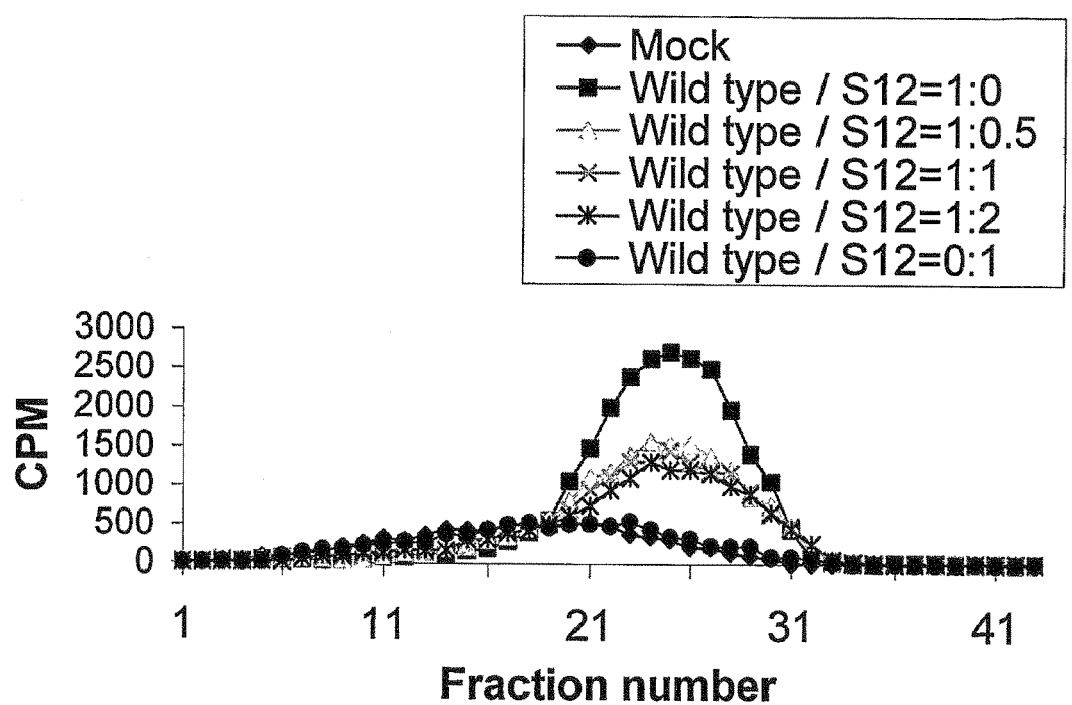
FIG. 9 is a graph showing that SH12 decreased the activity of the wild-type SH enzyme. HEK293 cells were cotransfected with a plasmid carrying the wild-type *Spalax* heparanase (1=2.5 μg) and indicated amounts of a plasmid carrying the splice variant SH12. Enzymatic activity of heparanase was measured as described in FIG. 5D.

Next, we assessed the effect of *Spalax* heparanase splice variants on the activity of the WT *Spalax* heparanase. For this purpose, HEK293 cells were co-transfected with a plasmid carrying the WT *Spalax* heparanase a plasmid carrying the splice variant of *Spalax* heparanase SH12, and enzymatic activity of heparanase was measured as described above (FIG. 9).

Briefly, after transfection, cell lysates of transfected cell were incubated with naturally produced sulfate-labeled ECM (as described above) and the pattern of heparan sulfate degradation was monitored (as described above). The control included cells co-transfected with a WT heparanase containing plasmid and with an empty plasmid. We found that SH12 inhibited the activity of wild type *Spalax* heparanase. In a similar experiment carried out with SH36, we found with SH36 the same result.

Therefore, the results obtained indicated that splice variants SH12 and SH36 have a dominant negative effect on the enzymatic activity of heparanase.

Example 7

Effect of Heparanase Splice Variants in Tumour Growth in a Nude Mice Model

Figure 10:
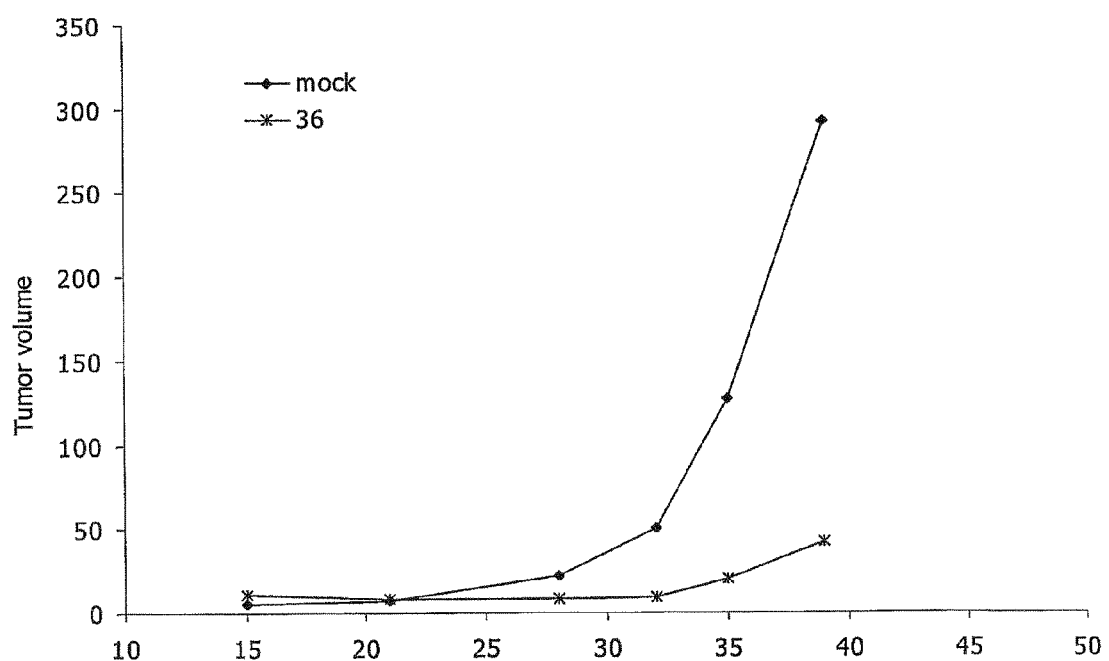
FIG. 10 is a graph showing that tumor development in nude mice injected with glioma cells transfected with SH36 is reduced compared to tumor development in mice injected with glioma mock cells. U87 glioma cells were transfected with mock or with SH36 cDNA containing plasmid. U87 mock glioma cells or U87 glioma transfected with SH36 were subcutaneously injected into nude mice and tumor growth at the site of injection was measured as function of time.
Figure 11:
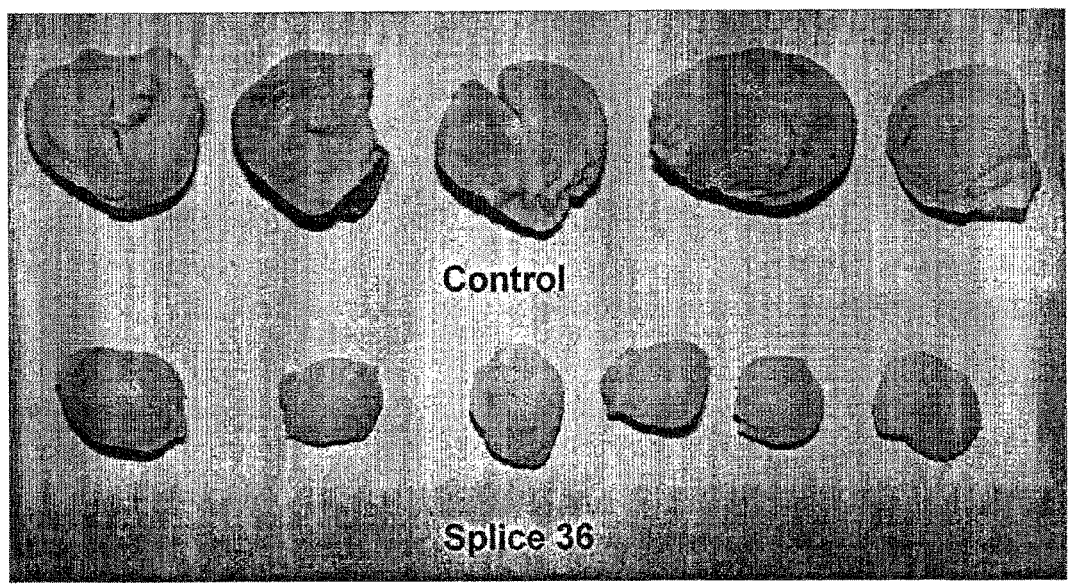
FIG. 11 shows that tumor development in nude mice injected with glioma cells transfected with SH36 is reduced compared to tumor development in mice injected with glioma mock cells. U87 glioma cells transfected with mock (control) or SH36 plasmid were injected subcutaneous to the nude mice and the tumor was excised after 40 days.

In view of our above results showing the capability of splice variants to regulate the heparanase enzymatic activity, and due to the role of heparanase in angiogenesis and cancer development, we explored the effect of splice variants and WT *Spalax* heparanase in tumor development in vivo. For this purpose, U87 glioma cells were transfected with mock or with a SH36 cDNA containing plasmid. U87 mock glioma cells or U87 glioma transfected with SH36 were subcutaneously injected into nude mice and tumor growth at the site of injection was measured as a function of the time (FIGS. 10 and 11). Tumor size was measured twice a weak, and after 40 days mice were sacrificed, tumors dissected, and its weigh measured. We found that mice injected with cells harboring splice variant SH36 developed significantly smaller tumor relative to control mice. The development of the tumor in the group of mice injected with cells transfected with SH36 was slower throughout the whole experiment.

Similar experiments, carried out with different types of tumor cells transfected with SH36 confirmed that SH36 decreases tumor development in vivo (not shown). This was evident by smaller tumor size and weight in tumor derived from cell lines transfected with splice variant SH36 relative to controls.

In all, the results obtained with splice variant SH36 show that SH36 is capable of downregulating heparanase activity and of downregulating tumor growth.

Figure 12:
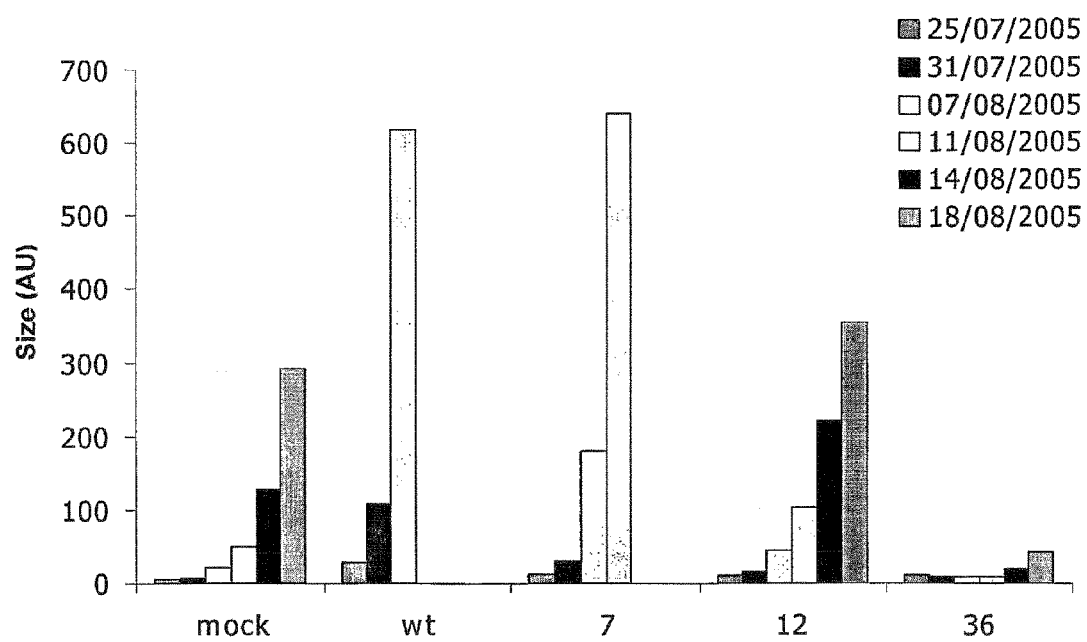
FIG. 12 shows tumor development in nude mice injected with glioma cells transfected with wild-type SH, splice variants SH7, SH12, SH36 or mock control. U87 glioma cells were transfected with mock or with wild-type SH or splice variants SH7, SH12, SH36 cDNA containing plasmid. The U87 mock glioma cells or U87 glioma transfected with wild-type SH, splice variants SH7, SH12, or SH36 cDNA containing plasmid were subcutaneously injected into nude mice and tumor growth at the site of injection was measured at the indicated times (min. and max. values were excluded). Tumor volume (V) was determined by the equation: $V=L\times W^2\times 0.5$, where L is the length and W is the width of the xenograft. AU=Area Units.
Figure 13:
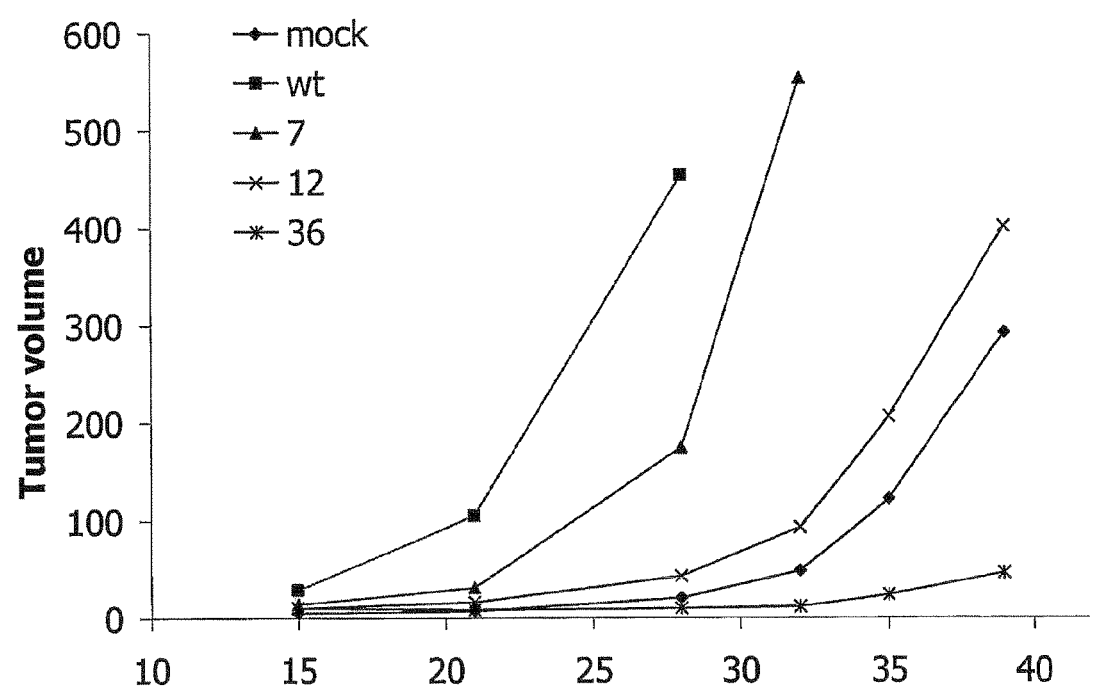
FIG. 13 shows tumor development in nude mice injected with glioma cells transfected with wild-type SH, splice variants SH7, SH12, SH36 or mock control. U87 glioma cells were transfected with mock or with wild-type SH or splice variants SH7, SH12, SH36 cDNA containing plasmid. The U87 mock glioma cells or U87 glioma transfected with WT SH, splice variants SH7, SH12, or SH36 cDNA containing plasmid were subcutaneously injected into nude mice and tumor growth at the site of injection was measured as a function of time.

Similar in vivo experiments were carried out with U87 cells transfected with WT heparanase, mock, SH36, SH7 or SH12 containing plasmid (FIGS. 12-13). We observed that the WT *Spalax* heparanase is a potent inducer of tumor development (compare results with mock). In this experiment, the inhibitory effect of SH36 in tumor development was confirmed. We observed that in spite that SH12 was previously found to inhibit heparanase enzymatic activity it did not inhibit growth in the U87 model (compare with mock). SH7 previously found to lack any heparanase enzymatic activity, was found to increase tumor growth as well (compared with mock).

Since tumors removed from SH7 mice appear to have augmented vasculature compared to tumors removed from mock control mice (not shown) it appears that SH7 has proangiogenic activity regardless to the fact that it does not posses heparanase enzymatic activity.

Example 8

Splice Variants of Human Heparanase (HH)

As shown above, we were successful in isolating for the first time splice variants of heparanase. In view of our results, we anticipated that heparanase splice variants homologous to the SH splice variants are present in humans as well.

We cloned a novel splice variant of heparanase from cDNA of kidney from a patient suffering from renal cell carcinoma. This splice variant originates from splicing out of exon 5, which result in a deletion of 174 bp compared to the wild type cDNA. The reading frame of the splice variant is conserved compared to that of the wild type gene, and its predicted amino acid sequence (HH5, SEQ ID NO: 21) is shorter by 54 residues (485aa for splice 5 compared to 543 aa of the wild type).

Figure 14A:
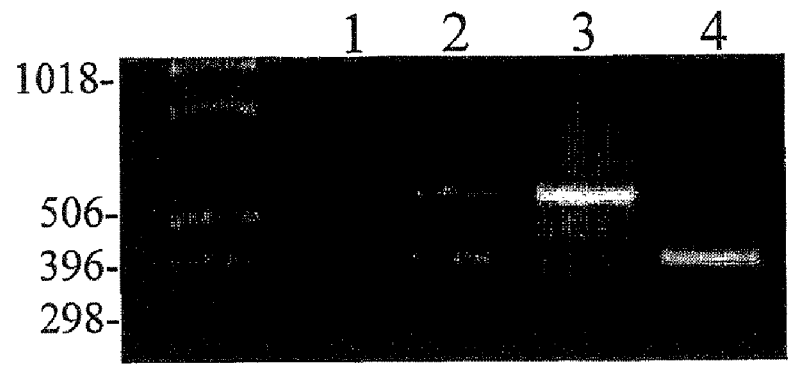
FIGS. 14A-14B show (A) semi-quantitative RT-PCR using human specific primers located around the heparanase cDNA region encoded by exon 5. Bands of 579 bp represent the wild-type enzyme, while those of 405 bp represent its splice 5 form. Lane 1, reaction mixture alone; lane 2, cDNA of human kidney; lanes 3 and 4, plasmids containing the cDNA sequence of the wild-type human heparanase and the splice 5 variant, respectively. Left to the DNA ladder are the corresponding numbers of base pairs. (B) Western blot analysis utilizing the anti-heparanase antibody 1453 on lysates and incubation mediums of U87 cell transfected with either a mock empty vector (M), or a vector containing human wild-type (WT) or splice 5(S5) heparanases.

Gel electrophoresis of PCR products amplified using primers designed around this deletion segment and kidney cDNA as a template, revealed both the wild type and spliced forms. Plasmids containing the coding region of either form were subjected to PCR and used as positive controls (FIG. 14A).

Figure 14B:
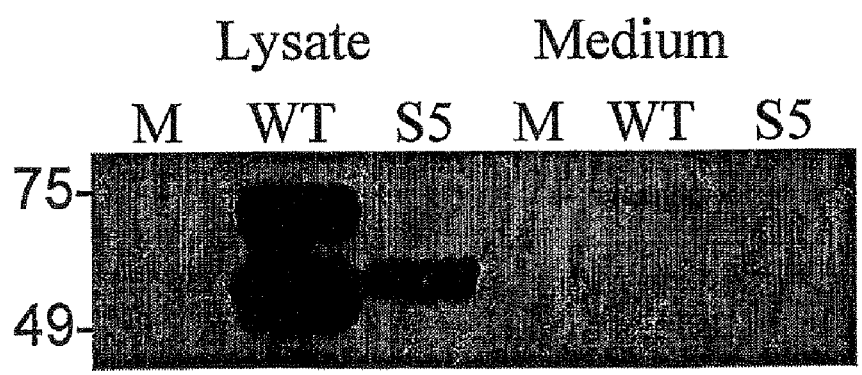
Figure 15A:
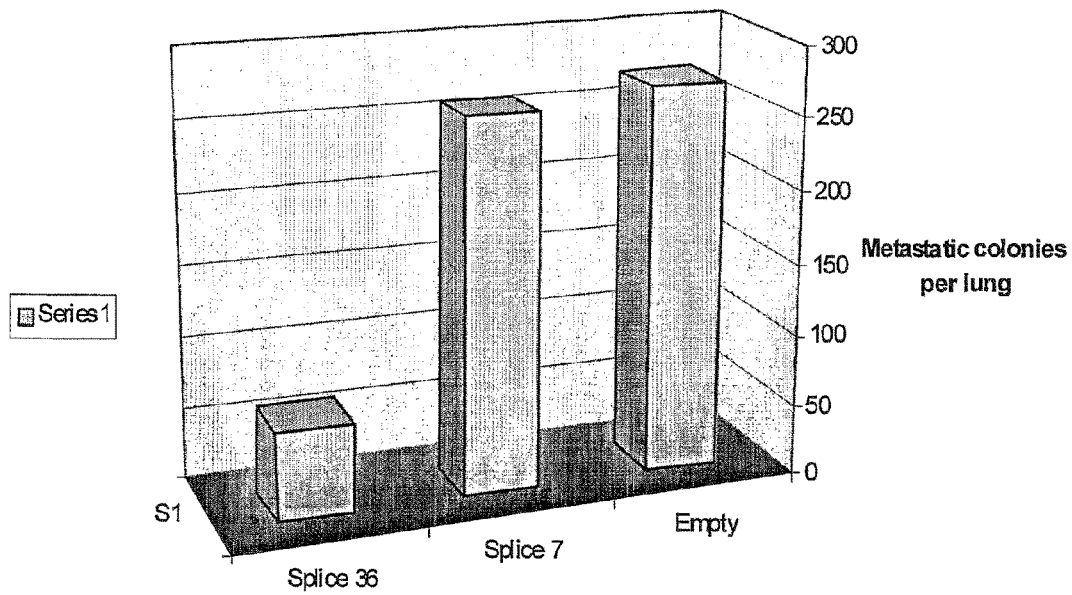
FIGS. 15A-15C show the effect of splice variant expression on metastasis formation. C57BL/6 mice were injected with 0.4 mL of a cell suspension containing $0.4\times 10^6$ B16-BL6 melanoma cells transiently transfected with pcDNA vector containing heparanase splice variant SH7, SH36 or empty construct. Fifteen days after cell injection, mice were killed, their lungs were removed, fixed in Bouin's solution, and scored under a dissecting microscope for the number of metastatic nodules on the lung surface. Five mice were used per group. (A) Average number of metastasis in each group. (B) Number of lung metastasis in each of the 15 mice of the three groups (S7, S36, empty construct). (C) Average number of metastasis in each group ±SD. (15D) Photograph of the lung. Black lesions denotes metastasis.
Figure 15B:
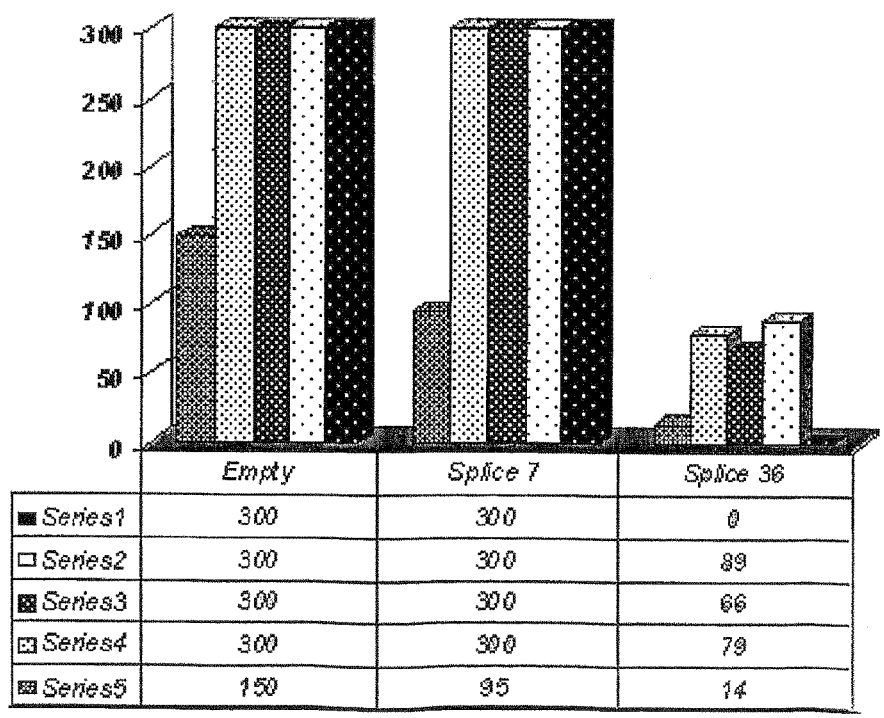
Figure 15C:
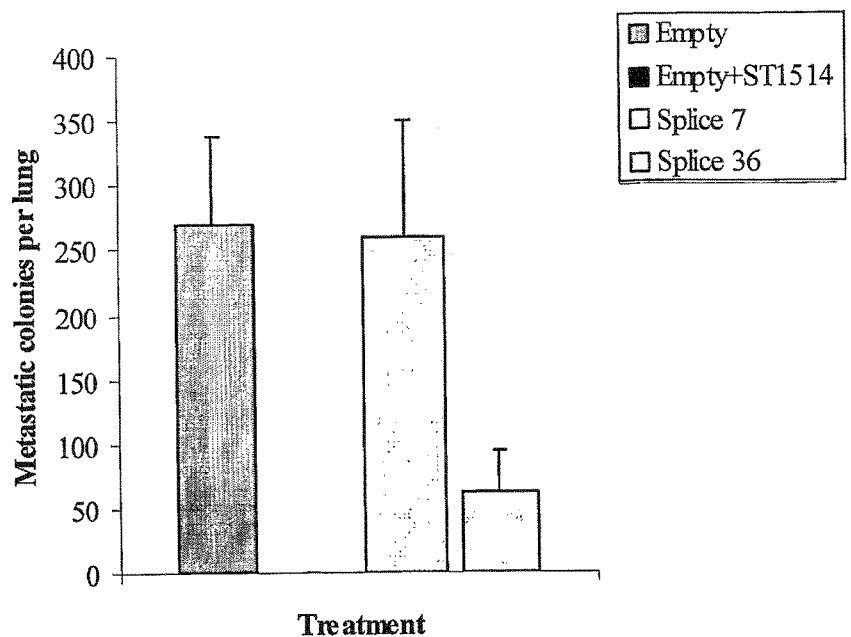
Figure 15D:
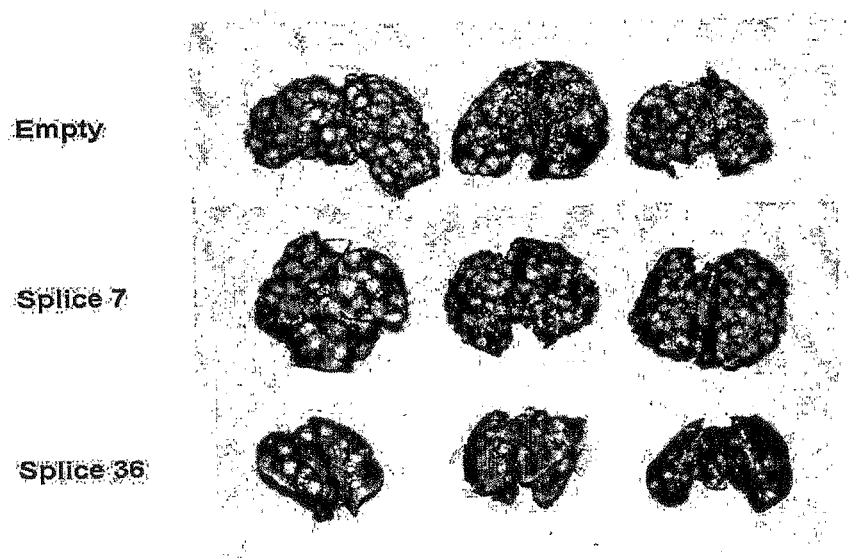

Next, we compared the expression pattern of splice 5 and wild type human heparanases, applying MCF-7 cells transiently transfected with each form. Western blot (using anti-heparanase antibody 1453) of cell lysates revealed a single band of about 55 kDa in splice 5 transfected cells compared to 65 and 50 kDa protein bands in the wild type heparanase transfected cells lysate. Splice 5 do not appears in the incubation medium, as opposed to the wild type latent protein which accumulates in the medium (FIG. 14B).

Our results enable identification of the human heparanase splice variants that are equivalent to the *Spalax* splice variants (e.g. by PCR using primers around the spliced out exons as in FIG. 6H), elucidation of their function (e.g. as exemplified above with the SH splice variants) and physiological significance. Homologous human heparanase (HH) splice variants HH4 (SEQ ID NO: 19), HH5 (SEQ ID NO: 21), HH7 (SEQ ID NO: 23), HH12 (SEQ ID NO: 25), HH36 (SEQ ID NO: 27), HH45 (SEQ ID NO: 29), HH 67 (SEQ ID NO: 31), and HH 612 (SEQ ID NO: 33) and the corresponding nucleic acid sequences encoding them (SEQ ID NO: 20, SEQ ID NO: 22, SEQ ID NO: 24, SEQ ID NO: 26, SEQ ID NO: 28, SEQ ID NO: 30, SEQ ID NO: 32, and SEQ ID NO: 34, respectively) can be found in the sequence listing.

Example 10

Inhibition of Metastasis Formation by *Spalax* Heparanase Splice Variant SH36

In order to assess the effect of splice variant expression on metastasis formation, C57BL/6 mice were injected with 0.4 mL of a cell suspension containing $0.4 \times 10^6$ B16-BL6 melanoma cells transiently transfected with pcDNA vector containing heparanase splice variant SH7, SH36 or empty construct. Fifteen days after cell injection, mice were killed, their lungs were removed, fixed in Bouin's solution, and scored under a dissecting microscope for the number of metastatic nodules on the lung surface. Five mice were used per group. We found that B16-BL6 melanoma cells transiently transfected with heparanase splice variant SH36 established statistically significantly fewer metastatic colonies than cells transfected with empty vector or with vector harboring splice 7. Fig A. shows the average number of metastasis, Fig B the number of lung metastasis in each mice of the experiment and C the number of metastasis, mean and SD. D. The photograph of the lungs shows inhibition of metastasis by splice SH36.

REFERENCES

1. Kjellen, L. and Lindahl, U. (1991) Annu Rev Biochem 60, 443-475.
2. Bernfield, M., Gotte, M., Park, P. W., Reizes, O., Fitzgerald, M. L., Lincecum, J. and Zako, M. (1999) Annu Rev Biochem 68, 729-777.
3. Iozzo, R. V. (1998) Annu Rev Biochem 67, 609-652.
4. Vlodavsky, I., Bar-Shavit, R., Korner, G. and Fuks, Z. (1993) in Basement membranes: Cellular and molecular aspects, eds. Rohrbach, D. H. and Timpl, R. (Academic press Inc., Orlando, Fla.), pp. 327-343.
5. Vlodavsky, I., Miao, H. Q., Medalion, B., Danagher, P. and Ron D. (1996) Cancer Metastasis Rev 15, 177-186.
6. Vlodavsky, I., Friedmann, Y., Elkin, M., Aingorn, H., Atzmon, R., Ishai-Michaeli, R., Bitan, M., Pappo, O., Peretz, T., Michal, I., Spector, L. and Pecker I. (1999) Nat Med 5, 793-802.
7. Hulett, M. D., Freeman, C., Hamdorf, B. J., Baker, R. T., Harris, M. J., and Parish, C. R. (1999) Nat. Med. 5, 803-809.
8. Vlodavsky, I. and Friedmann, Y. (2001) J. Clin. Invest. 108, 341-347.

9. Parish, C. R., Freeman, C., and Hulett, M. D. (2001) Biochim. Biophys. Acta 1471, M99-108
10. Edovitsky, E., Elkin, M., Zcharia, E., Peretz, T., Vlodavsky I. (2004) J Natl Cancer Inst. 96, 1219-1230.
11. Kussie, P. H., Hulmes, J. D., Ludwig, D. L., Patel, S., Navarro, E. C., Seddon, A. P., Giorgio, N. A. and Bohlen P. (1999) Biochem Biophys Res Commun 261, 183-187.
12. Toyoshima, M. and Nakajima, M. (1999) J Biol Chem 274, 24153-24160.
13. Abboud-Jarrous, G., Aingorn, H., Rangini-Guetta, Z., Atzmon, R., Elgavish, S., Peretz, T. and Vlodavsky, I. (2005) J. Biol. Chem. 280, 13568-13575.
14. Levy-Adam, F., Miao, H. Q., Heinrikson, R. L., Vlodavsky, I. and Ilan N. (2003) Biochem. Biophy. Res. Commun. 308, 885-891.
15. McKenzie, E., Young, K., Hircock, M., Bennett, J., Bhaman, M., Felix, R., Turner, P., Stamps, A., McMillan, D., Saville, G., Ng, S., Mason, S., Snell, D., Schofield, D., Gong, H., Townsend, R., Gallagher, J., Page, M., Parekh, R. and Stubberfield, C. (2003) Biochem. J. 373, 423-435.
16. Nevo, E. (1999) Mosaic evolution of subterranean mammals: regression, progression, and global convergence (Oxford university press, Oxford).
17. Nevo, E., Ivanitskaya, E. and Beiles, A. (2001) Adaptive radiation of blind subterranean mole rats (Backhuys, Leiden, The Netherlands)
18. Nevo, E., (1991). Evol. Biol 25, 1-125.
19. Widmer, H. P., Hoppeler, H., Nevo, E., Taylor, C. R. and Weibel, E. W. (1997) Proc. Natl. Acad. Sci. USA 94, 2062-2067.
20. Shams, I., Avivi, A. and Nevo, E. (2004). Proc Natl Acad Sci U.S.A., 26, 9698-703.
21. Edoute, Y., Arieli, R. and Nevo, E., (1988) J. Comp. Physiol. 158, 575-582.
22. Weibel, E. R., Federspiel, W. J., Fryder-Doffey, F., Hsia, C. W., konig, M., Stalder-Navarro, V. and Vock R. (1993) Respir. Physiol. 93, 125-149.
23. Arieli, R. (1990) in Evolution of subterranean mammals at organismal and molecular levels, eds Nevo, E. and Reig, O. (Wiley-Liss, New York) pp. 251-268.
24. Avivi, A., Resnick, M. B., Nevo, E., Joel, A. and Levy A. P. (1999) FEBS Letters 452, 133-140.
25. Avivi, A., Shams, I., Joel, A., Lache, O., Levy, A. P. and Nevo E. (2005) FASEB J. 19:1314-1316.
26. Ashur-Fabian, O., Avivi, A., Trakhtenbrot, L., Adamsky, K., Cohen, M., Kajakaro, G., Joel, A., Amariglio, N., Nevo, E. and Rechavi, G. (2004) Proc. Natl. Acad. Sci. USA. 101, 12236-12241.
27. Avivi, A., Ashur-Fabian, O., Amariglio, N., Nevo, E. And Rechavi G. (2005) Cell Cycle 4, 368-372.
28. Koshikiawa, N., Iyozumi, A., Gassmann, M. and Takenaga K. (2003) Oncogene 22, 6717-6724.
29. Kimura, M. (1983). The Neutral Theory of Molecular Evolution (Cambridge University Press, Cambridge).
30. Goldshmidt, O., Zcharia, E., Abramovitch, R., Metzger, S., Aingorn, H., Friedmann, Y., Mitrani, E. and Vlodavsky I. (2002) Proc Natl Acad Sci USA 99, 10031-10036.
31. Goldshmidt, O., Zcharia, E., Aingorn, H., Guatta-Rangini, Z., Atzmon, R.,
32. Michal, I., Pecker, I., Mitrani, E. and Vlodavsky I. (2001) J Biol Chem 276, 29178-29187.
33. Miao, H. Q., Elkin, M., Aingorn, E., Ishai-Michaeli, R., Stien, C. A., Vlodavsky I. (1999) Int. J. Cancer 83, 424-431.
34. Friedmann, Y., Vlodavsky, I., Aingorn, H., Aviv, A., Peretz, T., Pecker, I. and Pappo O. (2000) Am. J. Pathol. 157, 1167-1175.
35. Zetser, A., Levy-Adam, F., Kaplan, V., Gingis-Velitski, S., Bashenko, Y., Schubert, S., Flugelman, M. Y., Vlodavsky I. and Ilan N. (2004) J. Cell Sci. 117, 2249-2258.
36. Zetser, A., Bashenko, Y., Miao, H. Q., Vlodavsky, I. and Ilan N. (2003) Cancer Res. 63, 7733-7341.
37. Miao, H. Q., Navarro, E., Patel, S., Sargent, D., Koo, H., Wan, H., Plata, A., Zhou, Q., Ludwig, D., Bohlen, P. and Kussie P. (2002) Protein Expr Purif. 26, 425-431.
38. Dong, J., Kukula, A. K., Toyoshima, M. and Nakajima M. (2000) Gene 253, 171-178.
39. Levy-Adam, F., Abboud-Jarrous, G., Guerrini, M., Beccati, D., Vlodavsky, I. and Ilan, N. (2005) J Biol Chem 280, 20457-20466.
40. Vlodavsky, I., Fuks, Z., Bar-Ner, M., Ariav, Y., and Schirrmacher, V. (1983) Cancer Res. 43, 2704-2711.
41. Avivi, A., Albrecht, U., Oster, H., Joel, A., Beiles, A. and Nevo E. (2001) Proc Natl Acad Sci U.S.A. 98:13751-13756.
42. Avivi, A., Oster, H., Joel, A., Beiles, A., Albrecht, U. and Nevo E. (2002) Proc Natl Acad Sci U.S.A. 98:11718-11723.
43. Sanyal, S., Jansen, H. G., de Grip, W. G., Nevo, E. and de Jong, W. W. (1990) Invest. Opthalmol. Visual Sci. 31, 1398-1404.
44. Simizu, S., Ishida, K., Wierzba, M. K. and Osada, H. (2004) J. Biol. Chem. 279, 2697-2703.
45. Ast, G. (2004) Nat Rev Genet 5, 773-782.
46. Boue, S., Letunic, I. and Bork P. (2003) Bioessays. 25, 1031-1034.
47. Dorsett, Y. and Tuschl, T. (2004) Nat Rev Drug Discov 3 (4), 318-29.
48. Kim, D. H., Behlke, M. A., Rose, S. D., Chang, M. S., Choi, S. and Rossi, J. J. (2005) Nat Biotechnol 23 (2), 222-6.
49. Nasser, N. J., Sarig, G., Brenner, B., Nevo, E., Goldshmidt, O., Zcharia, E., Li, J. P. and Vlodavsky, I. (2006) J. Thromb Haemost 4, 560-565.

The invention claimed is:

1. An isolated heparanase polypeptide splice variant, comprising the amino acid sequence of SEQ ID NO:11.

2. An isolated polynucleotide, comprising the nucleic acid sequence encoding the heparanase polypeptide splice variant of the amino acid sequence of SEQ ID NO:11.

3. An expression vector, comprising the polynucleotide according to claim 2.

4. A isolated host cell comprising the expression vector according to claim 3.

5. A pharmaceutical composition, comprising the polypeptide according to claim 1 and a pharmaceutically acceptable carrier.

6. A composition, comprising the polynucleotide according to claim 2 or a vector harboring said polynucleotide and a pharmaceutically acceptable carrier.

* * * * *